US009359439B2

(12) United States Patent
Goletz et al.

(10) Patent No.: US 9,359,439 B2
(45) Date of Patent: Jun. 7, 2016

(54) FAB-GLYCOSYLATED ANTIBODIES

(75) Inventors: Steffen Goletz, Berlin (DE); Antje Danielczyk, Berlin (DE); Lars Stoeckl, Berlin (DE)

(73) Assignee: Glycotope GmbH, Berlin (DE)

( * ) Notice: Subject to any disclaimer, the term of this patent is extended or adjusted under 35 U.S.C. 154(b) by 287 days.

(21) Appl. No.: 13/816,390

(22) PCT Filed: Aug. 10, 2011

(86) PCT No.: PCT/EP2011/063791
§ 371 (c)(1),
(2), (4) Date: Mar. 26, 2013

(87) PCT Pub. No.: WO2012/020065
PCT Pub. Date: Feb. 16, 2012

(65) Prior Publication Data
US 2013/0209458 A1  Aug. 15, 2013

(30) Foreign Application Priority Data
Aug. 10, 2010  (WO) ............... PCT/EP2010/004878

(51) Int. Cl.
*A61K 39/395* (2006.01)
*C07K 16/28* (2006.01)
*C07K 16/00* (2006.01)
*C07K 16/30* (2006.01)
*C07K 16/18* (2006.01)
*A61K 39/00* (2006.01)

(52) U.S. Cl.
CPC ............. *C07K 16/2863* (2013.01); *C07K 16/00* (2013.01); *C07K 16/18* (2013.01); *C07K 16/3092* (2013.01); *A61K 2039/505* (2013.01); *C07K 2317/41* (2013.01); *C07K 2317/55* (2013.01); *C07K 2317/73* (2013.01); *C07K 2317/732* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,943,533 A | | 7/1990 | Mendelsohn et al. |
| 6,172,213 B1 * | | 1/2001 | Lowman et al. ............ 536/23.53 |
| 9,051,370 B2 * | | 6/2015 | Goletz et al. |
| 2006/0051353 A1 * | | 3/2006 | Colombel et al. ......... 424/145.1 |
| 2009/0181016 A1 * | | 7/2009 | Lenz .......................... 424/133.1 |

FOREIGN PATENT DOCUMENTS

| EP | 2281844 A1 | 2/2011 |
|---|---|---|
| WO | 93/13806 A1 | 7/1993 |
| WO | 95/15769 A1 | 6/1995 |
| WO | 96/40210 A1 | 12/1996 |
| WO | 03/016466 A2 | 2/2003 |
| WO | 03/074679 A2 | 9/2003 |
| WO | 2004/065423 A2 | 8/2004 |
| WO | 2005/016455 A2 | 2/2005 |
| WO | 2005/017130 A2 | 2/2005 |
| WO | 2005/080585 A1 | 9/2005 |
| WO | 2006/125207 A2 | 11/2006 |
| WO | 2007/005786 A2 | 1/2007 |
| WO | 2007/034210 A2 | 3/2007 |
| WO | 2008/028686 A2 | 3/2008 |
| WO | WO 2008028686 A2 * | 3/2008 |
| WO | 2008/101177 A2 | 8/2008 |
| WO | 2009/149185 A2 | 12/2009 |

OTHER PUBLICATIONS

Karapetis et al., N Engl J Med. Oct. 23, 2008;359(17):1757-65. doi: 10.1056/NEJMoa0804385.*
Bibeau et al., J Clin Oncol. Mar. 1, 2009;27(7)1122-9. doi: 10.1200/JCO.2008.18.0463. Epub Jan. 21, 2009.*
Souliéres et al., Curr Oncol. Jul. 2010;17 Suppl 1:S31-40.*
Schlaeth et al., Cancer Sci. May 2010;101(5):1080-8. doi: 10.1111/j.1349-7006.2010.01505.x. Epub Jan. 20, 2010.*
International Preliminary Report on Patentability and Written Opinion for Application No. PCT/EP2011/063791, 8 pages, dated Feb. 12, 2013.
Danielczyk, Antje et al., "PankoMab: a potent new generation anti-tumour MUC1 antibody," Cancer Immunol. Immunother., vol. 55(11):1337-1347 (2006).
Huang, Lihua et al., "Impact of variable domain glycosylation on antibody clearance: An LC/MS characterization," Analytical Biochemistry, vol. 349:197-207 (2006).
Jefferis, Roy, "Glycosylation of Antibody Therapeutics: Optimisation for Purpose," Methods in Molecular Biology, Recombinant Proteins From Plants, L. Faye (Ed.), Chapter 13, vol. 483:223-238 (2009).
Karsten, Uwe et al., "Binding patterns of DTR-specific antibodies reveal a glycosylation-conditioned tumor-specific epitope of the epithelial mucin (MUC1)," Glycobiology, vol. 14(8):681-692 (2004).
Langer, Robert, "New Methods of Drug Delivery," Science, vol. 249:1527-1533 (1990).
Millward, Thomas A. et al., "Effect of constant and variable domain glycosylation on pharmacokinetics of therapeutic antibodies in mice," Biologicals, vol. 36:41-47 (2008).
Scallon, Bernard J. et al., "Higher levels of sialylated Fc glycans in immunoglobulin G molecules can adversely impact functionality," Molecular Immunology, vol. 44:1524-1534 (2007).
Sola, Ricardo J. et al., "Glycosylation of Therapeutic Proteins, An Effective Strategy to Optimize Efficacy," Biodrugs, vol. 24(1):9-21 (2010).
Stork, R. et al., "N-Glycosylation as Novel Strategy to Improve Pharmacokinetic Properties of Bispecific Single-chain Diabodies," The Journal of Biological Chemistry, vol. 283, No. 12, Mar. 21, 2008, pp. 7804-7812.
Byrne, Barry et al., "Sialic acids: carbohydrate moieties that influence the biological and physical properties of biopharmaceutical proteins and living cells," Drug Discovery Today, vol. 12(7/8):319-326 (2007).

(Continued)

*Primary Examiner* — Michael Szperka
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to a method for controlling the circulation half-life of antibodies by adjusting the amount of sialic acid in the carbohydrates attached to the Fab part of the antibodies. Furthermore, the present invention provides antibodies having an increased circulation half-life.

11 Claims, 22 Drawing Sheets

(56) References Cited

OTHER PUBLICATIONS

Constantinou, Antony et al., "Modulation of Antibody Pharmacokinetics by Chemical Polysialylation," Bioconjugate Chem., vol. 19:643-650 (2008).

Endo, Tamao et al., "Glycosylation of the Variable Region of Immunoglobulin G-Site Specific maturation of the Sugar Chains," Molecular Immunology, vol. 32(13):931-940 (1995).

Kaneko, Yoshikatsu et al., "Anti-Inflammatory Activity of Immunoglobulin G Resulting from Fc Sialylation," Science, vol. 313:670-673 (2006).

Leung, Shui-on et al., "Engineering a Unique Glycosylation Site for Site-Specific Conjugation of Haptens to Antibody Fragments," The Journal of Immunology, vol. 154:5919-5926 (1995).

Leung, Shui-on et al., "The Effects of Domain Deletion, Glycosylation, and Long IgG3 Hinge on the Biodistribution and Serum Stability Properties of a Humanized IgGx Immunoglobulin hLL2, and Its Fragments," Clinical Care Research, vol. S:3106s-3117s (1999).

Rosebrough, S.F. et al., "Isothiocyanate-Trigalactose: Application for Antibody-Targeted Delivery of Diagnostic and Therpeutic Agents," Cancer Biotherapy & Radiopharmaceuticals, vol. 15(5):507-515 (2000).

Sato, Koh et al., "Humanization of an anti-human IL-6 mouse monoclonal antibody glycosylated in its heavy chain variable region," Hum. Antibod. Hybridomas, vol. 7:175-183 (1996).

Shinkawa, Toyohide et al., "The Absense of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278(5):3466-3473 (2003).

Wright, Ann et al., "Antibody variable region glycosylation: position effects on antigen binding and carbohydrate structure," The EMBO Journal, vol. 10(10):2717-2723 (1991).

International Search Report and Written Opinion for Application No. PCT/EP2011/063791, 17 pages, dated Jan. 18, 2012.

\* cited by examiner

A

B

A

B

A

B

C

```
                        SEQUENCE LISTING

<160> NUMBER OF SEQ ID NOS: 26

<210> SEQ ID NO 1
<211> LENGTH: 5
<212> TYPE: PRT
<213> ORGANISM: Artificial
<220> FEATURE:
<223> OTHER INFORMATION: Cetuximab CDRH1

<400> SEQUENCE: 1

Asn Tyr Gly Val His
1               5

<210> SEQ ID NO 2
<211> LENGTH: 16
<212> TYPE: PRT
<213> ORGANISM: Artificial
<220> FEATURE:
<223> OTHER INFORMATION: Cetuximab CDRH2

<400> SEQUENCE: 2

Val Ile Trp Ser Gly Gly Asn Thr Asp Tyr Asn Thr Pro Phe Thr Ser
1               5                   10                  15

<210> SEQ ID NO 3
<211> LENGTH: 11
<212> TYPE: PRT
<213> ORGANISM: Artificial
<220> FEATURE:
<223> OTHER INFORMATION: Cetuximab CDRH3

<400> SEQUENCE: 3

Ala Leu Thr Tyr Tyr Asp Tyr Glu Phe Ala Tyr
1               5                   10

<210> SEQ ID NO 4
<211> LENGTH: 11
<212> TYPE: PRT
<213> ORGANISM: Artificial
<220> FEATURE:
<223> OTHER INFORMATION: Cetuximab CDRL1

<400> SEQUENCE: 4

Arg Ala Ser Gln Ser Ile Gly Thr Asn Ile His
1               5                   10

<210> SEQ ID NO 5
<211> LENGTH: 7
<212> TYPE: PRT
<213> ORGANISM: Artificial
<220> FEATURE:
<223> OTHER INFORMATION: Cetuximab CDRL2

<400> SEQUENCE: 5

Tyr Ala Ser Glu Ser Ile Ser
```

<210> SEQ ID NO 6
<211> LENGTH: 9
<212> TYPE: PRT
<213> ORGANISM: Artificial
<220> FEATURE:
<223> OTHER INFORMATION: Cetuximab CDRL3

<400> SEQUENCE: 6

Gln Gln Asn Asn Asn Trp Pro Thr Thr
1               5

<210> SEQ ID NO 7
<211> LENGTH: 5
<212> TYPE: PRT
<213> ORGANISM: Artificial
<220> FEATURE:
<223> OTHER INFORMATION: Pankomab CDRH1

<400> SEQUENCE: 7

Asn Tyr Trp Met Asn
1               5

<210> SEQ ID NO 8
<211> LENGTH: 19
<212> TYPE: PRT
<213> ORGANISM: Artificial
<220> FEATURE:
<223> OTHER INFORMATION: Pankomab CDRH2

<400> SEQUENCE: 8

Glu Ile Arg Leu Lys Ser Asn Asn Tyr Thr Thr His Tyr Ala Glu Ser
1               5                   10                  15

Val Lys Gly

<210> SEQ ID NO 9
<211> LENGTH: 6
<212> TYPE: PRT
<213> ORGANISM: Artificial
<220> FEATURE:
<223> OTHER INFORMATION: Pankomab CDRH3

<400> SEQUENCE: 9

His Tyr Tyr Phe Asp Tyr
1               5

<210> SEQ ID NO 10
<211> LENGTH: 16
<212> TYPE: PRT
<213> ORGANISM: Artificial
<220> FEATURE:
<223> OTHER INFORMATION: Pankomab CDRL1

<400> SEQUENCE: 10

Arg Ser Ser Lys Ser Leu Leu His Ser Asn Gly Ile Thr Tyr Phe Phe
1               5                   10                  15

<210> SEQ ID NO 11
<211> LENGTH: 7
<212> TYPE: PRT
<213> ORGANISM: Artificial
<220> FEATURE:
<223> OTHER INFORMATION: Pankomab CDRL2

<400> SEQUENCE: 11

Gln Met Ser Asn Leu Ala Ser
1               5

<210> SEQ ID NO 12
<211> LENGTH: 9
<212> TYPE: PRT
<213> ORGANISM: Artificial
<220> FEATURE:
<223> OTHER INFORMATION: Pankomab CDRL3

<400> SEQUENCE: 12

Ala Gln Asn Leu Glu Leu Pro Pro Thr
1               5

<210> SEQ ID NO 13
<211> LENGTH: 4
<212> TYPE: PRT
<213> ORGANISM: Artificial
<220> FEATURE:
<223> OTHER INFORMATION: TA-Muc1 epitope

<400> SEQUENCE: 13

Pro Asp Thr Arg
1

<210> SEQ ID NO 14
<211> LENGTH: 5
<212> TYPE: PRT
<213> ORGANISM: Artificial
<220> FEATURE:
<223> OTHER INFORMATION: TA-Muc1 epitope

<400> SEQUENCE: 14

Pro Asp Thr Arg Pro
1               5

<210> SEQ ID NO 15
<211> LENGTH: 10
<212> TYPE: PRT
<213> ORGANISM: Artificial
<220> FEATURE:
<223> OTHER INFORMATION: Alemtuzumab CDRH1

<400> SEQUENCE: 15

Gly Phe Thr Phe Thr Asp Phe Tyr Met Asn
1               5                   10

<210> SEQ ID NO 16
<211> LENGTH: 19
<212> TYPE: PRT
<213> ORGANISM: Artificial
<220> FEATURE:
<223> OTHER INFORMATION: Alemtuzumab CDRH2

<400> SEQUENCE: 16

Phe Ile Arg Asp Lys Ala Lys Gly Tyr Thr Thr Glu Tyr Asn Pro Ser
1               5                   10                  15

Val Lys Gly

<210> SEQ ID NO 17
<211> LENGTH: 10
<212> TYPE: PRT
<213> ORGANISM: Artificial
<220> FEATURE:
<223> OTHER INFORMATION: Alemtuzumab CDRH3

<400> SEQUENCE: 17

```
Glu Gly His Thr Ala Ala Pro Phe Asp Tyr
1               5                   10

<210> SEQ ID NO 18
<211> LENGTH: 11
<212> TYPE: PRT
<213> ORGANISM: Artificial
<220> FEATURE:
<223> OTHER INFORMATION: Alemtuzumab CDRL1

<400> SEQUENCE: 18

Lys Ala Ser Gln Asn Ile Asp Lys Tyr Leu Asn
1               5                   10

<210> SEQ ID NO 19
<211> LENGTH: 7
<212> TYPE: PRT
<213> ORGANISM: Artificial
<220> FEATURE:
<223> OTHER INFORMATION: Alemtuzumab CDRL2

<400> SEQUENCE: 19

Asn Thr Asn Asn Leu Gln Thr
1               5

<210> SEQ ID NO 20
<211> LENGTH: 9
<212> TYPE: PRT
<213> ORGANISM: Artificial
<220> FEATURE:
<223> OTHER INFORMATION: Alemtuzumab CDRL3

<400> SEQUENCE: 20

Leu Gln His Ile Ser Arg Pro Arg Thr
1               5

<210> SEQ ID NO 21
<211> LENGTH: 5
<212> TYPE: PRT
<213> ORGANISM: Artificial
<220> FEATURE:
<223> OTHER INFORMATION: Solanezumab CDRH1

<400> SEQUENCE: 21

Arg Tyr Ser Met Ser
1               5

<210> SEQ ID NO 22
<211> LENGTH: 17
<212> TYPE: PRT
<213> ORGANISM: Artificial
<220> FEATURE:
<223> OTHER INFORMATION: Solanezumab CDRH2

<400> SEQUENCE: 22

Gln Ile Asn Ser Val Gly Asn Ser Thr Tyr Tyr Pro Asp Thr Val Lys
1               5                   10                  15

Gly

<210> SEQ ID NO 23
<211> LENGTH: 3
<212> TYPE: PRT
<213> ORGANISM: Artificial
<220> FEATURE:
<223> OTHER INFORMATION: Solanezumab CDRH3
```

```
<400> SEQUENCE: 23

Gly Asp Tyr
1

<210> SEQ ID NO 24
<211> LENGTH: 16
<212> TYPE: PRT
<213> ORGANISM: Artificial
<220> FEATURE:
<223> OTHER INFORMATION: Solanezumab CDRL1

<400> SEQUENCE: 24

Arg Ser Ser Gln Ser Leu Ile Tyr Ser Asp Gly Asn Ala Tyr Leu His
1               5                   10                  15

<210> SEQ ID NO 25
<211> LENGTH: 7
<212> TYPE: PRT
<213> ORGANISM: Artificial
<220> FEATURE:
<223> OTHER INFORMATION: Solanezumab CDRL2

<400> SEQUENCE: 25

Lys Val Ser Asn Arg Phe Ser
1               5

<210> SEQ ID NO 26
<211> LENGTH: 9
<212> TYPE: PRT
<213> ORGANISM: Artificial
<220> FEATURE:
<223> OTHER INFORMATION: Solanezumab CDRL3

<400> SEQUENCE: 26

Ser Gln Ser Thr His Val Pro Trp Thr
1               5
```

FAB-GLYCOSYLATED ANTIBODIES

FIELD OF THE INVENTION

The present invention pertains to the field of antibodies. In particular, antibodies having highly sialylated glycans attached to their Fab part are provided. Furthermore, the present invention provides a method for controlling the circulation half-life of antibodies via their Fab-sialylation.

BACKGROUND OF THE INVENTION

Today, antibodies are widely used agents in the field of medicine and research. In medicine, they find application in many different fields. For example, antibodies are used as labeling agents for detecting certain markers which allow the diagnosis and/or prognosis of diseases or the determination of specific body parameters such as, for example, the presence or concentration of certain hormones.

Furthermore, antibodies are also used as therapeutic agents in the treatment and prophylaxis of a variety of diseases such as cancer, cardiovascular diseases, inflammatory diseases, macular degeneration, transplant rejection, multiple sclerosis, and viral infections. In these therapies, the antibody may possess therapeutic activity on it own, for example by blocking receptors or messenger molecules, thereby inhibiting their disease-relevant functions, or by recruiting and activating components of the patient's immune system. Alternatively, the antibody may be coupled to another agent having therapeutic activity. In particular in the treatment of cancer and infections, said further agent has cell-killing activity and may be, for example a radioisotope or a cytotoxin. In another application, antibodies may be used to passively immunize a patient by transferring suitable antibodies into the patient's circulation.

A critical aspect of the in vivo application of antibodies, in particular of their therapeutic use, is the time the antibodies remain in the patient's body, i.e. the circulation half-life of the antibodies.

Many approaches to increase the circulation half-life of proteins involve artificial modifications of the proteins such as conjugating them with other molecules which increase the half-life or fusing them to other half-life-increasing proteins or peptides. However, these approaches involve certain disadvantages. They normally involve complicated production processes and there are frequently problems with their biocompatibility or pharmaceutical approval. Moreover, these modifications often are detrimental to the biological activities of the antibodies, in particular their antigen binding properties and their downstream signaling such as antibody-dependent cell-mediated cytotoxicity (ADCC) and complement-dependent cytotoxicity (CDC).

Furthermore, with respect to glycoproteins such as FSH in some cases the amount of sialic acids attached to the carbohydrate chains of the glycoproteins influences the clearance rate and thus, the circulation half-life of the glycoprotein. However, according to the state of the art this principle cannot be attributed to antibodies. First, a high degree of sialylation of the carbohydrate chain attached to the Fc region of an IgG antibody negatively affects the biological activities of the antibody. In particular, the ADCC of the antibody is greatly reduced due to a decreased affinity of the Fc region to the respective Fc receptor (see, e.g., Scallon, B. J. et al. (2006) Molecular Immunology 44, 1524-1534). Furthermore, the degree of sialylation of carbohydrate chains attached to glycosylation sites in the Fab region is considered to have no impact on the circulation half-life of the antibody but rather influences antigen binding (see, e.g., Huang, L. et al. (2006) Analytical Biochemistry 349, 197-207, Millward, T. A. et al. (2008) Biologicals 36, 41-47, Jefferis, R. (2009) Methods in Molecular Biology 483, 223-238, and Sold, R. J. et al. (2010) Biodrugs 24, 9-21).

On the other hand, also antibodies having a low circulation half-life are important for some applications. For example, for diagnostic purposes using radioactive imaging methods, antibodies conjugated to radionuclides are used. Since the imaging procedure can be performed in a relatively short time and the radionuclides conjugated to the antibodies have certain adverse side effects, a fast clearance of the conjugate from the patient's circulation is advantageous.

Therefore, there is a need in the art to regulate, in particular to increase or decrease the circulation half-life of antibodies, in particular therapeutically or diagnostically useful antibodies, without using chemical conjugates or fusion proteins.

SUMMARY OF THE INVENTION

The present inventors have found that the amount of sialic acids on carbohydrate chains attached to one or more glycosylation sites in the Fab part of antibodies greatly influences the circulation half-life of antibodies. This principle can be used to control the circulation half-life and thus, the bioavailability of antibodies, in particular of therapeutically or diagnostically useful antibodies. To be able to individually adjust the circulation half-life of antibodies is advantageous, for example, for optimizing the therapeutic efficacy and balancing the therapeutic effect and possible adverse side effects of the antibodies. Furthermore, it is advantageous for diagnostic purposes to adjust the circulation half-life of antibodies to a low level in order to avoid adverse side effects.

Therefore, in a first aspect, the present invention is directed to a method for controlling the circulation half-life of an antibody or a functional fragment or derivative thereof, comprising the step of (a) for increasing the circulation half-life
  (a1) increasing in a composition comprising the antibody or functional fragment or derivative thereof the amount of sialic acids in the carbohydrates attached to at least one glycosylation site present in the Fab part of the antibodies or fragments or derivatives thereof; and/or
  (a2) removing one or more glycosylation sites present in the Fab part of the antibody or fragment or derivative thereof; and/or
  (a3) decreasing in a composition comprising the antibody or functional fragment or derivative thereof the amount of free galactose units in the carbohydrates attached to at least one glycosylation site present in the Fab part of the antibodies or fragments or derivatives thereof; or
(b) for decreasing the circulation half-life
  (b1) decreasing in a composition comprising the antibody or functional fragment or derivative thereof the amount of sialic acids in the carbohydrates attached to at least one glycosylation site present in the Fab part of the antibodies or fragments or derivatives thereof; and/or
  (b2) introducing one or more glycosylation sites into the Fab part of the antibody or fragment or derivative thereof; and/or
  (b3) increasing in a composition comprising the antibody or functional fragment or derivative thereof the amount of free galactose units in the carbohydrates attached to at least one glycosylation site present in the Fab part of the antibodies or fragments or derivatives thereof.

In a second aspect, the present invention provides an antibody composition comprising antibodies or functional fragments or derivatives thereof, characterized in that the antibodies or fragments or derivatives thereof comprise at least one glycosylation site present in their Fab part, and characterized in that in the composition at least 65% of the carbohydrates attached to the Fab part of the antibodies or fragments or derivatives thereof carry at least one terminal sialic acid residue and/or less than 35% of the carbohydrates attached to the Fab part of the antibodies or fragments or derivatives thereof carry at least two free galactose units. Furthermore, the present invention provides specific antibody compositions and their use in medicine.

In a third aspect, the present invention provides a method for producing an antibody composition comprising an antibody or functional fragment or derivative thereof having a desired circulation half-life, comprising the step of expressing said antibody or functional fragment or derivative thereof in a host cell, wherein the method for controlling the half-life of the antibody or fragment or derivative thereof according to the present invention is performed using step (a1), step (a3), step (b1) or step (b3) of said method and/or the host cell expresses an antibody or functional fragment or derivative thereof obtained by the method for controlling the half-life of the antibody or fragment or derivative thereof according to the present invention using step (a2) or (b2).

In preferred embodiments, the antibodies provided by the present invention additionally have a greatly improved ability to induce the different activities of the immune system, in particular ADCC. This is achieved by the optimized glycosylation pattern of the antibodies, resulting—besides the controlled circulation half-life—in an improved antibody activity, in particular an improved Fc receptor binding and activation. Thus, the present invention provides in a further aspect antibody compositions comprising antibodies which have an increased circulation half-life and an improved ADCC activity, as well as a method for producing such antibodies. These antibodies are particularly suitable for therapeutic use since their bioavailability as well as their biological activity are increased, which both contribute to an increased therapeutic efficacy. Thus, another advantage of the present invention is the capability of providing antibodies having at the same time an increased circulation half-life and an increased biological activity. The increase in circulation half-life is preferably achieved by the method according to the first aspect of the present invention. In addition, the increase in biological activity preferably is an increased ADCC activity, in particular resulting from a stronger binding to the respective Fc receptors. Such increased ADCC activity may in particular be achieved by optimizing the glycosylation pattern of the antibody, for example by reducing the amount of fucose residues in the carbohydrates attached to at least one glycosylation site present in the Fc part of the antibodies.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DEFINITIONS

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The term "antibody" particularly refers to a protein comprising at least two heavy chains and two light chains connected by disulfide bonds. The term "antibody" includes naturally occurring antibodies as well as all recombinant forms of antibodies, e.g., antibodies expressed in prokaryotes, non-glycosylated antibodies, humanized antibody, and chimeric antibody. Each heavy chain is comprised of a heavy chain variable region (VH) and a heavy chain constant region (CH). Each light chain is comprised of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" according to the invention, however, also includes antibodies such as heavy chain antibodies, i.e. antibodies only composed of one or more, in particular two heavy chains, and nanobodies, i.e. antibodies only composed of a single monomeric variable domain.

In particular, the antibody may be of any isotype such as IgA, IgD, IgE, IgG or IgM, including any subclass such as IgG1, IgG2, IgG3, IgG4, IgA1 or IgA2. Preferably, the antibody is an IgG1- or IgG2-antibody, more preferably an IgG1-antibody. The heavy chain constant regions may be of any type such as γ-, δ-, α-, μ- or ε-type heavy chains. Furthermore, the light chain constant region may also be of any type such as κ- or λ-type light chains. Preferably, the light chain of the antibody is a κ-chain.

For indicating the amino acid positions of the heavy chain and light chain variable regions, the Kabat numbering system is used herein (Kabat, E. A. et al. (1991) *Sequences of Proteins of Immunological Interest*, 5$^{th}$ edition, NIH Publication No. 91-3242). According to said system, the heavy chain comprises amino acid positions from position 0 to position 113 including position 35A, 35B, 52A to 52C, 82A to 82C and 100A to 100K. The CDRs of the heavy chain variable region are located, according to the Kabat numbering, at positions 31 to 35B (CDR1), 50 to 65 (CDR2) and 95 to 102 (CDR3). The remaining amino acid positions form the framework regions FR1 to FR4. The light chain variable region comprises positions 0 to 109 including positions 27A to 27F, 95A to 95F and 106A. The CDRs are located at positions 24 to 34 (CDR1), 50 to 56 (CDR2) and 89 to 97 (CDR3). Depending on the initial formation of the specific gene of an antibody, not all of these positions have to be present in a given heavy chain variable region or light chain variable region. In case an amino acid position in a heavy chain or light chain variable region is mentioned herein, unless otherwise indicated it is referred to the position according to the Kabat numbering.

The "Fab part" of an antibody or a fragment or derivative thereof in particular refers to a part of the antibody comprising the heavy and light chain variable regions (VH and VL) and the first heavy and light chain constant regions (CH1 and CL). In cases where the antibody or fragment or derivative thereof does not comprise all of these regions, then the term "Fab part" only refers to those of the regions VH, VL, CH1 and CL which are present in the antibody or fragment or derivative thereof. Preferably, "Fab part" refers to that part of an antibody corresponding to the fragment obtained by digesting a natural antibody with papain which contains the antigen binding activity of the antibody. In particular, the Fab part of an antibody or fragment or derivative thereof encompasses the antigen binding site or antigen binding ability thereof. Preferably, the Fab part comprises at least the VH region of the antibody.

The "Fc part" of an antibody or a fragment or derivative thereof in particular refers to a part of the antibody comprising the heavy chain constant regions 2, 3 and—where applicable—4 (CH2, CH3 and CH4). In cases where the antibody or fragment or derivative thereof does not comprise all of these regions, then the term "Fc part" only refers to those of the regions CH2, CH3 and CH4 which are present in the antibody or fragment or derivative thereof. Preferably, "Fc part" refers to that part of an antibody corresponding to the fragment obtained by digesting a natural antibody with papain which does not contain the antigen binding activity of the antibody. In particular, the Fc part of an antibody or fragment or derivative thereof is capable of binding a Fc receptor and thus, e.g. comprises a Fc receptor binding site or a Fc receptor binding ability. Furthermore, preferably it is capable of inducing ADCC. Preferably, the Fc part comprises at least the CH2 region of the antibody.

A schematic drawing of an antibody of the IgG class including the Fab part and the Fc part can be seen in FIG. 21A.

According to the present invention, the term "chimeric antibody" in particular refers to an antibody wherein the constant regions are derived from a human antibody or a human antibody consensus sequence, and wherein at least one and preferably both variable regions are derived from a non-human antibody, in particular from a mouse antibody.

According to the present invention, the term "humanized antibody" in particular refers to an antibody wherein at least one CDR is derived from a non-human antibody, and wherein the constant regions, if present, and at least one framework region of a variable region are derived from a human antibody or a human antibody consensus sequence. Preferably, all CDRs of the heavy chain variable region or, more preferably, all CDRs of the heavy chain variable region and the light chain variable region, are derived from the non-human antibody. Furthermore, preferably all framework regions of the heavy chain variable region or, more preferably, all framework regions of the heavy chain variable region and the light chain variable region, are derived from a human antibody or a human antibody consensus sequence. The CDRs preferably are derived from the same non-human antibody. The first three or all of the framework regions of one variable region preferably are derived from the same human antibody or human antibody consensus sequence, however, the framework regions of the heavy chain variable region do not have to be derived from the same human antibody or human antibody consensus sequence as the framework regions of the light chain variable region. In particular preferred embodiments, the humanized antibody is capable of binding to the same antigens, in particular the same epitopes as the non-human antibody from which the one or more CDRs are derived.

Preferably, the CDRs of the humanized antibody which are derived from the non-human antibody are identical to the CDRs of the non-human antibody. Furthermore, the framework regions of the humanized antibody which are derived from the human antibody or human antibody consensus sequence may be identical to the framework regions of the human antibody or human antibody consensus sequence. In another embodiment, the framework regions of the humanized antibody may have one or more amino acid substitutions compared to the framework regions of the human antibody or human antibody consensus sequence from which they are derived. The substituted amino acid residues are preferably replaced by the corresponding amino acid residues of the non-human antibody from which one or more of the CDRs are derived (in particular those corresponding amino acid residues which are at the same position according to the Kabat numbering). In particular, the framework regions of a variable region (heavy chain variable region and/or light chain variable region) of the humanized antibody preferably comprise no more than 30 amino acid substitutions, preferably no more than 25, no more than 20, nor more than 15, no more than 12, no more than 10 or no more than 8 amino acid substitutions.

In preferred embodiments, all framework regions of the heavy chain variable region of the humanized antibody, taken together, share a homology or an identity of at least 70%, preferably at least 75%, at least 80%, at least 85% or at least 90%, with the framework regions of the heavy chain variable region of the human antibody or human antibody consensus sequence from which they are derived. Furthermore, all framework regions of the light chain variable region of the humanized antibody, taken together, preferably share a homology or an identity of at least 70%, preferably at least 75%, at least 80%, at least 85% or at least 90%, with the framework regions of the light chain variable region of the human antibody or human antibody consensus sequence from which they are derived.

The constant regions of a chimeric or humanized antibody may be derived from any human antibody or human antibody consensus sequence. In particular, the heavy chain constant regions may be of any type such as $\gamma$-, $\delta$-, $\alpha$-, $\mu$- or $\epsilon$-type heavy chains. The chimeric or humanized antibody may thus be of any isotype such as IgA, IgD, IgE, IgG or IgM, including any subclass such as IgG1, IgG2, IgG3, IgG4, IgA1 or IgA2. Preferably, the chimeric or humanized antibody is an IgG1- or IgG2-antibody, more preferably an IgG1-antibody. Furthermore, the light chain constant region may also be of any type such as $\kappa$- or $\lambda$-type light chains. Preferably, the light chain of a chimeric or humanized antibody is a $\kappa$-chain.

A target amino acid sequence is "derived" from a reference amino acid sequence if the target amino acid sequence shares a homology or identity over its entire length with a corresponding part of the reference amino acid sequence of at least 60%, preferably at least 70%, at least 75%, more preferably at least 80%, at least 85%, at least 90%, at least 93%, at least 95% or at least 97%. For example, if a framework region of a humanized antibody is derived from a variable region of a particular human antibody, then the amino acid of the framework region of the humanized antibody shares a homology or identity over its entire length with the corresponding framework region of the human antibody of at least 60%, preferably at least 70%, at least 75%, more preferably at least 80%, at least 85%, at least 90%, at least 93%, at least 95% or at least 97%. The "corresponding part" or "corresponding framework region" means that, for example, framework region 1 of a heavy chain variable region (FRH1) of a target antibody corresponds to framework region 1 of the heavy chain variable region of the reference antibody. The same is true, for example, for FRH2, FRH3, FRH4, FRL1, FRL2, FRL3 and FRL4. In particular embodiments, a target amino acid sequence which is "derived" from a reference amino acid sequence is 100% homologous, or in particular 100% identical, over its entire length with a corresponding part of the reference amino acid sequence.

A "fragment or derivative" of an antibody in particular is a protein or glycoprotein which is derived from said antibody and is capable of binding to the same antigen, in particular to the same epitope as the antibody. Thus, a fragment or derivative of an antibody herein generally refers to a functional fragment or derivative. A functional fragment or derivative of an antibody in particular is capable of binding to the same antigen, especially the same epitope as the antibody. In particularly preferred embodiments, the fragment or derivative of an antibody comprises a heavy chain variable region. It has been shown that the antigen-binding function of an antibody can be performed by fragments of a full-length antibody or derivatives thereof. Examples of fragments or derivatives of an antibody include (i) Fab fragments, monovalent fragments consisting of the variable region and the first constant domain of each the heavy and the light chain; (ii) $F(ab)_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) $(Fv)_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. These antibody fragments and derivatives are obtained using conventional techniques known to those with skill in the art.

"Specific binding" preferably means that an agent such as an antibody binds stronger to a target such as an epitope for which it is specific compared to the binding to another target. An agent binds stronger to a first target compared to a second target if it binds to the first target with a dissociation constant ($K_d$) which is lower than the dissociation constant for the second target. Preferably the dissociation constant for the target to which the agent binds specifically is more than 2-fold, preferably more than 5-fold, more preferably more than 10-fold, even more preferably more than 20-fold, 50-fold, 100-fold, 200-fold, 500-fold or 1000-fold lower than the dissociation constant for the target to which the agent does not bind specifically.

The term "sialic acid" in particular refers to any N- or O-substituted derivatives of neuraminic acid. It preferably refers to both 5-N-acetylneuraminic acid and 5-N-glycolylneuraminic acid, more preferably only to 5-N-acetylneuraminic acid. The sialic acid, in particular the 5-N-acetylneuraminic acid preferably is attached to a carbohydrate chain of a glycoprotein via a 2,3- or 2,6-linkage. Preferably, in the antibody compositions described herein both 2,3-as well as 2,6-linked sialic acids are present.

The term "free galactose unit" as referred herein in particular refers to a galactose unit which is attached via its reducing end to a carbohydrate structure and which does not carry a sialic acid at its 6-position. In particular, the free galactose unit does not carry any saccharide unit at its 6-position. In certain embodiments, the free galactose unit does not carry any chemical modification or substituent at its 6-position. In particular, the galactose unit does not carry a sialic acid, preferably any saccharide and more preferably any chemical modification or substituent at any one of its 2-position, 3-position, 4-position, 5-position and 6-position. In this respect, the hydrogen and hydroxyl residues of the galactose units are not considered as chemical modifications or substituents.

The term "glycosylation site" in particular refers to any amino acid sequence which can be recognized by an enzyme capable of catalyzing the attachment of a monosaccharide unit or a carbohydrate chain to a peptide chain. Preferably, the glycosylation site includes the amino acid residue to which the monosaccharide unit or a carbohydrate chain is attached. Preferred glycosylation sites are N-glycosylation sites, in particular N-glycosylation sites comprising an asparagine residue as attachment site, and O-glycosylation sites, in particular O-glycosylation sites comprising a serine or threonine residue as attachment site. A preferred N-glycosylation site comprises the amino acid sequence Asn Xaa Ser/Thr, wherein Xaa is any amino acid preferably except Pro. This amino acid sequence refers to a sequence of three consecutive amino acids, wherein the first amino acid residue is an asparagine residue, the second amino acid residue can be any amino acid residue, in particular any naturally occurring amino acid residue, except proline, and the third amino acid residue is a serine or threonine. When glycosylated, the carbohydrate chain is attached to the asparagine residue.

The numbers given herein, in particular the relative amounts of a specific glycosylation property, are preferably to be understood as approximate numbers. In particular, the numbers preferably may be up to 10% higher and/or lower, in particular up to 9%, 8%, 7%, 6%, 5%, 4%, 3%, 2% or 1% higher and/or lower.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3'-capping.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. Preferably, the host cell is a human cell, in particular an immortalized human cell, preferably an immortalized human blood cell such as an immortalized human myeloid cell or an immortalized human myeloid leukemia cell. Furthermore, the host cell may also be an immortalized human tumor cell. A nucleic acid may be present in the host cell in the form of a single copy or of two or more copies and, in one embodiment, is expressed in the host cell.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "cancer" according to the invention in particular comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, colorectal carcinomas, head and neck carcinomas, or metastases of the cancer types or tumors described above. The term cancer according to the invention also comprises cancer metastases.

By "tumor" is meant a group of cells or tissue that is formed by misregulated cellular proliferation, in particular cancer. Tumors may show partial or complete lack of structural organization and functional coordination with the normal tissue, and usually form a distinct mass of tissue, which may be either benign or malignant. In particular, the term "tumor" refers to a malignant tumor. According to one embodiment, the term "tumor" or "tumor cell" also refers to non-solid cancers and cells of non-solid cancers such as leukemia cells. According to another embodiment, respective non-solid cancers or cells thereof are not encompassed by the terms "tumor" and "tumor cell".

By "metastasis" is meant the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

The term "antibody composition" in particular refers to any composition comprising an antibody or a fragment or derivative thereof. The antibody composition may be a fluid or solid composition, and also includes lyophilized or reconstituted antibody compositions. Preferably a fluid composition is used, more preferably an aqueous composition. It preferably further comprises a solvent such as water, a buffer for adjusting the pH value, and optionally further agents for stabilizing the antibody or preventing degradation of the antibody. The antibody composition preferably comprises a reasonable amount of antibodies, in particular at least 1 μmol, preferably at least 1 pmol, at least 1 nmol or at least 1 μmmol of the antibody or fragment or derivative thereof. However, in certain embodiments also antibody compositions comprising only one antibody molecule or fragment or derivative thereof are included. A composition comprising a specific antibody or fragment or derivative thereof may additionally comprise further antibodies or fragments or derivatives thereof. However, preferably a composition comprising a specific antibody or fragment or derivative thereof does not comprise other antibodies or antibody fragments or derivatives apart from the specific antibody or fragment or derivative thereof. In particular, at least 75%, preferably at least 80%, at least 85%, at least 90%, at least 95%, at least 97%, at least 98% or at least 99%, most preferably about 100% of the antibodies in an antibody composition are directed to or bind to the same antigen or epitope.

The "average amount of sialic acid residues per carbohydrate chain" according to the invention in particular refers to the number of sialic acid residues which are on average present in a carbohydrate chain of a group of carbohydrate chains. In particular, it refers to the total number of sialic acid residues attached to the carbohydrates of a group of carbohydrate chains divided by the total number of carbohydrate chains in said group. An average amount of sialic acid residues per carbohydrate chain of 1.0 means that in a group of carbohydrate chains, each carbohydrate chain on average comprises 1.0 sialic acid residue. The term "carbohydrate chain" in this respect preferably refers to the carbohydrate chain attached to a polypeptide chain of an antibody. The group of carbohydrate chain preferably refers to all carbohydrate chains of all antibodies present in an antibody composition, or to all carbohydrate chains of all antibodies of a specific type in an antibody composition, or to all carbohydrate chains present in a specific part or at a specific glycosylation site of all antibodies (of a specific type) in an antibody composition.

The term "circulation half-life" preferably refers to the time which elapses after administration of an agent to the circulation of a living body, in particular the human body, until only half of the administered amount of the agent is present in the circulation. In case of therapeutically active agents, a higher circulation half-life in general is desired since then the agent has a longer lasting therapeutic effect. The "clearance rate" preferably refers to the rate at which an agent is removed from the circulation of a living body, in particular the human body. A higher clearance rate thus normally results in a lower circulation half-life.

DETAILED DESCRIPTION OF THE INVENTION

The present invention is based on the findings that—in contrast to the teachings of the prior art—the amount of sialic acid residues in the carbohydrate chains attached to the Fab part of an antibody having a glycosylation site in the Fab part is decisive for the circulation half-life and thus, the bioavailability of said antibody. In particular, a high degree of sialylation of the Fab part results in a high half-life of the antibody in the patient's circulation. Likewise, a lower sialylation degree of the Fab part leads to a lower circulation half-life. However, it was also found that when removing the glycosylation site in the Fab part of an antibody and thereby removing any Fab glycosylation, the circulation half-life of the antibody is comparable to that of an antibody having a moderate to high degree of sialylation of the Fab part. Therefore, the circulation half-life of a poorly sialylated antibody cannot only be increased by increasing the amount of sialic acid, but it can also be increased by removing the glycosylation site in the Fab part of the antibody if a respective glycosylation site is present. Furthermore, the present inventors have surprisingly found that adjusting the sialic acid content in glycosylation of the Fab part does often not affect the antigen binding or antigen specificity of the antibody and furthermore, often also has no negative effect on the downstream biological activities of the antibody, such as its ADCC and CDC activity. In cases where a change in the sialic acid content has a negative influence on antigen binding, the glycosylation site may also be removed in the Fab part to increase the circulation half-life and/or a further glycosylation site may be introduced at another position in the Fab part and the sialic acid content of this newly introduced Fab glycosylation may be adjusted accordingly as is taught herein. A further advantage found by the present inventors is the possibility to increase the sialylation at the Fab glycosylation while at the same time the sialylation at the Fc part is kept at a minimum. Thereby, too, the ADCC and CDC activities of the antibodies are not affected by increasing the sialylation of the Fab part.

Method for Controlling the Circulation Half-Life of an Antibody

In view of these findings, the present invention provides a method for controlling the circulation half-life of an antibody or a functional fragment or derivative thereof in an antibody composition, comprising adjusting in a composition comprising the antibody or functional fragment or derivative thereof the amount of sialic acids in the carbohydrates attached to at least one glycosylation site present in the Fab part of the antibodies or fragments or derivatives thereof and/or removing or introducing one or more glycosylation sites in the Fab part of the antibody or fragment or derivative thereof. Thereby, it is also possible to generate circulation half-lives which are tailor-made with respect to the intended use of the antibody. This provides flexibility for adjusting the circulation half-life of antibodies without the necessity to use chemical modifications (such as PEG or HES) or fusion proteins.

In particular, in a first aspect, the present invention provides a method for controlling the circulation half-life of an antibody or a functional fragment or derivative thereof, comprising the step of (a) for increasing the circulation half-life
  (a1) increasing in a composition comprising the antibody or functional fragment or derivative thereof the amount of sialic acids in the carbohydrates attached to at least one glycosylation site present in the Fab part of the antibodies or fragments or derivatives thereof; and/or
  (a2) removing one or more glycosylation sites present in the Fab part of the antibody or fragment or derivative thereof; and/or
  (a3) decreasing in a composition comprising the antibody or functional fragment or derivative thereof the amount of free galactose units in the carbohydrates attached to at least one glycosylation site present in the Fab part of the antibodies or fragments or derivatives thereof; or
(b) for decreasing the circulation half-life
  (b1) decreasing in a composition comprising the antibody or functional fragment or derivative thereof the amount of sialic acids in the carbohydrates attached to at least one glycosylation site present in the Fab part of the antibodies or fragments or derivatives thereof; and/or
  (b2) introducing one or more glycosylation sites into the Fab part of the antibody or fragment or derivative thereof; and/or
  (b3) increasing in a composition comprising the antibody or functional fragment or derivative thereof the amount of free galactose units in the carbohydrates attached to at least one glycosylation site present in the Fab part of the antibodies or fragments or derivatives thereof.

Thus, when using the method according to the present invention, it is possible to individually control the circulation half-life of a given antibody by adjusting the sialylation degree and/or the degree of free galactose units on already present or artificially introduced glycosylation sites in the Fab part of the antibody and/or by removing or introducing glycosylation sites in the Fab part.

The sialic acids in the carbohydrate chains of the antibodies are attached to galactose units at the non-reducing end(s) of the carbohydrate structure. Thus, an increase in the amount of sialic acids also results in a decrease in the amount of free galactose units and vice versa. Increasing and decreasing the amount of free galactose units can for example be achieved by decreasing or increasing the amount of sialic acid, respectively. However, the amount of free galactose units may also be decreased by attaching other residues to the free galactose units, for example acetyl residues, glucuronic acids or sulfates, and/or by removing free galactose units from the carbohydrates. Likewise, increasing the amount of free galactose units may be achieved by decreasing the amount of sialic acids and/or attaching further galactose units to carbohydrates which are not fully galactosylated.

Increasing the Circulation Half-Life

For increasing the circulation half-life of an antibody or fragment or derivative thereof according to the present invention, the amount of sialic acids in the carbohydrates attached to one or more glycosylation sites in the Fab part of the antibodies or fragments or derivatives thereof comprised in the composition may be increased.

In preferred embodiments, the amount of sialic acids is increased so that in the composition at least 50% of the carbohydrates attached to the at least one glycosylation site present in the Fab part comprise at least one sialic acid residue. Preferably, in the composition at least 60%, more preferably at least 65%, at least 68%, at least 70% or most preferably at least 75% of the carbohydrates attached to the one or more glycosylation sites in the Fab part comprise at least one sialic acid residue. In certain embodiments, the amount of sialic acids is increased so that in the composition at least 20% of the carbohydrates attached to the at least one glycosylation site present in the Fab part comprise at least two sialic acid residues.

Preferably, in the composition at least 25%, more preferably at least 30%, at least 35%, at least 40% or most preferably at least 45% of the carbohydrates attached to the one or more glycosylation sites in the Fab part comprise at least two sialic acid residues.

Preferably, the amount of sialic acids is increased so that in the composition the relative amount of carbohydrates attached to the at least one glycosylation site present in the Fab part which comprise at least one sialic acid residue is increase by at least 5 percentage points, more preferably by at least 7 percentage points, at least 10 percentage points, at least 15 percentage points, at least 20 percentage points, at least 25 percentage points, at least 30 percentage points, at least 35 percentage points, at least 40 percentage points, at least 45 percentage points, or at least 50 percentage points. The relative amount of carbohydrates attached to the at least one glycosylation site present in the Fab part which comprise at least one sialic acid residue in the composition is the percentage of carbohydrates comprising at least one sialic acid residue of all carbohydrates attached to the at least one glycosylation site present in the Fab part in the composition. An increase by 10 percentage points, for example, refers to an embodiment wherein the percentage value of the relative amount of carbohydrates attached to the at least one glycosylation site present in the Fab part which comprise at least one sialic acid residue in the composition is increased by 10 in step (a1), i.e. prior to step (a1), the relative amount is X % and after step (a1), the relative amount is (X+10) %. in the composition comprising the antibody or functional fragment or derivative thereof the amount of sialic acids in the carbohydrates attached to the at least one glycosylation site present in the Fab part of the antibody or fragment or derivative thereof is increased by at least 5 percentage points. Preferably, in the composition at least 60%, more preferably at least 65%, at least 68%, at least 70% or most preferably at least 75% of the carbohydrates attached to the one or more glycosylation sites in the Fab part comprise at least one sialic acid residue.

An increase in the amount of sialic acids in the carbohydrates attached to the at least one glycosylation site present in the Fab part also includes increasing the number of sialic acids in carbohydrates attached to the at least one glycosylation site present in the Fab part of the antibodies or fragments or derivatives thereof in the composition which already comprise at least one sialic acid residue. In particular, the increase in the amount of sialic acids according to step (a1) of the method according to the present invention preferably refers to an increase in the average amount of sialic acid residues per carbohydrate chain in the carbohydrates attached to the at least one glycosylation site present in the Fab part of the antibodies or fragments or derivatives thereof in the composition. Preferably, said average amount of sialic acid residues per carbohydrate chain is increased by at least 0.01, more preferably by at least 0.05, at least 0.1, at least 0.15, at least 0.2, at least 0.3 or most preferably by at least 0.5. In preferred embodiments, the amount of sialic acids is increased so that the average amount of sialic acid residues per carbohydrate chain in the carbohydrates attached to the at least one glycosylation site present in the Fab part of the antibodies or fragments or derivatives thereof in the composition is at least 0.5, preferably at least 0.6, at least 0.7, at least 0.8, at least 0.9, at least 1.0, at least 1.05 or at least 1.1.

The one or more glycosylation sites in the Fab part may have been present in the antibody prior to the step of increasing its circulation half-life or one or more of these glycosylation sites may have been introduced into the Fab part of the antibody as part of the method according to the present invention. Thus, the step of increasing the amount of sialic acid in the carbohydrates attached to one or more glycosylation sites in the Fab part of the antibody or fragment or derivative thereof may in certain embodiments include the step of introducing one or more glycosylation sites into the Fab part. These newly introduced glycosylation sites, when glycosylated, preferably carry carbohydrates wherein at least 50%, more preferably at least 60%, at least 65%, at least 68%, at least 70% or most preferably at least 75% of said carbohydrates in the composition comprise at least one sialic acid residue. The introduction of a glycosylation site into the Fab part of the antibody or fragment or derivative thereof is described in more details below.

In certain embodiments, the amount of sialic acids in the carbohydrates attached to the one or more glycosylation sites in the Fab part is increased without significantly increasing the amount of sialic acids in the carbohydrates attached to one or more glycosylation sites in the Fc part of the antibody or fragment or derivative thereof.

Preferably, the amount of sialic acids in the carbohydrates attached to one or more glycosylation sites in the Fc part of the antibody or fragment or derivative thereof in the composition is less than 20%, more preferably less than 15%, less than 10%, less than 8% or most preferably less than 7% after performing the method according to the present invention. In particular, less than 20%, preferably less than 15%, less than 10% or less than 8%, most preferably less than 7% of the carbohydrates attached to the glycosylation sites in the Fc part of the antibodies comprise one or more sialic acids.

In certain embodiments, the amount of free galactose units is decreased so that in the composition less than 50% of the carbohydrates attached to the at least one glycosylation site present in the Fab part comprise at least two free galactose units. Preferably, in the composition less than 40%, less than 30%, less than 20%, less than 15%, less than 10%, less than 7% or less than 5% of the carbohydrates attached to the one or more glycosylation sites present in the Fab part comprise two or more free galactose units. Furthermore, in the composition preferably less than 95% of the carbohydrates attached to the at least one glycosylation site present in the Fab part comprise at least one free galactose unit. More preferably, in the composition less than 90%, less than 85%, less than 80%, less than 75%, less than 70%, less than 65%, less than 60%, less than 55%, less than 50%, less than 45% or less than 40% of the carbohydrates attached to the one or more glycosylation sites present in the Fab part comprise one or more free galactose units.

Preferably, the amount of free galactose units is decreased so that in the composition the relative amount of carbohydrates attached to the at least one glycosylation site present in the Fab part which comprise at least one free galactose unit, preferably at least two free galactose units, is decrease by at least 5 percentage points, more preferably by at least 7 percentage points, at least 10 percentage points, at least 15 percentage points, at least 20 percentage points, at least 25 percentage points, at least 30 percentage points, at least 35 percentage points, at least 40 percentage points, at least 45 percentage points, or at least 50 percentage points. The relative amount of carbohydrates attached to the at least one glycosylation site present in the Fab part which comprise at least one free galactose unit, preferably at least two free galactose units, in the composition is the percentage of carbohydrates comprising at least one free galactose unit, preferably at least two free galactose units, of all carbohydrates attached to the at least one glycosylation site present in the Fab part in the composition. A decrease by 10 percentage points, for example, refers to an embodiment wherein the percentage value of the relative amount of carbohydrates attached to the at least one glycosylation site present in the Fab part which comprise at least one free galactose unit, preferably at least two free galactose units, in the composition is decreased by 10 in step (a3), i.e. prior to step (a3), the relative amount is X % and after step (a3), the relative amount is (X−10) %.

A decrease in the amount of free galactose units in the carbohydrates attached to the at least one glycosylation site present in the Fab part also includes decreasing the number of free galactose units in carbohydrates attached to the at least one glycosylation site present in the Fab part of the antibodies or fragments or derivatives thereof in the composition which comprise more than one free galactose unit. In particular, the decrease in the amount of free galactose units according to step (a3) of the method according to the present invention preferably refers to a decrease in the average amount of free galactose units per carbohydrate chain in the carbohydrates attached to the at least one glycosylation site present in the Fab part of the antibodies or fragments or derivatives thereof in the composition. Preferably, said average amount of free galactose units per carbohydrate chain is decreased by at least 0.01, more preferably by at least 0.05, at least 0.1, at least 0.15, at least 0.2, at least 0.3 or most preferably by at least 0.5. In preferred embodiments, the amount of free galactose units is decreased so that the average amount of free galactose units per carbohydrate chain in the carbohydrates attached to the at least one glycosylation site present in the Fab part of the antibodies or fragments or derivatives thereof in the composition is less than 1.5, preferably less than 1.4, less than 1.3, less than 1.2, less than 1.1, less than 1.0, preferably less than 0.9, less than 0.8, less than 0.7, less than 0.6 or less than 0.5. Preferably, a decrease in the amount of free galactose units is achieved by increasing the amount of sialic acids.

The increase in the amount of sialic acids and/or the decrease in the amount of free galactose units may be achieved by any known means, including expressing the antibody or fragment or derivative thereof in a cell or cell line having a high sialylation activity. Cell lines having a high sialylation degree can be obtained, for example, by selecting suitable single clones of a cell line or by genetically engineering a cell line. Cell lines having a high sialylation activity can in particular be obtained by mutagenesis screenings of cell lines suitable for expressing antibodies, wherein cell clones having a high sialylation activity are selected for. Furthermore, the expression of enzyme(s) responsible for sialylation of glycoproteins can be induced or enhanced in the cell or cell line, for example by inducing or increasing the expression of endogenous enzyme(s) and/or by introducing exogenous expression cassette(s) for said enzyme(s). Suitable enzymes are, for example, sialyltransferases which are responsible for the transfer of the sialic acid residue to a carbohydtare chain, transporter which control the transport of the sialic acid residue or its precursors to the relevant section or organelle in the cell, or enzymes involved in the biosynthesis of sialic acids. Particular examples are sialyltransferases such as α-2,6- and α-2,3-sialyltransferases, transporters such as the CMP-sialic acid transporter, epimerases such as UDP-N-acetylglucosamine-2-epimerase, kinases such as N-acetylmannosamine kinase and N-acetylglucosamine kinase, N-acetylneuraminic acid-9-P-synthetase, N-acetylneuraminic acid-9-P-phosphatase and CMP-N-acetylneuraminic acid synthetase. Furthermore, culturing conditions during the expression which result in a high sialylation degree can be used. Suitable methods are known in the art and are described, e.g., in WO 2005/080585. Alternatively or additionally, in vitro sialylation can be used, in particular enzymatic sialylation using a sialyltransferase and a suitable substrate, or chemical sialylation using suitable chemical reactants. An exemplary cell line which is capable of providing a high sialylation degree is GT-5s, deposited on Jul. 28, 2010 under the accession number DSM ACC 3078 according to the requirements of the Budapest Treaty at the Deutsche Sammlung von Mikroorganismen und Zellkulturen (DSMZ), Inhoffenstraße 7B, 38124 Braunschweig (DE) by the Glycotope GmbH, Robert-Rössle-Str. 10, 13125 Berlin (DE), or a cell line derived therefrom or a cell line homologous thereto. GT-5s is a cell line derived from K562 cells and has been selected for its high sialylation activity. K562 is a human myeloid leukemia cell line present in the American Type Culture Collection (ATCC CCL-243). GT-5s and cell lines derived therefrom can be cultivated and maintained under the well known conditions suitable for K562.

A cell line which is derived from GT-5s can be for example obtained by randomly or specifically selecting a single clone or a group of cells from a GT-5s culture, optionally after treating the GT-5s cells in order to enhance their mutation rate, or by genetically altering a GT-5s cell line. The selected clone or group of cells may further be treated as described above and/or further rounds of selection may be performed. A cell line which is homologous to GT-5s in particular is an immortalized human myeloid cell line. Preferably, a cell line derived from or homologous to GT-5s is capable of providing antibodies having a glycosylation pattern similar to that obtained from GT-5s. Preferably, antibodies that are produced by a cell line derived from or homologous to GT-5s has one or more of the glycosylation characteristics as described herein, in particular a high sialylation degree, preferably a high sialylation degree at the Fab part. In a preferred embodiment, the cell line derived from or homologous to GT-5s further is capable of producing antibodies having a low degree of fucosylation as described herein, in particular a low degree of fucosylation at their Fc part. The similar glycosylation pattern of antibodies that are produced by the cell line derived from or homologous to GT-5s preferably differs from the glycosylation pattern of antibodies obtained from GT-5s by 20% or less, more preferably 15% or less, 10% or less or 5% or less, in particular in one or more, preferably all of the glycosylation properties selected from the group consisting of the percentage amount of carbohydrates carrying bis-GlcNAc, the percentage amount of sialylated carbohydrates, the percentage amount of carbohydrates carrying a free galactose residue, the percentage amount of 2,6-coupled sialic acids and the percentage amount of carbohydrates carrying fucose. In particularly preferred embodiments, the similar glycosylation properties do not encompass the percentage amount of carbohydrates carrying fucose.

The cell line GT-5s as well as cell lines derived therefrom and cell lines homologous thereto are in particular advantageous since they provide a very stable and homogeneous protein production, in particular with respect to antibodies. They have a very good batch-to-batch consistency, i.e. the produced proteins and their glycosylation pattern are similar when obtained from different production runs or when produced at different scales and/or with different culturing procedures.

Besides the increase of the sialic acid content and/or the decrease of the free galactose unit content in the carbohydrates attached to one or more glycosylation sites in the Fab part of the antibody or fragment or derivative thereof, the circulation half-life of the antibody or fragment or derivative thereof can also be increased by removing one or more glycosylation sites which are present in the Fab part of the antibody or fragment or derivative thereof. By removing said glycosylation site(s), the presence of carbohydrates in the Fab part of the antibodies or fragment or derivative thereof having a low degree of sialylation and/or a high degree of free galactose units is prevented. Since these lowly sialylated carbohydrates are responsible for a fast clearance rate of the antibodies from the patient's circulation, the removal of the respective glycosylation site(s) in the Fab part of the antibody increases its circulation half-life.

In preferred embodiments, the removal of a glycosylation site is done by genetic engineering of the nucleic acid coding for the antibody or fragment or derivative thereof. In particular, the glycosylation site is removed by altering the nucleic acid sequence coding for the antibody or fragment or derivative thereof. Preferably one or more of the codons coding for the amino acids of the glycosylation site are mutated so that at least one amino acid substitution, addition or deletion in the glycosylation site is achieved. In particular, the amino acid to which the carbohydrate chain is attached is deleted or substituted, preferably by an amino acid which cannot function as a carbohydrate acceptor. Alternatively or additionally, also another amino acid of the glycosylation site can be substituted or deleted, or one or more further amino acids can be added into the glycosylation site, so that the altered amino acid sequence does not function as recognition site for enzymatic glycosylation.

The antibody or fragment or derivative thereof from which one or more glycosylation sites in the Fab part are to be removed may have any number of glycosylation sites in the Fab part, such as only one glycosylation site, at least two glycosylation sites or at least three glycosylation sites in the Fab part. Not all glycosylation sites in the Fab part of the antibody or fragment or derivative thereof have to be removed in the method according to the present invention. However, preferably all glycosylation sites present in the Fab part of the antibody or fragment or derivative thereof are removed for maximum increase of the circulation half-life.

Decreasing the Circulation Half-Life

For decreasing the circulation half-life of an antibody or fragment or derivative thereof according to the present invention, the amount of sialic acids in the carbohydrates attached to one or more glycosylation sites in the Fab part of the antibody or fragment or derivative thereof present in the composition may be decreased.

In preferred embodiments, the amount of sialic acids is decreased so that in the composition less than 50% of the carbohydrates attached to the at least one glycosylation site present in the Fab part comprise at least one sialic acid residue. Preferably, in the composition less than 40%, less than 30%, less than 20%, less than 15%, less than 10%, less than 7%, less than 5%, less than 3%, less than 2% or less than 1% of the carbohydrates attached to the one or more glycosylation sites present in the Fab part comprise one or more sialic acid residues. According to one embodiments, the amount of sialic acids is decreased so that in the composition about 0% of the carbohydrates attached to the at least one glycosylation site present in the Fab part comprise at least one sialic acid residue. In certain embodiments, the amount of sialic acids is decreased so that in the composition less than 30% of the carbohydrates attached to the at least one glycosylation site present in the Fab part comprise at least two sialic acid residues. Preferably, in the composition less than 25%, less than 20%, less than 15%, less than 10%, less than 7%, less than 5%, less than 3%, less than 2% or less than 1%, more preferably about 0% of the carbohydrates attached to the one or more glycosylation sites present in the Fab part comprise two or more sialic acid residues.

Preferably, the amount of sialic acids is decreased so that in the composition the relative amount of carbohydrates attached to the at least one glycosylation site present in the Fab part which comprise at least one sialic acid residue is decreased by at least 5 percentage points, more preferably by at least 7 percentage points, at least 10 percentage points, at least 15 percentage points, at least 20 percentage points, at least 25 percentage points, at least 30 percentage points, at least 35 percentage points, at least 40 percentage points, at least 45 percentage points, or at least 50 percentage points. The relative amount of carbohydrates attached to the at least one glycosylation site present in the Fab part which comprise at least one sialic acid residue in the composition is the percentage of carbohydrates comprising at least one sialic acid residue of all carbohydrates attached to the at least one glycosylation site present in the Fab part in the composition. A decrease by 10 percentage points, for example, refers to an embodiment wherein the percentage value of the relative amount of carbohydrates attached to the at least one glycosylation site present in the Fab part which comprise at least one sialic acid residue in the composition is decreased by 10 in step (b1), i.e. prior to step (b1), the relative amount is X % and after step (b1), the relative amount is (X−10) %.

A decrease in the amount of sialic acids in the carbohydrates attached to the at least one glycosylation site present in the Fab part also includes decreasing the number of sialic acids in carbohydrates attached to the at least one glycosylation site present in the Fab part of the antibodies or fragments or derivatives thereof in the composition which comprise more than one sialic acid residue. In particular, the decrease in the amount of sialic acids according to step (b1) of the method according to the present invention preferably refers to a decrease in the average amount of sialic acid residues per carbohydrate chain in the carbohydrates attached to the at least one glycosylation site present in the Fab part of the antibodies or fragments or derivatives thereof in the composition. Preferably, said average amount of sialic acid residues per carbohydrate chain is decreased by at least 0.01, more preferably by at least 0.05, at least 0.1, at least 0.15, at least 0.2, at least 0.3 or most preferably by at least 0.5. In preferred embodiments, the amount of sialic acids is decreased so that the average amount of sialic acid residues per carbohydrate chain in the carbohydrates attached to the at least one glycosylation site present in the Fab part of the antibodies or fragments or derivatives thereof in the composition is less than 0.8, preferably less than 0.7, less than 0.6, less than 0.5, less than 0.4, less than 0.3, less than 0.2, less than 0.1 or less than 0.05.

In certain embodiments, the amount of free galactose units is increased so that in the composition at least 50% of the carbohydrates attached to the at least one glycosylation site present in the Fab part comprise at least one free galactose unit, preferably at least two free galactose units. Preferably, in the composition at least 60%, more preferably at least 70%, at least 80%, at least 85%, at least 90%, at least 95%, at least 97% or most preferably at least 98% of the carbohydrates attached to the one or more glycosylation sites in the Fab part comprise at least one free galactose unit, preferably at least two free galactose units.

Preferably, the amount of free galactose units is increased so that in the composition the relative amount of carbohydrates attached to the at least one glycosylation site present in the Fab part which comprise at least one free galactose unit, preferably at least two free galactose units, is increase by at least 5 percentage points, more preferably by at least 7 percentage points, at least 10 percentage points, at least 15 percentage points, at least 20 percentage points, at least 25 percentage points, at least 30 percentage points, at least 35 percentage points, at least 40 percentage points, at least 45 percentage points, or at least 50 percentage points. The relative amount of carbohydrates attached to the at least one glycosylation site present in the Fab part which comprise at least one free galactose unit, preferably at least two free galactose units, in the composition is the percentage of carbohydrates comprising at least one free galactose unit, preferably at least two free galactose units, of all carbohydrates attached to the at least one glycosylation site present in the Fab part in the composition. An increase by 10 percentage points, for example, refers to an embodiment wherein the percentage value of the relative amount of carbohydrates attached to the at least one glycosylation site present in the Fab part which comprise at least one free galactose unit, preferably at least two free galactose units, in the composition is increased by 10 in step (b3), i.e. prior to step (b3), the relative amount is X % and after step (b3), the relative amount is (X+10) %.

An increase in the amount of free galactose units in the carbohydrates attached to the at least one glycosylation site present in the Fab part also includes increasing the number of free galactose units in carbohydrates attached to the at least one glycosylation site present in the Fab part of the antibodies or fragments or derivatives thereof acid in the composition which already comprise at least one free galactose unit. In particular, the increase in the amount of free galactose units according to step (b3) of the method according to the present invention preferably refers to an increase in the average amount of free galactose units per carbohydrate chain in the carbohydrates attached to the at least one glycosylation site present in the Fab part of the antibodies or fragments or derivatives thereof in the composition. Preferably, said average amount of free galactose units per carbohydrate chain is increased by at least 0.01, more preferably by at least 0.05, at least 0.1, at least 0.15, at least 0.2, at least 0.3 or most preferably by at least 0.5. In preferred embodiments, the amount of free galactose units is increased so that the average amount of free galactose units per carbohydrate chain in the carbohydrates attached to the at least one glycosylation site present in the Fab part of the antibodies or fragments or derivatives thereof in the composition is at least 0.5, preferably at least 0.6, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9 or at least 1.95.

The one or more glycosylation sites in the Fab part may have been present in the antibody prior to the step of increasing its circulation half-life or one or more of these glycosylation sites may have been introduced into the Fab part of the antibody as part of the method according to the present invention. Thus, the step of increasing the amount of free galactose units in the carbohydrates attached to one or more glycosylation sites in the Fab part of the antibody or fragment or derivative thereof may in certain embodiments include the step of introducing one or more glycosylation sites into the Fab part. These newly introduced glycosylation sites, when glycosylated, preferably carry carbohydrates wherein at least 50%, more preferably at least 60%, at least 70%, at least 80%, at least 85%, at least 90%, at least 95%, at least 97% or most preferably at least 98% of said carbohydrates in the composition comprise at least one free galactose unit, preferably at least two free galactose units. The introduction of a glycosylation site into the Fab part of the antibody or fragment or derivative thereof is described in more details below.

The decrease in the amount of sialic acids and/or the increase in the amount of free galactose units may be achieved by any known means, including expressing the antibody or fragment or derivative thereof in a cell or cell line having low or no sialylation activity. Cell lines having a low or no sialylation degree can be obtained, for example, by selecting suitable single clones of a cell line, by genetically engineering a cell line, e.g. introducing one or more mutations into the genome of the cell line, or by a knock-out or knock-down of or RNA interference against one or more genes involved in the sialylation pathway of a cell line. Suitable genes involved in the sialylation pathway for example code for sialyltransferases which are responsible for the transfer of the sialic acid residue to a carbohydrate chain, transporter which control the transport of the sialic acid residue or its precursors to the relevant section or organelle in the cell, or enzymes involved in the biosynthesis of sialic acids. Particular examples are sialyltransferases such as $\alpha$-2,6- and $\alpha$-2,3-sialyltransferases, transporters such as the CMP-sialic acid transporter, epimerases such as UDP-N-acetylglucosamine-2-epimerase, kinases such as N-acetylmannosamine kinase and N-acetylglucosamine kinase, N-acetylneuraminic acid-9-P-synthetase, N-acetylneuraminic acid-9-P-phosphatase and CMP-N-acetylneuraminic acid synthetase. Furthermore, culturing conditions during the expression which result in a low sialylation degree can be used. Alternatively or additionally, in vitro de-sialylation can be used, in particular enzymatic de-sialylation using a sialylase, or chemical de-sialylation using suitable chemical reactants. Suitable cell lines and methods for providing glycoproteins having a specifically adjusted sialic acid content, in particular a low content of sialic acids, are described, for example, in WO 2005/080585.

Besides the decrease of the sialic acid content and/or the increase of the free galactose unit content in the carbohydrates attached to one or more glycosylation sites in the Fab part of the antibody or fragment or derivative thereof, the circulation half-life of the antibody or fragment or derivative thereof can also be decreased by introducing one or more glycosylation sites into the Fab part of the antibody or fragment or derivative thereof. By introducing said glycosylation site(s), the presence of carbohydrates having a low degree of sialylation in the antibodies or fragment or derivative thereof can be increased. These newly introduced glycosylation sites, when glycosylated, preferably carry carbohydrates wherein less than 50%, more preferably less than 40%, less than 30%, less than 20%, less than 15%, less than 10%, less than 7% or most preferably less than 5% of said carbohydrates in the composition comprise one or more sialic acid residues. Likewise, these newly introduced glycosylation sites, when glycosylated, preferably carry carbohydrates wherein at least 50%, more preferably at least 60%, at least 70%, at least 80%, at least 85%, at least 90%, at least 95%, at least 97% or most preferably at least 98% of said carbohydrates in the composition comprise at least one free galactose unit, preferably at least two free galactose units. How a respective low amount of sialylation can be achieved is described above.

Preferably, at least one, more preferably at least two or at least three glycosylation sites are introduced into the Fab part of the antibody or fragment or derivative thereof. In certain embodiments, one, two or three glycosylation sites are introduced. The glycosylation site(s) may be introduced by any means known in the art. The introduction of a glycosylation site preferably is done by genetic engineering of the nucleic acid coding for the antibody or fragment or derivative thereof. In particular, the glycosylation site is introduced by altering the nucleic acid sequence coding for the antibody or fragment or derivative thereof. Preferably one or more of the codons of the antibody are mutated so that the encoded amino acids form a glycosylation site. Introduction of the glycosylation site may be achieved by addition of one ore more further codons, resulting in one or more additional amino acids, by substitution of one or more nucleotides, resulting in the substitution of one or more amino acids, and/or by deletion of one or more codons, resulting in the deletion of one or more amino acids. In particular, the glycosylation site(s) is(are) introduced into the heavy chain variable region or the light chain variable region of the antibody or fragment or derivative thereof, preferably in the heavy chain variable region. More preferably, the glycosylation site is introduced into the framework regions of a variable region. However, the glycosylation site may also be introduced into the constant regions of the Fab part, in particular the heavy chain constant region 1.

When introducing one or more glycosylation sites into the Fab part of the antibody or fragment or derivative thereof, the antibody or fragment or derivative thereof preferably does not originally contain a glycosylation sites in its Fab part. However, in certain embodiments the antibody or fragment or derivative thereof already comprises one or more glycosylation sites in its Fab part and one or more additional glycosylation sites are introduced by the method according to the present invention. The newly introduced glycosylation site(s) preferably carry carbohydrates wherein less than 50%, more preferably less than 40%, less than 30%, less than 20%, less than 15%, less than 10%, less than 7% or most preferably less than 5% of said carbohydrates in the composition comprise one or more sialic acid residues. In particular, in the composition less than 50%, preferably less than 40%, less than 30%, less than 20%, less than 15%, less than 10%, less than 7% or most preferably less than 5% of the carbohydrates attached to all glycosylation sites present in the Fab part of the antibodies or fragments or derivatives thereof preferably comprise one or more sialic acid residues. Likewise, these newly introduced glycosylation site(s), when glycosylated, preferably carry carbohydrates wherein at least 50%, more preferably at least 60%, at least 70%, at least 80%, at least 85%, at least 90%, at least 95%, at least 97% or most preferably at least 98% of said carbohydrates in the composition comprise at least one free galactose unit, preferably at least two free galactose units. In particular, in the composition at least 50%, more preferably at least 60%, at least 70%, at least 80%, at least 85%, at least 90%, at least 95%, at least 97% or most preferably at least 98% of the carbohydrates attached to all glycosylation sites present in the Fab part of the antibodies or fragments or derivatives thereof preferably comprise at least one free galactose unit, preferably at least two free galactose units. How a respective low amount of sialylation can be achieved is described above.

The Fab Glycosylation Sites

The one or more glycosylation sites which are present in the Fab part or which are to be introduced into or removed from the Fab part of the antibody or fragment or derivative thereto preferably are N-glycosylation sites and/or O-glycosylation sites, preferably N-glycosylation sites, more preferably N-glycosylation sites having the amino acid sequence Asn Xaa Ser/Thr, wherein Xaa is any amino acid preferably except Pro. They may be positioned anywhere in the Fab part of the antibody or fragment or derivative thereof. However, they are preferably in the heavy chain variable region or the light chain variable region, more preferably in the heavy chain variable region. In particular, they may be in the framework regions and/or the CDRs of the heavy and/or light chain variable regions, preferably in the framework regions. However, the one or more glycosylation sites may also be positioned in the constant regions of the Fab part, in particular the heavy chain constant region 1.

Introduction and removal of a glycosylation site in the Fab part can be achieved by altering the amino acid sequence of the Fab part, in particular by addition, substitution and/or deletion of one or more amino acid residues. This may preferably be done by genetic engineering of the nucleic acid coding for the amino acids or fragments or derivatives thereof, in particular by mutagenesis of the nucleic acid sequence. Suitable methods for removing or introduction of a glycosylation site are described above.

Preferably, in embodiments wherein the antibody or fragment or derivative thereof comprises two or more heavy chain variable regions, a glycosylation site present in the heavy chain variable region is present in all heavy chain variable regions of the antibody or fragment or derivative thereof. Preferably, in embodiments wherein the antibody or fragment or derivative thereof comprises two or more heavy chain constant regions, in particular two or more CH1 regions, a glycosylation site present in the heavy chain constant region 1 is present in all heavy chain constant regions 1 of the antibody or fragment or derivative thereof. Preferably, in embodiments wherein the antibody or fragment or derivative thereof comprises two or more light chain variable regions, a glycosylation site present in the light chain variable region is present in all light chain variable regions of the antibody or fragment or derivative thereof. Preferably, in embodiments wherein the antibody or fragment or derivative thereof comprises two or more light chain constant regions, a glycosylation site present in the light chain constant region is present in all light chain constant regions of the antibody or fragment or derivative thereof.

Approximately 30% of the antibodies isolated from human serum have a glycosylation site within the Fab part. With respect to anti-EGFR antibodies, in particular Cetuximab, one glycosylation site in the Fab part of these antibodies preferably is positioned in framework region 3 of the heavy chain variable region, more preferably at amino acid position 85 according to the Kabat numbering. Regarding anti-Muc1 antibodies, in particular Pankomab, one glycosylation site in the Fab part of these antibodies preferably is positioned in CDR2 of the heavy chain variable region, more preferably at amino acid position 54 according to the Kabat numbering.

If at least one glycosylation site is present in the Fab part of the antibody or fragment or derivative thereof, at least one antibody or fragment or derivative thereof in the composition is glycosylated at the Fab part. Preferably, at least 25%, more preferably at least 40%, at least 50%, at least 60%, at least 70%, at least 75%, at least 80%, at least 85%, at least 90%, at least 95%, at least 97%, at least 98%, at least 99% or most preferably about 100% of the antibodies or fragments or derivatives thereof in the composition are glycosylated at the Fab part. Furthermore, preferably at least 25%, more preferably at least 40%, at least 50%, at least 60%, at least 70%, at least 75%, at least 80%, at least 85%, at least 90%, at least 95%, at least 97%, at least 98%, at least 99% or most preferably about 100% of the antibodies or fragments or derivatives thereof in the composition are glycosylated at a specific glycosylation site in the Fab part as described herein, preferably at all glycosylation sites in the Fab part. Higher degrees of respectively glycosylated antibodies may also be obtained, e.g., by enrichment methods, e.g. after or during the purification process.

In preferred embodiments, the introduction or removal of one or more glycosylation sites in the Fab part of the antibody or fragment or derivative thereof does not inhibit antigen binding and/or antigen specificity of the antibody or fragment or derivative thereof. Preferably, antigen binding and/or antigen specificity are not significantly reduced by introducing or removing one or more glycosylation sites in the Fab part. Likewise, also the increase or decrease of the amount of sialic acid in the carbohydrates attached to the one or more glycosylation sites in the Fab part of the antibody or fragment or derivative thereof preferably does not inhibit antigen binding and/or antigen specificity, and more preferably does not significantly reduce antigen binding and/or antigen specificity. In particular, after performing the method according to the present invention, the binding affinity of the antigen or fragment or derivative thereof having an increased or decreased circulation half-life to its specific antigen is at least 0.1%, at least 0.5%, at least 1%, at least 5% at least 10%, preferably at least 25%, at least 50%, at least 60%, at least 75%, at least 80%, at least 85%, at least 90% or at least 95% of the binding affinity of the antigen or fragment or derivative thereof prior to controlling its circulation half-life.

However, in case the increase or decrease of the amount of sialic acids in the carbohydrates attached to a specific glycosylation site in the Fab part of the antibody or fragment or derivative thereof negatively affects or is at risk of negatively affecting the antigen binding or antigen specificity, said glycosylation site may be removed from the antibody and/or one or more other glycosylation sites may be introduced into the Fab part at positions which do not or to a lesser extent influence antigen binding and/or antigen specificity. Then the sialic acid content of the carbohydrates attached to the newly introduced glycosylation site(s) can be increased or decreased for controlling the circulation half-life, as desired. Preferably, said newly introduced glycosylation site(s) is(are) positioned in the framework regions of the variable regions or, more preferably, in the constant regions of the Fab part, such as the heavy chain constant region 1 and/or the light chain constant region.

The Antibody or Fragment or Derivative Thereof

The antibody used in the method according to the present invention may be any antibody, including naturally occurring antibodies, polyclonal or monoclonal antibodies, engineered antibodies, chimeric antibodies or humanized antibodies. It may be a human, mouse, rat, goat, primate or camel antibody. Preferably, the antibody is a human, chimeric or humanized antibody. It may be of any antibody class, including IgG, IgE, IgA, IgD and IgM antibodies, and any subclass, including IgG1, IgG2, IgG3, IgG4, IgA1 and IgA2. Preferably, the antibody is an IgG antibody, more preferably an IgG1 or IgG2 antibody, most preferably an IgG1 antibody.

For example, the antibody may be selected from the group consisting of anti-EGFR-antibodies such as Cetuximab, anti-TF antibodies such as Karomab, anti-Muc1 antibodies such as Pankomab, anti-HER2 antibodies such as Trastuzumab, anti-CD20 antibodies such as Rituximab, anti-Aβ antibodies such as Solanezumab, anti-CD52 antibodies such as Alemtuzumab, and chimeric or humanized versions thereof.

Preferred anti-EGFR antibodies are described in WO 96/40210 (describing in particular humanized and chimeric versions of the antibody 225) and U.S. Pat. No. 4,943,533 describing the murine antibody 225 and/or comprise one or more of the CDRs selected from the group consisting of CDRH1 having the amino acid sequence of SEQ ID NO: 1, CDRH2 having the amino acid sequence of SEQ ID NO: 2, CDRH3 having the amino acid sequence of SEQ ID NO: 3, CDRL1 having the amino acid sequence of SEQ ID NO: 4, CDRL2 having the amino acid sequence of SEQ ID NO: 5, CDRL3 having the amino acid sequence of SEQ ID NO: 6. In particular, the antibody may be a chimeric or humanized anti-EGFR-antibody comprising (i) a heavy chain variable region comprising a CDRH1 having the amino acid sequence of SEQ ID NO: 1, a CDRH2 having the amino acid sequence of SEQ ID NO: 2 and a CDRH3 having the amino acid sequence of SEQ ID NO: 3;

(ii) optionally a light chain variable region comprising a CDRL1 having the amino acid sequence of SEQ ID NO: 4, a CDRL2 having the amino acid sequence of SEQ ID NO: 5 and a CDRL3 having the amino acid sequence of SEQ ID NO: 6;

(iii) a glycosylation site present in the Fab part at amino acid position 85 of the heavy chain variable region according to the Kabat numbering; and (iv) optionally a glycosylation site present in the Fc part at amino acid position 297 of the heavy chain constant region 2.

Said antibody preferably is capable of binding the same antigen, in particular the same epitope as Cetuximab and/or the antibody 225.

Preferred anti-Muc1 antibodies are described in the patent applications WO 04/065423 and EP 09 009 942.5, herein incorporated by reference, and/or comprise one or more of the CDRs selected from the group consisting of CDRH1 having the amino acid sequence of SEQ ID NO: 7, CDRH2 having the amino acid sequence of SEQ ID NO: 8, CDRH3 having the amino acid sequence of SEQ ID NO: 9, CDRL1 having the amino acid sequence of SEQ ID NO: 10, CDRL2 having the amino acid sequence of SEQ ID NO: 11, CDRL3 having the amino acid sequence of SEQ ID NO: 12. In particular, the antibody may be a chimeric or humanized anti-TA-Muc1-antibody comprising (i) a heavy chain variable region comprising a CDRH1 having the amino acid sequence of SEQ ID NO: 7, a CDRH2 having the amino acid sequence of SEQ ID NO: 8 and a CDRH3 having the amino acid sequence of SEQ ID NO: 9;

(ii) optionally a light chain variable region comprising a CDRL1 having the amino acid sequence of SEQ ID NO: 10, a CDRL2 having the amino acid sequence of SEQ ID NO: 11 and a CDRL3 having the amino acid sequence of SEQ ID NO: 12;

(iii) a glycosylation site present in the Fab part at amino acid position 54 of the heavy chain variable region according to the Kabat numbering; and (iv) optionally a glycosylation site present in the Fc part at amino acid position 297 of the heavy chain constant region 2.

Said antibody preferably is capable of binding the same antigen, in particular the same epitope as Pankomab. In particular, the chimeric or humanized anti-TA-Muc1-antibody is capable of specifically binding an epitope comprising the amino acid sequence PDTR (SEQ ID NO: 13) or, more preferably PDTRP (SEQ ID NO: 14). The binding to this epitope preferably is glycosylation dependent, wherein in particular the binding is increased if a carbohydrate moiety is attached to the threonine residue of the sequence PDTR or PDTRP, respectively. Preferably, the binding is increased if the epitope is glycosylated at the threonine residue with a carbohydrate moiety selected from the group consisting of N-acetylgalactosamine (Tn), sialyl α2-6 N-acetylgalactosamine (sTn), galactose β1-3 N-acetylgalactosamine (TF) and galactose β1-3 (sialyl α2-6) N-acetylgalactosamine (sTF), preferably with Tn or TF. Preferably, the carbohydrate moiety is bound to the threonine residue by an α-O-glycosidic bond. In some embodiments, the glycosylation dependency of the binding is due to the specific conformation the epitope adopts when glycosylated, in particular by the specific carbohydrate moieties mentioned above. In this case, the antibody does not necessarily have to bind to the carbohydrate moiety but may only bind to the peptide moiety of the epitope wherein the affinity of this binding depends on the conformation of the epitope. Preferably, the epitope is comprised in the extracellular tandem repeats of the mucin protein Muc1. In particular, the antibody according to the invention is capable of binding to a tumor-associated mucin epitope, in particular a tumor-associated Muc1 epitope such as epitope TA-Muc1 (see Karsten, U. et al. (2004) Glycobiology 14, 681-692 and Danielczyk, A. et al. (2006) Cancer Immunol. Immunother. 55, 1337-1347). The tumor-associated mucin 1 epitope TA-Muc1 preferably refers to an epitope of Muc1 which is present on tumor cells but not on normal cells and/or which is only accessible by antibodies in the host's circulation when present on tumor cells but not when present on normal cells.

Preferred anti-CD52 antibodies comprise one or more of the CDRs selected from the group consisting of CDRH1 having the amino acid sequence of SEQ ID NO: 15, CDRH2 having the amino acid sequence of SEQ ID NO: 16, CDRH3 having the amino acid sequence of SEQ ID NO: 17, CDRL1 having the amino acid sequence of SEQ ID NO: 18, CDRL2 having the amino acid sequence of SEQ ID NO: 19, CDRL3 having the amino acid sequence of SEQ ID NO: 20. In particular, the antibody may be an anti-CD52-antibody comprising (i) a heavy chain variable region comprising a CDRH1 having the amino acid sequence of SEQ ID NO: 15, a CDRH2 having the amino acid sequence of SEQ ID NO: 16 and a CDRH3 having the amino acid sequence of SEQ ID NO: 17;
(ii) optionally a light chain variable region comprising a CDRL1 having the amino acid sequence of SEQ ID NO: 18, a CDRL2 having the amino acid sequence of SEQ ID NO: 19 and a CDRL3 having the amino acid sequence of SEQ ID NO: 20;
(iii) a glycosylation site present in the Fab part at amino acid position 60 of the heavy chain variable region according to the Kabat numbering; and
(iv) optionally a glycosylation site present in the Fc part at amino acid position 297 of the heavy chain constant region 2.

Said antibody preferably is capable of binding the same antigen, in particular the same epitope as Alemtuzumab.

Preferred anti-Aβ antibodies comprise one or more of the CDRs selected from the group consisting of CDRH1 having the amino acid sequence of SEQ ID NO: 21, CDRH2 having the amino acid sequence of SEQ ID NO: 22, CDRH3 having the amino acid sequence of SEQ ID NO: 23, CDRL1 having the amino acid sequence of SEQ ID NO: 24, CDRL2 having the amino acid sequence of SEQ ID NO: 25, CDRL3 having the amino acid sequence of SEQ ID NO: 26. In particular, the antibody may be an anti-Aβ antibody comprising
(i) a heavy chain variable region comprising a CDRH1 having the amino acid sequence of SEQ ID NO: 21, a CDRH2 having the amino acid sequence of SEQ ID NO: 22 and a CDRH3 having the amino acid sequence of SEQ ID NO: 23;
(ii) optionally a light chain variable region comprising a CDRL1 having the amino acid sequence of SEQ ID NO: 24, a CDRL2 having the amino acid sequence of SEQ ID NO: 25 and a CDRL3 having the amino acid sequence of SEQ ID NO: 26;
(iii) a glycosylation site present in the Fab part at amino acid position 55 of the heavy chain variable region according to the Kabat numbering; and
(iv) optionally a glycosylation site present in the Fc part at amino acid position 297 of the heavy chain constant region 2.

Said antibody preferably is capable of binding the same antigen, in particular the same epitope as Solanezumab.

In addition to the one or more glycosylation sites in the Fab part, the antibody may also comprise one or more glycosylation sites in the Fc part. Preferably, it comprises the naturally occurring glycosylation sites of the Fc part. For example, it may comprise a glycosylation site in the CH2 region, in particular at Asn297 in case of IgG antibodies. In these embodiments, preferably at least one antibody or fragment or derivative thereof in the composition is glycosylated at the Fc part. Preferably, at least 25%, more preferably at least 40%, at least 50%, at least 60%, at least 70%, at least 75%, at least 80%, at least 85%, at least 90%, at least 95%, at least 97%, at least 98%, at least 99% and most preferably about 100% of the antibodies or fragments or derivatives thereof in the composition are glycosylated at the Fc part.

The fragment or derivative of the antibody preferably comprises at least the heavy chain variable region of the antibody. Preferably, it further comprises the heavy chain constant region 1 of the antibody, and/or the light chain variable region of the antibody and/or the light chain constant region of the antibody. In a preferred embodiment, the fragment or derivative of the antibody comprises the entire Fab part of the antibody.

In particular, the fragment or derivative of the antibody is selected from the group consisting of:
(i) Fab fragments, monovalent fragments consisting of the variable region and the first constant domain of each the heavy and the light chain;
(ii) F(ab)$_2$ fragments, bivalent fragments comprising two Fab fragments linked by a disulfide bridge at the hinge region;
(iii) Fd fragments consisting of the variable region and the first constant domain CH1 of the heavy chain;
(iv) Fv fragments consisting of the heavy chain and light chain variable region of a single arm of an antibody;
(v) scFv fragments, Fv fragments consisting of a single polypeptide chain;
(vi) (Fv)$_2$ fragments consisting of two Fv fragments covalently linked together;
(vii) a heavy chain variable domain; and
(viii) multibodies consisting of a heavy chain variable region and a light chain variable region covalently linked together in such a manner that association of the heavy chain and light chain variable regions can only occur intermolecular but not intramolecular.

The fragment or derivative preferably is capable of binding to the same antigen, preferably the same epitope, as the antibody.

The Glycosylation Pattern

In preferred embodiments, the antibody or fragment or derivative thereof which circulation half-life is controlled by the method according to the present invention and which is comprised in the antibody compositions according to the present invention has further glycosylation features which provide the antibody or fragment or derivative thereof with certain desirable properties.

The carbohydrates on the antibodies or fragments or derivatives thereof are preferably complex-type carbohydrates. In particular, preferably at least 50%, more preferably at least 60%, at least 70%, at least 80%, at least 90%, at least 95% and most preferably about 100% of the carbohydrates attached to the Fab part and/or the Fc part of the antibodies or fragments or derivatives thereof have the core structure shown in FIG. 21B, wherein a black square represents an N-acetylglucosamine residue (GlcNAc) and a gray circle represents a mannose residue (Man). More preferably, the carbohydrates having said core structure are complex-type carbohydrates such as biantennary complex-type carbohydrates having the structure shown in FIG. 21C, wherein a black square represents an N-acetylglucosamine residue (GlcNAc), a gray circle represents a mannose residue (Man), a white circle represents a galactose residue (Gal), a gray rhombus represents a sialic acid residue (SA), a black triangle represents a fucose residue (Fuc) and a gray square represents a bisecting N-acetylglucosamine residue (bisGlcNAc); and wherein GlcNAc, Gal and SA in the branches of the carbohydrate, bisGlcNAc as well as Fuc are only optionally present in the carbohydrate structure and may also be absent. In particular, the optional residues are present in the amounts as described herein.

In particular, in the antibody composition at least 50% of the carbohydrates attached to the antibody or fragment or derivative thereof carry at least one galactose residue. More preferably, at least 60%, at least 65%, at least 70%, at least 75% or at least 80% of said carbohydrates in the composition carry at least one galactose residue. In preferred embodiments, in the antibody composition at least 70% of the carbohydrates attached to the Fab part of the antibody or fragment or derivative thereof carry at least one galactose residue. More preferably, at least 75%, at least 80%, at least 85% or at least 90% of said carbohydrates in the composition carry at least one galactose residue. This galactose residue preferably is a terminal galactose residue, in particular attached to an N-acetylglucosamine residue, in particular positioned at the terminus of one or more branches of the carbohydrate chains, optionally further carrying a sialic acid residue. The term "terminal" in this respect only refers to the position of the galactose residue in the carbohydrate chain, in particular to its position in one of the branches of the carbohydrate chain. It does not mean that the galactose residue has to be the last monosaccharide unit at the non-reducing end of the carbohydrate chain. In particular, a terminal galactose unit may further carry a sialic acid residue.

In preferred embodiments, the antibody or fragment or derivative thereof has a human or human-like glycosylation pattern. Particularly, the carbohydrates attached to the antibody or fragment or derivative thereof preferably do not comprise a Galili epitope having the structure Gal$\alpha$(1→3)Gal$\beta$(1→4)GlcNAc. Preferably, they do not comprise the structure Gal$\alpha$(1→3)Gal. The carbohydrates attached to the antibody or fragment or derivative thereof also preferably do not comprise N-glycolylneuraminic acid (NeuGc) residues. Furthermore, in the composition preferably at least 25% of the sialic acid of the carbohydrates attached to the antibody or fragment or derivative thereof are coupled by a 2,6-linkage. More preferably, in the composition at least 40%, at least 45%, at least 50%, at least 55%, at least 60%, at least 65% or at least 68% of the sialic acid of the carbohydrates attached to the antibody or fragment or derivative thereof are coupled by a 2,6-linkage.

By using a glycosylation pattern which is similar to natural human glycosylation, adverse side-effects caused by the administration of the antibodies or fragments or derivatives thereof are reduced. In particular, carbohydrate structures such as the Galili epitope, NeuGc or a high amount of 2,3-linked sialic acids should be avoided since they might raise an immune response by the patient's immune system. For example, human anti-mouse antibody (HAMA) responses can be avoided by using chimeric or preferably humanized antibodies having a human-like glycosylation pattern. In particular the Galili epitope is known to cause large numbers of severe hypersensitivity reactions. In particular, the chimeric anti-EGFR antibody Cetuximab expressed in mouse SP2/0 cells (Erbitux) comprises carbohydrates carrying the Galili epitope and NeuGc and thus, induces immune reactions against the antibody in human patients. The antibodies obtained by the method according to the present invention, in particular EGFR-antibodies such as chimeric or humanized Cetuximab antibodies or antibodies having the same epitope as Cetuximab obtained by the method according to the present invention and which may be comprised in the antibody compositions according to the present invention do not comprise these disadvantageous carbohydrate structures.

Furthermore, in the composition according to the present invention preferably at least 10%, more preferably at least 15%, at least 20%, at least 23%, at least 25%, at least 27%, at least 29% or at least 30% of the carbohydrates attached to the antibody or fragment or derivative thereof carry a bisecting N-acetylglucosamine (bisGlcNAc) residue. In particular, in the composition preferably at least 50%, more preferably at least 55%, at least 60%, at least 65% or even at least 70% of the carbohydrates attached to the Fab part of the antibody or fragment or derivative thereof carry bisGlcNAc.

In certain embodiments, in the composition according to the present invention no more than 50%, preferably no more than 40%, no more than 30%, no more than 25%, no more than 20%, no more than 15%, no more than 13% or no more than 10% of the carbohydrates attached to the Fab part of the antibody or fragment or derivative thereof carry a fucose residue. In further embodiments, in the composition according to the present invention preferably at least 1%, more preferably at least 2%, at least 5%, at least 7%, at least 8%, at least 9% or at least 10% of the carbohydrates attached to the Fab part of the antibody or fragment or derivative thereof carry a fucose residue.

Enhanced Biological Activity

In preferred embodiments of the invention, the antibodies having an increased circulation half-life additionally have an enhanced biological activity. The biological activity of antibodies in this respect includes, for example, ADCC and CDC. The enhanced biological activity is mainly achieved by the optimized glycosylation pattern, in particular the optimized glycosylation pattern at the Fc part of the antibodies. For example, the ADCC activity of antibodies of the IgG type is mediated by binding of the antibody to Fc$\gamma$-receptors, in particular Fc$\gamma$RIIIa, via its Fc part. Fc$\gamma$RIIIa is expressed on natural killer (NK) cells and macrophages and upon activation by an antibody induces the release of cytokines and cytotoxic granules which results in apoptosis of the target cell bound by the antibody. The binding affinity of the antibody to the Fc$\gamma$-receptor is influenced by the carbohydrates attached to the glycosylation sites at the Fc part of the antibody. Therefore, optimization of the glycosylation pattern on the Fc part of an antibody will result in a stronger Fc$\gamma$RIIIa-binding and thus, in an enhanced ADCC activity.

The therapeutic efficacy of antibodies—in addition to their circulation half-life—in many cases depends on the induction of cytotoxic effects, in particular ADCC, against the target cells bound by the antibody. Therefore, increasing the ADCC activity of an antibody increases the therapeutic value thereof. For example, the same amount of antibodies administered to a patient will achieve a much higher therapeutic benefit when using antibodies optimized for their ADCC activity. Furthermore, for achieving the same therapeutic effect, a much lower amount of such antibodies has to be administered. As discussed herein, also the increase of the antibody's circulation half-life results in an enhanced therapeutic effect. Thus, a combination of both characteristics, the increased circulation half-life and the increased biological activity, provides highly advantageous therapeutic antibodies.

However, both properties are preferably optimized by controlling the glycosylation pattern of the antibodies. In particular, an increased degree of sialylation at the Fab part of the antibodies increases their circulation half-life while a decreased degree of fucosylation at the Fc part of the antibodies increases their ADCC activity. Furthermore, a high degree of sialylation at the Fc part may interfere with the ADCC activity. It is an achievement of the present invention to combine both features in one antibody composition and thus, to provide antibodies having a glycosylation pattern at the Fab part optimized for a high circulation half-life and having a glycosylation pattern at the Fc part optimized for a high biological activity.

It has been found that in particular a reduced amount of fucose, an increased amount of bisecting GlcNAc and/or a reduced amount of sialic acid in the carbohydrates attached to the Fc part of an IgG antibody will increase the antibody's affinity to Fc$\gamma$RIIIa and/or its ADCC activity.

Therefore, in preferred embodiments, the antibodies or fragments or derivatives thereof in the antibody compositions according to the invention have a low amount of fucose in the carbohydrates attached to the Fc part of the antibody or fragment or derivative thereof. Alternatively or in addition to this low amount of fucose, the antibodies or fragments or derivatives thereof may preferably have a high amount of bisecting GlcNAc and/or a low amount of sialic acid in the carbohydrates attached to the Fc part. Such a glycosylation pattern at the Fc part of the antibodies results in an increased ADCC activity of the antibodies.

In preferred embodiments, in the composition according to the present invention preferably at least 50%, more preferably at least 60%, at least 70%, at least 80%, at least 85%, at least 90%, at least 93%, at least 95% or at least 97% of the carbohydrates attached to the Fc part of the antibody or fragment or derivative thereof do not carry a fucose residue. A low fucose content in the glycosylation at the Fc part of the antibody in particular is important for a high antibody-dependent cell-mediated cytotoxicity (ADCC) of the antibody. Especially in the case of IgG antibodies, a high amount of fucose at the Fc glycosylation reduces the antibody's affinity to the Fcγ-receptor, in particular to FcγRIIIa which is expressed by natural killer cells and macrophages and mediates ADCC. Furthermore, a low amount of fucose in the carbohydrates attached to the glycosylation sites in the Fc part of IgG antibodies also reduces the differences in the binding affinity of the antibody to the different polymorphic variants of human FcγRIIIa (FcγRIIIa-158F and FcγRIIIa-158V). Thus, IgG antibodies having a low amount of fucose in the carbohydrates attached to the Fc part, in particular an amount of fucose as described above, can be used for treating patients by administering an amount of the antibody which does not cause a therapeutic effect when administering the same antibody having a high fucose content at the Fc part. Furthermore, using these low fucose antibodies, patients having different polymorphic variants of FcγRIIIa, such as homozygous FcγRIIIa-158F patients, homozygous FcγRIIIa-158V patients and heterozygous FcγRIIIa-158F/V patients, can be treated with the same amount of the antibody with a similar response to the same amount of antibody administered. In particular, binding of antibodies with high fucose content in their Fc part have an especially decreased affinity to FcγRIIIa-158F. Thus, using said low fucose antibodies, the patient coverage of the antibody therapy is broadened. This is also demonstrated in the examples wherein respective antibody compositions according to the present invention are used.

Furthermore, in the composition according to the present invention preferably at least 5%, more preferably at least 7%, at least 10%, at least 12%, at least 15%, at least 18%, at least 20% or at least 22% of the carbohydrates attached to the Fc part of the antibody or fragment or derivative thereof carry bisGlcNAc. A higher amount of bisGlcNAc at the Fc part of an antibody, in particular an IgG antibody, may result in an increased ADCC of the antibody.

Furthermore, in the composition according to the present invention preferably at least 60%, more preferably at least 65%, at least 70%, at least 75%, at least 80%, at least 85%, at least 90%, at least 93%, at least 95% or at least 97% of the carbohydrates attached to the Fc part of the antibody or fragment or derivative thereof do not carry a sialic acid residue. Furthermore, in the composition according to the present invention preferably at least 75%, more preferably at least 80%, at least 85%, at least 90%, at least 93%, at least 95% or at least 97% of the carbohydrates attached to the Fc part of the antibody or fragment or derivative thereof do not carry two or more sialic acid residues. A higher degree of sialylation at the Fc part of the antibody may have a negative influence on the binding to Fc receptors, in particular FcγRIIIa, and thus on the ADCC of the antibody. The cells and cell lines used for producing these antibody compositions preferably are capable of providing antibodies having a high sialylation degree at the Fab part and a low sialylation degree at the Fc part. An example of a suitable cell line is the cell line GT-5s and cells and cell lines derived therefrom or homologous thereto.

The Antibody Composition

In a second aspect, the present invention provides an antibody composition comprising antibodies or functional fragments or derivatives thereof, characterized in that the antibodies or fragments or derivatives thereof comprise at least one glycosylation site present in their Fab part, and characterized in that in the composition at least 65% of the carbohydrates attached to the Fab part of the antibodies or fragments or derivatives thereof carry at least one terminal sialic acid residue and/or less than 35% of the carbohydrates attached to the Fab part of the antibodies or fragments or derivatives thereof carry at least two free galactose units. Preferred characteristics of the antibody composition and in particular the preferred glycosylation patterns are described above in conjunction with the glycosylation pattern and below.

Preferably, at least 75%, more preferably at least 80%, at least 85%, at least 90%, at least 95%, at least 97%, at least 98%, at least 99% and most preferably about 100% of the antibodies or fragments or derivatives thereof in the antibody composition according to the present invention recognize, bind to and/or are specific for the same antigen, preferably the same epitope.

The antibody composition preferably is obtainable or is indeed obtained by the method for controlling the circulation half-life of an antibody or a fragment or derivative thereof according to the present invention wherein the amount of sialic acid in the carbohydrates attached to one or more glycosylation sites present in the Fab part of the antibody or fragment or derivative thereof is increased.

In particular, the antibodies or fragments or derivatives thereof in the antibody composition according to the present invention preferably have one or more of the features described above with respect to the method for controlling the circulation half-life according to the invention. In particular, the features and in particular the glycosylation pattern of the antibody or fragment or derivative thereof respectively the composition comprising the same, described in conjunction with the method for controlling the circulation half-life according to the invention, the features of the Fab glycosylation site, and the features of the glycosylation pattern, as described above, can also be applied to the antibodies or fragments or derivatives thereof in the antibody composition according to the present invention.

In preferred embodiments, at least 68%, at least 70%, at least 75% or at least 80% of the carbohydrates attached to the Fab part of the antibodies or fragments or derivatives thereof in the composition carry at least one terminal sialic acid residue. In particular, the average amount of sialic acid residues per carbohydrate chain in the carbohydrates attached to the at least one glycosylation site present in the Fab part of the antibodies or fragments or derivatives thereof in the composition is at least 0.65, preferably at least 0.7, at least 0.75, at least 0.8, at least 0.9, at least 1.0, at least 1.05 or at least 1.1. Furthermore, preferably less than 30%, less than 25%, less than 20%, less than 15%, less than 10%, less than 7% or less than 5% of the carbohydrates attached to the Fab part of the antibodies or fragments or derivatives thereof in the composition carry two or more free galactose units. In particular, the average amount of free galactose units per carbohydrate chain in the carbohydrates attached to the at least one glycosylation site present in the Fab part of the antibodies or fragments or derivatives thereof in the composition is less than 1.2, preferably less than 1.1, less than 1.0, less than 0.9, less than 0.85, less than 0.8, less than 0.75 or less than 0.7.

Preferably, at least one antibody or fragment or derivative thereof in the composition is glycosylated at the Fab part. More preferably, at least 25%, at least 40%, at least 50%, at least 60%, at least 70%, at least 75%, at least 80%, at least 85% or at least 90% of the antibodies or fragments or derivatives thereof in the composition are glycosylated at the Fab part. Furthermore, preferably at least 25%, more preferably at least 40%, at least 50%, at least 60%, at least 70%, at least 75%, at least 80%, at least 85%, or most preferably at least 90% of the antibodies or fragments or derivatives thereof in the composition are glycosylated at a specific glycosylation site in the Fab part as described herein, preferably at all glycosylation sites present in the Fab part. Antibodies or fragments or derivatives thereof may also be enriched for a respective glycosylation pattern, e.g. during or after their purification.

Preferably, the antibodies or fragments or derivatives thereof in the antibody composition further comprise at least one glycosylation site in their Fc part. This glycosylation site preferably is glycosylated with carbohydrates wherein the amount of carbohydrates in the composition which carry a fucose residue preferably is less than 50%, more preferably less than 40%, less than 30%, less than 25%, less than 20%, less than 15%, preferably less than 10% and most preferably less than 5%. Furthermore, in the composition the amount of carbohydrates attached to the Fc part carrying one or more sialic acid residues preferably is less than 50%, more preferably less than 40%, less than 30%, less than 25%, less than 20%, less than 15%, less than 10%, and most preferably less than 7% or less than 5%.

The antibodies or fragments or derivatives thereof in the composition preferably have a glycosylation pattern as listed in the following table:

| Embodiment | Glycos. site | B | F | S > 0 | S2 | G > 0 | G2 | free G |
|---|---|---|---|---|---|---|---|---|
| 1 | Fab | ≥50 | | ≥65 | | ≥70 | | |
| 2 | Fab | ≥50 | | | | ≥70 | | <35 |
| 3 | Fab | ≥50 | | ≥65 | | ≥70 | | <35 |
| 4 | Fab | ≥50 | | ≥65 | ≥25 | ≥70 | | |
| 5 | Fab | ≥50 | | ≥65 | | ≥70 | ≥70 | |
| 6 | Fab | ≥50 | | ≥65 | ≥25 | ≥70 | ≥70 | |
| 7 | Fab | ≥50 | | ≥70 | | ≥70 | | |
| 8 | Fab | ≥50 | | ≥65 | | ≥80 | | |
| 9 | Fab | ≥60 | | ≥65 | | ≥70 | | |
| 10 | Fab | ≥60 | | ≥70 | | ≥80 | | |
| 11 | Fab | ≥50 | | | | ≥70 | | <40 |
| 12 | Fab | ≥50 | | ≥65 | ≥30 | ≥70 | | |
| 13 | Fab | ≥50 | | ≥65 | | ≥80 | ≥80 | |
| 14 | Fab | ≥60 | | ≥70 | ≥30 | ≥80 | ≥80 | |
| 15 | Fab | ≥60 | | ≥70 | ≥30 | ≥80 | ≥80 | <40 |
| 16 | Fc | ≥5 | <50 | <40 | | | | |
| 17 | Fc | ≥5 | <50 | <40 | <25 | | | |
| 18 | Fc | ≥5 | <50 | <40 | | ≥50 | | |
| 19 | Fc | ≥5 | <50 | <40 | <25 | ≥50 | | |
| 20 | Fc | ≥12 | <50 | <40 | | | | |
| 21 | Fc | ≥5 | <80 | <40 | | | | |
| 22 | Fc | ≥5 | <50 | <25 | | | | |
| 23 | Fc | ≥12 | <80 | <25 | | | | |
| 24 | Fc | ≥5 | <50 | <40 | <15 | | | |
| 25 | Fc | ≥5 | <50 | <40 | | ≥60 | | |
| 26 | Fc | ≥12 | <80 | <25 | <15 | ≥60 | | |
| 27 | Fc | ≥5 | | <40 | | | | |
| 28 | Fc | ≥5 | | <40 | <25 | ≥50 | | |
| 29 | Fc | ≥12 | | <25 | <15 | ≥60 | | | shown are the percentage values of the carbohydrates attached to the indicated part of the antibodies or fragments or derivatives thereof in the composition having the following property: B: bisecting GlcNAc; F: fucose; S > 0: at least one sialic acid; S2: two sialic acids; G > 0: at least one galactose; S2: two galactoses; free G: at least one free galactose unit Preferably, the antibodies or fragments or derivatives thereof in the composition has a combination of one embodiment of a Fab glycosylation pattern (embodiments 1 to 15) and one embodiment of a Fc glycosylation pattern (embodiments 16 to 29), for example embodiments 1 and 16, embodiments 6 and 19, embodiments 10 and 23, embodiments 15 and 26, embodiments 1 and 27, embodiments 4 and 28 and embodiments 14 and 29.

In preferred embodiments, the antibodies or fragments or derivatives thereof in the antibody composition do not carry carbohydrates comprising the Galili epitope and/or N-glycolylneuraminic acid (NeuGc) residues.

The antibodies or fragments or derivatives thereof in the antibody composition according to the invention may be obtained by expression in a suitable cell line, in particular a human cell line, preferably an immortalized human cell line, such as a human blood cell line, in particular a human myeloid cell line or human myeloid leukemia cell line. Preferably, the antibodies or fragments or derivatives thereof in the antibody composition according to the invention are obtained by expression in the cell line GT-5s (DSM ACC 3078) or a cell or cell line derived therefrom or a cell or cell line homologous thereto as defined above, in particular a cell line having a low or no fucosylation activity such as a cell line selected for low fucosylation by single clone selection or by engineering the cell line, e.g. by gene knock-out. In particular, in the cell lines having low or no fucosylation activity, one or more defects in the fucose biosynthesis pathway and/or the fucose transportation system and/or the fucosylation enzymes may be present. The target enzymes which activity may be decreased or absent are preferably selected from the group consisting of α-1,6-fucosyltransferase encoded by the FUT8 gene, GDP-mannose-4,6-dehydratase, GDP-4-keto-6-deoxymannose-3,5-epimerase-4-reductase, and GDP-beta-L-fucose pyrophosphorylase. The defect may result in the expression of a protein having a decreased or no activity or may reduce or inhibit expression of the gene. Furthermore, a low fucose content may also be achieved by biological methods which do not alter the genetic structure of the cell such as RNA interference.

Furthermore, the present invention provides an antibody composition comprising a chimeric or humanized anti-EGFR antibody comprising a heavy chain variable region comprising a CDRH1 having the amino acid sequence of SEQ ID NO: 1, a CDRH2 having the amino acid sequence of SEQ ID NO: 2 and a CDRH3 having the amino acid sequence of SEQ ID NO: 3; and a light chain variable region comprising a CDRL1 having the amino acid sequence of SEQ ID NO: 4, a CDRL2 having the amino acid sequence of SEQ ID NO: 5 and a CDRL3 having the amino acid sequence of SEQ ID NO: 6, characterized in that
(i) the antibody comprises a glycosylation site present in the Fab part at amino acid position 85 of the heavy chain variable region according to the Kabat numbering, wherein in the composition at least 65%, preferably at least 70%, more preferred at least 75%, more preferred at least 80% of the carbohydrates attached to said glycosylation site present in the Fab part carry at least one terminal sialic acid residue, or
(ii) the antibody does not comprise a glycosylation site in the Fab part.

As described above, the respective antibody compositions show an improved half-life compared to antibody compositions not having a respective glycosylation pattern. Preferably, the chimeric or humanized anti-EGFR antibody comprises a glycosylation site present in the Fc part and in the composition at least 80%, preferably at least 85%, more preferred at least 90%, most preferred at least 95% of the carbohydrates attached to the Fc part do not carry a fucose residue. Furthermore, preferably at least 70%, at least 75%, at least 80%, preferably at least 85%, more preferred at least 90%, most preferred at least 95% of the carbohydrates attached to the Fc part do not carry a sialic acid residue. Furthermore, according to one embodiment at least 10% of the carbohydrates attached to the Fc part carry a bisecting N-acteylglucosamine residue, at least 70% of the carbohydrates attached to the antibody carry at least one galactose residue (this galactose residue preferably is a terminal galactose residue, in particular attached to an N-acetylglucosamine residue, in particular positioned at the terminus of one or more branches of the carbohydrate chains, optionally further carrying a sialic acid residue), the carbohydrates attached to the antibody do not comprise a Galili epitope having the structure the structure Galα(1→3)Galβ(1→4)GlcNAc, and the carbohydrates attached to the antibody do not comprise N-glycolylneuraminic acid (NeuGc) residues. Furthermore, according to one embodiment, at least 50%, preferably at least 60%, more preferred at least 65%, most preferred at least 70% of the carbohydrates attached to the Fab part carry a bisecting N-acteylglucosamine residue. According to one embodiment, at least 25% or at least 30%, preferably at least 40% of the carbohydrates attached to the antibody comprise sialic acid. According to one embodiment, the respective antibody composition combines all of the features described above as preferred. Preferably, the antibody is an IgG antibody. According to one embodiment, an antibody composition is provided, comprising functional fragments or derivatives of a respectively glycosylated antibody.

Moreover, the present invention also provides an antibody composition comprising a chimeric or humanized anti-Muc1 antibody comprising a heavy chain variable region comprising a CDRH1 having the amino acid sequence of SEQ ID NO: 7, a CDRH2 having the amino acid sequence of SEQ ID NO: 8 and a CDRH3 having the amino acid sequence of SEQ ID NO: 9; and a light chain variable region comprising a CDRL1 having the amino acid sequence of SEQ ID NO: 10, a CDRL2 having the amino acid sequence of SEQ ID NO: 11 and a CDRL3 having the amino acid sequence of SEQ ID NO: 12, characterized in that the antibody comprises a glycosylation site present in the Fab part at amino acid position 54 of the heavy chain variable region according to the Kabat numbering, wherein in the composition at least 65%, preferably at least 70% of the carbohydrates attached to said glycosylation site present in the Fab part carry at least one terminal sialic acid residue. As described above, the respective antibody compositions show an improved half-life compared to antibody compositions not having a respective glycosylation pattern.

Preferably, the chimeric or humanized anti-Muc1 antibody comprises a glycosylation site present in the Fc part and in the composition at least 80%, preferably at least 85%, more preferred at least 90% and most preferred at least 95% of the carbohydrates attached to the Fc part do not carry a fucose residue and/or at least 80%, preferably at least 90% of the carbohydrates attached to the Fc part do not carry a sialic acid residue. Furthermore, according to one embodiment, at least 5% of the carbohydrates attached to the Fc part carry a bisecting N-acteylglucosamine residue, at least 70% of the carbohydrates attached to the antibody carry at least one galactose residue (this galactose residue preferably is a terminal galactose residue, in particular attached to an N-acetylglucosamine residue, in particular positioned at the terminus of one or more branches of the carbohydrate chains, optionally further carrying a sialic acid residue), the carbohydrates attached to the antibody do not comprise a Galili epitope having the structure the structure Galα(1→3)Galβ(1→4)GlcNAc, and the carbohydrates attached to the antibody do not comprise N-glycolylneuraminic acid (NeuGc) residues. According to one embodiment, the respective antibody composition combines all of the features described above as preferred. Preferably, the antibody is an IgG antibody. According to one embodiment, an antibody composition is provided, comprising functional fragments or derivatives of a respectively glycosylated antibody.

In a further aspect, the present invention provides an antibody or functional fragment or derivative thereof, wherein the amino acid sequence of at least one CDR of the antibody or fragment or derivative thereof is derived from a reference antibody which comprises at least one glycosylation site in the Fab part, and wherein the antibody or fragment or derivative thereof do not comprise a glycosylation site in the Fab part, and wherein the antibody or functional fragment or derivative thereof has a higher circulation half-life than the reference antibody.

As discussed above, removing the glycosylation site(s) in the Fab part of the antibody or functional fragment or derivative thereof results in an increase of the circulation half-life compared to the reference antibody which comprises a glycosylation site in the Fab part. The higher circulation half-life can be seen in at least one species, preferably it is seen in a primate, preferably in a human. Preferably, the antibody or functional fragment or derivative thereof according to the invention binds to the same epitope as the reference antibody.

Preferably, the amino acid sequences of all three CDRs of the heavy chain variable region of the antibody or fragment or derivative thereof are derived from the reference antibody. Furthermore, preferably, the amino acid sequences of all three CDRs of the light chain variable region of the antibody or fragment or derivative thereof are derived from the reference antibody. In preferred embodiments, the amino acid sequences of the CDRs which are derived from the reference antibody are identical to the amino acid sequences of the corresponding CDRs of the reference antibody.

In preferred embodiments, the entire amino acid sequence of the heavy chain variable region and/or the entire amino acid sequence of the light chain variable region of the antibody or fragment or derivative thereof is derived from the reference antibody. In certain embodiments, the glycosylation site in the Fab part of the reference antibody is in the heavy chain or light chain variable region of the reference antibody and the antibody or fragment or derivative thereof according to the invention comprise at least one amino acid mutation in the heavy chain or light chain variable region derived from the reference antibody which amino acid mutation removes said glycosylation site. In further embodiments, the entire amino acid sequence of the antibody or fragment or derivative thereof is derived from the reference antibody wherein however, it does not comprise a glycosylation site in the Fab fragment.

The antigen binding affinity of the antibody or functional fragment or derivative thereof preferably is similar to or higher than the antigen binding affinity of the reference antibody. Preferably, the antigen binding affinity is not decreased by more than 20%, preferably not more than 15%, not more than 10% or not more than 5%. Furthermore, according to one embodiment, the circulation half-life of the antibody or functional fragment or derivative thereof is at least 5%, preferably, at least 10%, at least 15%, at least 20%, at least 25%, at least 30%, at least 40% or at least 50% higher than the circulation half-life of the reference antibody. As discussed above, the increase in the circulation half-life is observed in at least one species, preferably in a primate, most preferably in a human.

The reference antibody preferably is selected from the group consisting of anti-EGFR antibodies, in particular anti-EGFR antibodies as described above, for example Cetuximab or antibodies binding to the same epitope as Cetuximab, anti-MUC1 antibodies, in particular anti-MUC1 antibodies as described above, for example Pankomab or antibodies binding to the same epitope as Pankomab, anti-Aβ antibodies such as Solanezumab or antibodies binding to the same epitope as Solanezumab, and anti-CD52 antibodies such as Alemtuzumab or antibodies binding to the same epitope as Alemtuzumab.

Preferred anti-EGFR antibodies and preferred anti-MUC1 antibodies and their CDR sequences are described above. It is referred to the above disclosure which also applies here. These antibodies are preferably used as reference antibody. As discussed above, the antibody or functional fragment or derivative thereof preferably comprises at least one, preferably all CDRs of the respective antibodies.

Preferred anti-CD52 antibodies are also described above and comprise one or more of the CDRs selected from the group consisting of CDRH1 having the amino acid sequence of SEQ ID NO: 15, CDRH2 having the amino acid sequence of SEQ ID NO: 16, CDRH3 having the amino acid sequence of SEQ ID NO: 17, CDRL1 having the amino acid sequence of SEQ ID NO: 18, CDRL2 having the amino acid sequence of SEQ ID NO: 19, CDRL3 having the amino acid sequence of SEQ ID NO: 20. In particular, the antibody may be an anti-CD52-antibody comprising (i) a heavy chain variable region comprising a CDRH1 having the amino acid sequence of SEQ ID NO: 15, a CDRH2 having the amino acid sequence of SEQ ID NO: 16 and a CDRH3 having the amino acid sequence of SEQ ID NO: 17;

(ii) optionally a light chain variable region comprising a CDRL1 having the amino acid sequence of SEQ ID NO: 18, a CDRL2 having the amino acid sequence of SEQ ID NO: 19 and a CDRL3 having the amino acid sequence of SEQ ID NO: 20;

(iii) a glycosylation site present in the Fab part at amino acid position 60 of the heavy chain variable region according to the Kabat numbering; and (iv) optionally a glycosylation site present in the Fc part at amino acid position 297 of the heavy chain constant region 2.

Said antibody preferably is capable of binding the same antigen, in particular the same epitope as Alemtuzumab.

Preferred anti-Aβ antibodies are also described above and comprise one or more of the CDRs selected from the group consisting of CDRH1 having the amino acid sequence of SEQ ID NO: 21, CDRH2 having the amino acid sequence of SEQ ID NO: 22, CDRH3 having the amino acid sequence of SEQ ID NO: 23, CDRL1 having the amino acid sequence of SEQ ID NO: 24, CDRL2 having the amino acid sequence of SEQ ID NO: 25, CDRL3 having the amino acid sequence of SEQ ID NO: 26. In particular, the antibody may be an anti-Aβ antibody comprising (i) a heavy chain variable region comprising a CDRH1 having the amino acid sequence of SEQ ID NO: 21, a CDRH2 having the amino acid sequence of SEQ ID NO: 22 and a CDRH3 having the amino acid sequence of SEQ ID NO: 23;

(ii) optionally a light chain variable region comprising a CDRL1 having the amino acid sequence of SEQ ID NO: 24, a CDRL2 having the amino acid sequence of SEQ ID NO: 25 and a CDRL3 having the amino acid sequence of SEQ ID NO: 26;

(iii) a glycosylation site present in the Fab part at amino acid position 55 of the heavy chain variable region according to the Kabat numbering; and (iv) optionally a glycosylation site present in the Fc part at amino acid position 297 of the heavy chain constant region 2.

Said antibody preferably is capable of binding the same antigen, in particular the same epitope as Solanezumab.

Exemplary reference antibodies are also listed in the following Table:

| Antibody | Trade name | Antigen | Expression cell line | Therapeutic use |
|---|---|---|---|---|
| Cetuximab | Erbitux | EGFR | SP2/0 mouse myeloma cell line | cancer treatment, e.g. metastatic colorectal cancer and squamous cell carcinoma of head and neck |
| Pankomab | — | MUC1 | NM-F9 (DSM ACC2606) | cancer treatment, e.g. ovarian cancer, breast cancer, lung cancer, cervix cancer, endometrium cancer, gastrointestinal cancer, kidney cancer and urothelial cancer |
| Solanezumab | — | Amyloid beta (Aβ) | SP2/0 mouse myeloma cell line | treatment of Alzheimer's disease |
| Alemtuzumab | Campath | CD52 | CHO cell line | treatment of chronic lymphocytic leukemia (CLL), cutaneous T-cell lymphoma (CTCL), T-cell lymphoma and multiple sclerosis |

Details with respect to the Fab glycosylation site are described above, it is referred to the above disclosure. The glycosylation site in the Fab part of the reference antibody preferably is an N-glycosylation site, in particular having the amino acid sequence Asn Xaa Ser/Thr, wherein Xaa is any amino acid preferably except Pro.

In preferred embodiments, the glycosylation site in the Fab part of the reference antibody is in the heavy chain or light chain variable region, and the amino acid sequence of the heavy chain or light chain variable region of the antibody or functional fragment or derivative thereof according to this aspect of the present invention differs from the corresponding amino acid sequence of the reference antibody in at least one amino acid so that the glycosylation site in the heavy chain or light chain variable region is removed.

The glycosylation site in the reference antibody may be removed by any method known in the art and in particular by altering the amino acid sequence. Options are also described above, it is referred to the above disclosure. Preferably, the glycosylation site is removed by adding, substituting and/or deleting one or more amino acids in the amino acid sequence of the reference antibody. In particular, the amino acid of the glycosylation site which functions as acceptor of the carbohydrate chain is deleted or substituted by another amino acid which cannot function as acceptor for the carbohydrate chain, and/or the recognition sequence of the enzyme responsible for glycosylation of the antibody, in particular oligosaccharyltransferase, is altered so that the enzyme cannot recognize the amino acid sequence and thus, cannot transfer the carbohydrate chain onto the polypeptide chain of the antibody. In particular, for removing a N-glycosylation site, the amino acid sequence of the glycosylation site Asn Xaa Ser/Thr, wherein Xaa is any amino acid residue preferably except Pro, is altered so that (i) the Asn is deleted or substitute for any other amino acid, (ii) the Ser or Thr is deleted or substituted with any amino acid except Ser and Thr, (iii) the Xaa is deleted or substituted with Pro, and/or (iv) a further amino acid is introduced between the Asn and the Ser/Thr.

Furthermore, the present invention provides an antibody composition comprising antibodies or functional fragments or derivatives thereof as described above which, compared to the corresponding reference antibody, do not comprise a glycosylation site in the Fab part. It is referred to the above disclosure for details of the antibody or functional fragment or derivative thereof. The antibody composition according to this aspect may have any of the features disclosed herein with respect to antibody compositions described above. In particular, the antibodies or functional fragments or derivatives thereof in the composition may have a glycosylation pattern at the Fc part as defined and described above.

The present invention further provides a method for producing a nucleic acid coding for an antibody or a functional fragment or derivative thereof having an increased circulation half-life, comprising the steps of:
(a) providing a nucleic acid coding for an antibody or a functional fragment or derivative thereof having a glycosylation site in the Fab part (reference antibody); and
(b) introducing a mutation into the nucleic acid so that the glycosylation site in the Fab part of the encoded antibody or a functional fragment or derivative thereof is removed.

Thereby, an antibody or a functional fragment or derivative thereof is obtained which binds to the same epitope as the original antibody (herein also referred to as reference antibody) but which has an increased circulation half-life. As discussed above, the increase in the circulation half-life is observed preferably in at least one species, preferably in a primate, most preferred in a human. Details with respect to suitable and preferred reference antibodies are described above; it is referred to the above disclosure. The antigen binding affinity of the obtained antibody or functional fragment or derivative thereof preferably is similar to or higher than the antigen binding affinity of the reference antibody. Preferably, the antigen binding affinity is not decreased by more than 20%, preferably not more than 15%, not more than 10% or not more than 5%. Furthermore, according to one embodiment, the circulation half-life of the obtained antibody or functional fragment or derivative thereof is at least 5%, preferably, at least 10%, at least 15%, at least 20%, at least 25%, at least 30%, at least 40% or at least 50% higher than the circulation half-life of the reference antibody. As discussed above, the increase in the circulation half-life is observed in at least one species, preferably in a primate, most preferably in a human. Suitable methods for removing a glycosylation site in the Fab part are described above, it is referred to the respective disclosure.

The present invention also provides a method for producing an antibody or a functional fragment or derivative thereof having an increased circulation half-life, comprising the steps of:
(a) providing a nucleic acid coding for an antibody or a functional fragment or derivative thereof having a glycosylation site in the Fab part (reference antibody);
(b) introducing a mutation into the nucleic acid so that the glycosylation site in the Fab part of the encoded antibody or a functional fragment or derivative thereof is removed;
(c) expressing the nucleic acid obtained in step (b) in a host cell to produce an antibody or a functional fragment or derivative thereof which does not have a glycosylation site in the Fab part and which has a higher circulation half-life than the antibody or a functional fragment or derivative thereof having a glycosylation site in the Fab part.

The antibody or functional fragment or derivative thereof can be obtained e.g. from the culture medium comprising the host cells. Suitable host cells for expressing antibodies are known in the prior art and are also described above. Preferably the antibody or functional fragment or derivative thereof is purified. Details with respect to the reference antibody and the obtained mutated antibody not comprising a glycosylation site in the Fab fragment are described above, It is referred to the above disclosure.

Furthermore, the present invention provides nucleic acid obtainable from the method for producing a nucleic acid coding for an antibody or a functional fragment or derivative thereof having an increased circulation half-life and an antibody or a functional fragment or derivative thereof obtainable from the method for producing an antibody or a functional fragment or derivative thereof having an increased circulation half-life.

In a further aspect, the present invention provides an antibody or functional fragment or derivative thereof, wherein the amino acid sequence of at least one CDR of the antibody or fragment or derivative thereof is derived from a reference antibody, and wherein the antibody or fragment or derivative thereof comprises at least one additional glycosylation site in the Fab part which is not present in the reference antibody. In certain embodiments, the antibody or functional fragment or derivative thereof has a lower circulation half-life than the reference antibody. In these embodiments, the antibody or functional fragment or derivative thereof preferably has a low degree of sialylation and/or a high degree of free galactose units at the Fab part, in particular an amount of sialic acids and/or an amount of free galactose units in the carbohydrates attached to the at least one glycosylation site present in the Fab part as described above with respect to the antibodies or fragments or derivatives thereof having a decreased circulation half-life, i.e. obtained after step (b1) or (b3) of the method for controlling the circulation half-life of an antibody or a functional fragment or derivative thereof according to the invention. It is referred to the above disclosure which also likewise applies here.

As discussed above, adding (a) glycosylation site(s) in the Fab part of the antibody or functional fragment or derivative thereof may result in a decrease of the circulation half-life compared to the reference antibody which does not comprise a respective glycosylation site in the Fab part. The lower circulation half-life can be seen in at least one species, preferably it is seen in a primate, preferably in a human. Preferably, the antibody or functional fragment or derivative thereof according to the invention binds to the same epitope as the reference antibody.

Preferably, the reference antibody does not comprise a glycosylation site in the Fab part.

Preferably, the amino acid sequences of all three CDRs of the heavy chain variable region of the antibody or fragment or derivative thereof are derived from the reference antibody. Furthermore, preferably, the amino acid sequences of all three CDRs of the light chain variable region of the antibody or fragment or derivative thereof are derived from the reference antibody. In preferred embodiments, the amino acid sequences of the CDRs which are derived from the reference antibody are identical to the amino acid sequences of the corresponding CDRs of the reference antibody.

In preferred embodiments, the entire amino acid sequence of the heavy chain variable region and/or the entire amino acid sequence of the light chain variable region of the antibody or fragment or derivative thereof is derived from the reference antibody. In certain embodiments, the glycosylation site in the Fab part of the antibody or fragment or derivative thereof is in the heavy chain or light chain variable region of the reference antibody and the antibody or fragment or derivative thereof according to the invention comprise at least one amino acid mutation in the heavy chain or light chain variable region derived from the reference antibody which amino acid mutation introduces said glycosylation site(s). In further embodiments, the entire amino acid sequence of the antibody or fragment or derivative thereof is derived from the reference antibody, wherein however, it comprises at least one additional glycosylation site in the Fab fragment.

The antigen binding affinity of the antibody or functional fragment or derivative thereof preferably is similar to or higher than the antigen binding affinity of the reference antibody. Preferably, the antigen binding affinity is not decreased by more than 20%, preferably not more than 15%, not more than 10% or not more than 5%. Furthermore, according to one embodiment, the circulation half-life of the antibody or functional fragment or derivative thereof is at least 5%, preferably, at least 10%, at least 15%, at least 20%, at least 25%, at least 30%, at least 40% or at least 50% lower than the circulation half-life of the reference antibody. As discussed above, the decrease in the circulation half-life is observed in at least one species, preferably in a primate, most preferably in a human.

Details with respect to the Fab glycosylation site are described above, it is referred to the above disclosure. The one or more additional glycosylation sites in the Fab part of the antibody or functional fragment or derivative thereof preferably are N-glycosylation sites, in particular having the amino acid sequence Asn Xaa Ser/Thr, wherein Xaa is any amino acid preferably except Pro.

In preferred embodiments, at least one, preferably all, of the additional glycosylation site(s) in the Fab part of the antibody or functional fragment or derivative thereof is in the heavy chain or light chain variable region, preferably the heavy chain variable region, and the amino acid sequence of the heavy chain or light chain variable region of the antibody or functional fragment or derivative thereof according to this aspect of the present invention differs from the corresponding amino acid sequence of the reference antibody in at least one amino acid so that the at least one additional glycosylation sites in the heavy chain or light chain variable region are introduced. In further embodiments, at least one, preferably all, of the additional glycosylation site in the Fab part of the antibody or functional fragment or derivative thereof is in the heavy chain or light chain constant region, preferably in the heavy chain constant region, and the amino acid sequence of the heavy chain or light chain constant region of the antibody or functional fragment or derivative thereof according to this aspect of the present invention differs from the corresponding amino acid sequence of the reference antibody in at least one amino acid so that the at least one additional glycosylation sites in the heavy chain or light chain constant region are introduced.

The glycosylation site in the antibody or functional fragment or derivative thereof may be introduced by any method known in the art and in particular by altering the amino acid sequence. Options are also described above, it is referred to the above disclosure. Preferably, the glycosylation site is introduced by adding, substituting and/or deleting one or more amino acids in the amino acid sequence of the reference antibody. In particular, the amino acids are altered so that a functional glycosylation site is formed which comprises an amino acid which functions as acceptor of the carbohydrate chain and/or which comprises a recognition sequence of an enzyme responsible for glycosylation of the antibody, in particular oligosaccharyltransferase. In particular, for introducing a N-glycosylation site, the amino acid sequence of the reference antibody is altered so that a glycosylation site having the amino acid sequence motif Asn Xaa Ser/Thr, wherein Xaa is any amino acid residue preferably except Pro, is present in the antibody or functional fragment or derivative thereof according to the invention.

Furthermore, the present invention provides an antibody composition comprising antibodies or functional fragments or derivatives thereof as described above which, compared to the corresponding reference antibody, comprise at least one additional glycosylation site in the Fab part. It is referred to the above disclosure for details of the antibody or functional fragment or derivative thereof. The antibody composition according to this aspect may have any of the features disclosed herein with respect to antibody compositions described above. In particular, the antibodies or functional fragments or derivatives thereof in the composition may have a glycosylation pattern at the Fc part and/or the Fab part as defined and described above.

In certain embodiments, the antibodies or functional fragments or derivatives thereof in the antibody composition have a lower circulation half-life than the reference antibody. In these embodiments, the antibodies or functional fragments or derivatives thereof preferably have a low degree of sialylation and/or a high degree of free galactose units at the Fab part, in particular an amount of sialic acids and/or an amount of free galactose units in the carbohydrates attached to the at least one glycosylation site present in the Fab part as described above with respect to the antibodies or fragments or derivatives thereof having a decreased circulation half-life, i.e. obtained after step (b1) or (b3) of the method for controlling the circulation half-life of an antibody or a functional fragment or derivative thereof according to the invention. It is referred to the above disclosure which also likewise applies here. In particular, in the composition less than 50% of the carbohydrates attached to the at least one glycosylation site present in the Fab part comprise at least one sialic acid residue. Preferably, in the composition less than 40%, less than 30%, less than 20%, less than 15%, less than 10%, less than 7%, less than 5%, less than 3%, less than 2%, less than 1% or about 0% of the carbohydrates attached to the one or more glycosylation sites present in the Fab part comprise one or more sialic acid residues. Furthermore, preferably in the composition at least 50% of the carbohydrates attached to the at least one glycosylation site present in the Fab part comprise at least one free galactose unit, preferably at least two free galactose units. Preferably, in the composition at least 60%, more preferably at least 70%, at least 80%, at least 85%, at least 90%, at least 95%, at least 97% or most preferably at least 98% of the carbohydrates attached to the one or more glycosylation sites in the Fab part comprise at least one free galactose unit, preferably at least two free galactose units.

The present invention further provides a method for producing a nucleic acid coding for an antibody or a functional fragment or derivative thereof having a decreased circulation half-life, comprising the steps of:
  (a) providing a nucleic acid coding for an antibody or a functional fragment or derivative thereof (reference antibody); and
  (b) introducing a mutation into the nucleic acid so that at least one additional glycosylation site is introduced into the Fab part of the encoded antibody or a functional fragment or derivative thereof.

Thereby, an antibody or a functional fragment or derivative thereof is obtained which binds to the same epitope as the original antibody (herein also referred to as reference antibody) but which has a decreased circulation half-life. As discussed above, the decrease in the circulation half-life is observed preferably in at least one species, preferably in a primate, most preferred in a human. Details with respect to suitable and preferred reference antibodies and suitable glycosylation characteristics of the antibody or fragment or derivative thereof are described above; it is referred to the above disclosure. The antigen binding affinity of the obtained antibody or functional fragment or derivative thereof preferably is similar to or higher than the antigen binding affinity of the reference antibody. Preferably, the antigen binding affinity is not decreased by more than 20%, preferably not more than 15%, not more than 10% or not more than 5%. Furthermore, according to one embodiment, the circulation half-life of the obtained antibody or functional fragment or derivative thereof is at least 5%, preferably, at least 10%, at least 15%, at least 20%, at least 25%, at least 30%, at least 40% or at least 50% lower than the circulation half-life of the reference antibody. As discussed above, the decrease in the circulation half-life is observed in at least one species, preferably in a primate, most preferably in a human. Suitable methods for introducing a glycosylation site in the Fab part are described above; it is referred to the respective disclosure.

The present invention also provides a method for producing an antibody or a functional fragment or derivative thereof having a decreased circulation half-life, comprising the steps of:
  (a) providing a nucleic acid coding for an antibody or a functional fragment or derivative thereof (reference antibody);
  (b) introducing a mutation into the nucleic acid so that at least one additional glycosylation site is introduced into the Fab part of the encoded antibody or a functional fragment or derivative thereof;
  (c) expressing the nucleic acid obtained in step (b) in a host cell to produce an antibody or a functional fragment or derivative thereof which has at öleast one additional glycosylation site in the Fab part and which has a lower circulation half-life than the antibody or a functional fragment or derivative thereof not having said at least one additional glycosylation site in the Fab part.

The antibody or functional fragment or derivative thereof can be obtained e.g. from the culture medium comprising the host cells. Suitable host cells for expressing antibodies are known in the prior art and are also described above. Particular preferred host cells have a low or no sialylation activity. Preferably, the antibody or functional fragment or derivative thereof is purified. Details with respect to the reference antibody and the obtained mutated antibody comprising at least one additional glycosylation site in the Fab part are described above; it is referred to the above disclosure.

Furthermore, the present invention provides a nucleic acid obtainable from the method for producing a nucleic acid coding for an antibody or a functional fragment or derivative thereof having a decreased circulation half-life and an antibody or a functional fragment or derivative thereof obtainable from the method for producing an antibody or a functional fragment or derivative thereof having a decreased circulation half-life.

Medical Use of the Antibodies and the Antibody Compositions

The antibodies and antibody compositions described above and in particular the anti-EGFR antibody and anti-Muc1 antibody compositions described above are particularly advantageous since they comprise antibodies which have optimized glycosylation patterns and thereby have an increased half-life, an increased ADCC activity and a high compatibility with the human immune system. In particular the anti-EGFR antibody in the antibody compositions according to the invention comprising a chimeric or humanized anti-EGFR antibody has a higher circulation half-life and a higher ADCC activity than the anti-EGFR antibody Cetuximab expressed in mouse SP2/0 cells (Erbitux). Furthermore, in particular the absence of Galili structures reduces unwanted side effects. This combination of advantageous features furthermore, allows reducing the necessary antibody dosage necessary for effective treatment thereby also lowering the risk of unwanted side effects. Furthermore, the patient spectra is broadened by the optimized glycosylation pattern and thus allows the treatment of patients of all FcgammaIII receptor types, including patients of the F/F and F/V allotype. Thus, the present invention provides antibody compositions and in particular anti-EGFR antibody compositions with improved therapeutic profile.

The antibody compositions according to the present invention may be used in medicine, in particular in the treatment, prophylaxis, diagnosis, prognosis and/or monitoring of a disease, in particular cancer. Thus, the antibody composition preferably is a pharmaceutical composition. The cancer may be any cancer, in particular a cancer as described above.

In preferred embodiments, the antibody composition comprises an anti-EGFR antibody as described herein and is for use in the treatment, prophylaxis, diagnosis, prognosis and/or monitoring of a cancer, in particular a cancer expressing EGFR. In this embodiments, the cancer preferably is selected from the group consisting of colorectal cancer, metastatic colorectal cancer, head-neck cancer, squamous cell carcinoma of head and neck, non-small cell lung cancer, renal cell carcinoma, mamma carcinoma and triple negative mamma carcinoma. The antibody composition comprising an anti-EGFR antibody can be used in cancer therapy together with another agent, in particular a chemotherapeutic agent such as described herein, for example irinotecan, and/or in combination with radiation therapy. Furthermore, it can be used after a preceding anti-cancer therapy, such as irinotecan therapy, platinum-based therapy or radiation therapy.

In further preferred embodiments, the antibody composition comprises an anti-MUC1 antibody as described herein and is for use in the treatment, prophylaxis, diagnosis, prognosis and/or monitoring of a cancer, in particular a cancer expressing MUC1, in particular the tumor antigen TA-MUC1. In this embodiments, the cancer preferably is selected from the group consisting of ovarian cancer, breast cancer, lung cancer, cervix cancer, endometrium cancer, gastrointestinal cancer, kidney cancer and urothelial cancer. The antibody composition comprising an anti-MUC1 antibody can be used in cancer therapy together with another agent, in particular a chemotherapeutic agent such as described herein, and/or in combination with radiation therapy. Furthermore, it can be used after a preceding anti-cancer therapy, such as chemotherapy or radiation therapy.

The antibody compositions according to the present invention, in particular the antibody compositions wherein at least 70%, preferably at least 80%, more preferred at least 90% and most preferred at least 95% of the carbohydrates attached to the Fc part of the antibodies or fragments or derivatives thereof in the composition do not comprise a fucose residue, may be used in the treatment of cancer in patients having at least one allele coding for FcγRIIIa-158F. Due to the low fucose content in the Fc glycosylation, in particular the ADCC activity of the antibodies in patients having at least one allele coding for FcγRIIIa-158F is increased and especially is similar to that in patients being homozygote for the FcγRIIIa-158V gene. This advantageous feature combined with an improved half-life achieved by increasing the amount of sialic acid in the Fab part or by removing one or preferably all glycosylation sites in the Fab part as described herein provides antibodies with an improved clinical profile.

For example, treatment of a cancer patient may include and/or result in reduction of tumor size, elimination of malignant cells, prevention of metastasis, the prevention of relapse in a patient who has been put into remission, reduction, partial or complete killing of disseminated cancer, in particular tumor cells or metastasizing cancer, in particular cells including those in circulation or those during evasion or invasion, a prolongation of survival and/or a prolongation of the time to tumor respectively cancer progression. The antibody or fragment or derivative thereof in the antibody compositions according to the invention for use in the treatment, diagnosis or prevention of cancer may be in the form of a free antibody or fragment or derivative or may be coupled to a further substance, for example a therapeutically active agent such as a radionuclide or a cytotoxic agent or a marker such as a radionuclide or a fluorescence marker. Furthermore, the antigen composition may further comprise one or more further therapeutically active agents such as chemotherapeutic agents. The further agent preferably is a cytotoxic agent or a radionuclide, in particular alkylating agents such as cisplatin, anti-metabolites, plant alkaloids and terpenoids, vinca alkaloids, podophyllotoxin, taxanes such as taxol, topoisomerase inhibitors such as irinotecan and topotecan, or antineoplastics such as doxorubicin. For use in diagnosis, prognosis and/or monitoring of a disease, the antibody or fragment or derivative thereof according to the invention preferably is coupled to a labeling agent which is capable of producing a detectable signal. In particular, said labeling agent may be a radionuclide, a fluorophore or an enzyme.

With respect to antibody compositions according to the present invention comprising an anti-EGFR antibody having an increased ADCC activity, said improved clinical profile also includes the expansion of the group of patients which can be treated by the antibody composition. The common treatment of cancer patients using anti-EGFR antibodies, in particular the anti-EGFR antibodies disclosed in WO 96/40210 or U.S. Pat. No. 4,943,533, bases on the ability of the antibody to inhibit the intracellular signaling of EGFR by binding to and blocking the ligand binding site of the receptor. Since the downstream signaling pathway of EGFR results in cell proliferation, blocking of EGFR signaling reduces cell proliferation and thus, tumor growth. However, this mode of action does not work for tumor cells wherein said signal transduction pathway is continuously activated irrespectively of the activation status of the EGFR. This may happen, for example, in case of constitutively active mutations of one or more members of the signal transduction pathway, in particular a constitutively active K-Ras mutant. Furthermore, this mode of action also does not work with tumor cells which proliferate independent of the EGFR signal transduction pathway.

In contrast to the commonly used anti-EGFR antibodies, the antibody composition according to the present invention comprising anti-EGFR antibodies having an improved circulation half-live and/or an increased ADCC activity are capable of killing any tumor cells expressing EGFR, in particular those tumor cells having a high EGFR expression rate such as those wherein the expression of EGFR is increased in comparison to normal tissue. Thus, said antibody composition according to the present invention has the advantage that not only the proliferation of target tumor cells is inhibited, but the target tumor cells are killed, and that the anti-EGFR antibodies are effective against tumor cells irrespective of the activation status of the EGFR signal transduction pathway. In particular, the therapeutic activity of these anti-EGFR antibodies is more independent of the activity of downstream elements of the EGFR signal transduction pathway, especially constitutively active K-Ras mutants. Thus, using the antibody composition according to the present invention comprising anti-EGFR antibodies having an increased ADCC activity as described above expands the group of treatable patients to those patients having a tumor or cancer cells which cannot be treated by blocking ligand binding to EGFR. In particular, this includes tumors or cancer cells comprising an activating mutation or overexpression in the EGFR signal transduction pathway such as a constitutively active K-Ras mutant, a constitutively active PI 3 kinase mutant or an overexpression of Raf kinase. Examples of respective K-Ras mutants are K-Ras having a mutation at amino acid number 12 such as K-Ras G12V, K-Ras G12D, K-Ras G12C, K-Ras G12S, K-Ras G12A and K-Ras G12R, K-Ras having a mutation at amino acid number 13 such as K-Ras G13D and K-Ras G13R, and K-Ras having a mutation at amino acid number 61 such as K-Ras Q61H, K-Ras Q61K, and K-Ras Q61L. Respective PI 3 kinase mutants in particular include PI 3 kinases having an activating mutation in the class I PI 3 kinase catalytic subunit p110α. Furthermore, also patients wherein the tumor is not caused by a deregulation of the EGFR signal transduction pathway may be treated by this antibody composition, as long as the tumor cells express EGFR. Preferably, the antibody composition according to the present invention comprising anti-EGFR antibodies is used in the treatment of colorectal cancer or head and neck cancer, in particular metastatic colorectal cancer or head and neck cancer. Preferably, the anti-EGFR antibody is an anti-EGFR antibody as described above.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

The Method for Producing the Antibody Composition

In a further aspect, the present invention provides a method for producing an antibody composition comprising an antibody or functional fragment or derivative thereof having a desired circulation half-life, comprising the step of expressing said antibody or functional fragment or derivative thereof in a host cell, wherein the method for controlling the half-life of the antibody or fragment or derivative thereof according to the present invention is performed using step (a1), (a3), step (b1) or step (b3) of said method and/or the host cell expresses an antibody or functional fragment or derivative thereof obtained by the method for controlling the half-life of the antibody or fragment or derivative thereof according to the present invention using step (a2) or (b2).

Preferably, the host cell is cultured in a culture medium and accumulates the antibody composition in said culture medium and the antibody composition is recovered from the cell culture medium.

The antibodies or fragments or derivatives thereof in the antibody composition may have any one or more of the features described herein. Furthermore, the antibodies or fragments or derivatives thereof are preferably expressed in a cell line which is capable of producing the glycosylation features desired and/or necessary for controlling the half-life of the antibodies or fragments or derivatives thereof. In particular, the cells and cell lines as disclosed herein can be used for expressing the antibodies or fragments or derivatives thereof. Preferably, human cells or cell lines are used, in particular immortalized human cell lines, such as human blood cell lines, preferably human myeloid cell lines or human myeloid leukemia cell lines.

For the production of antibody compositions comprising antibodies having an increased circulation half-life, the antibodies are preferably expressed in a cell line having a high sialylation activity. An example of such a cell line is the human cell line GT-5s or a cell line derived therefrom or a cell line homologous thereto, preferably as defined above. Antibody compositions comprising antibodies having an increased circulation half-life and an enhanced ADCC activity may be obtained by expressing the antibodies in a cell or cell line having a high sialylation activity and a low fucosylation activity. For example, cell lines derived from GT-5s having a decreased fucosylation activity such as those described above may be used.

The headings provided herein are not limitations of the various aspects or embodiments of this invention which can be had by reference to the specification as a whole.

FIGURES

Figure 5:
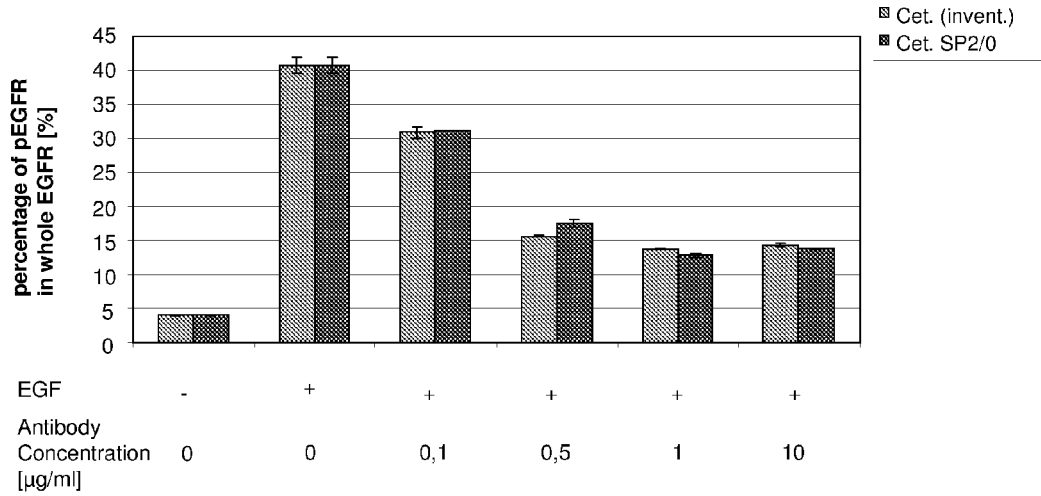
Figure 5:
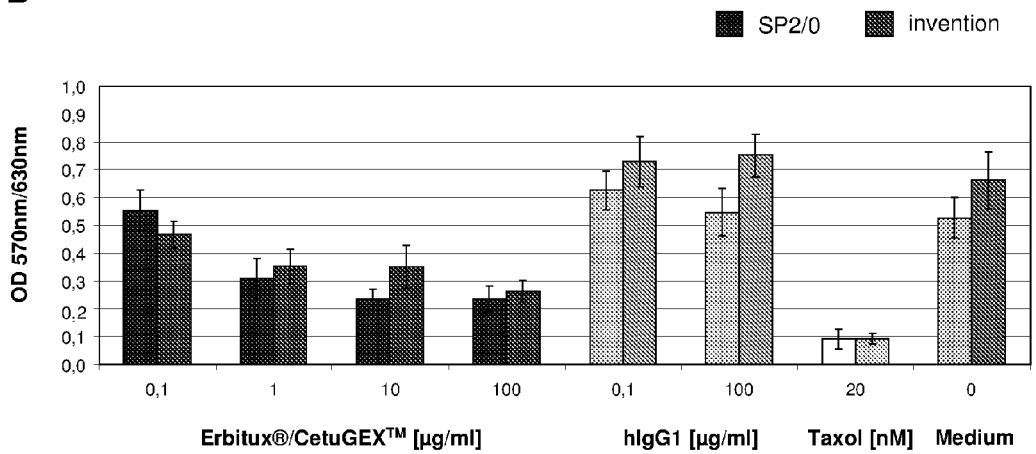

FIG. 5 shows the inhibitory activity of Cetuximab glycosylated according to the invention (Cet. invent.) and Cetuximab expressed in mouse SP2/0 cells (Cet. SP2/0) on EGF receptors. A: Inhibition of EGFR phosphorylation by prevention of ligand binding in the presence of the different Cetuximab variants. The amount of whole EGFR and phosphorylated EGFR was determined in cell lysates using a commercially available kit. Percentage of phosphorylated EGFR in total EGFR is given. Mean values of duplicates ±SD are shown. B: Inhibition of the proliferation of A431 cells by prevention of ligand binding to EGFR in the presence of the different Cetuximab variants. Shown are the mean values of 6 well±SD.

Figure 6:
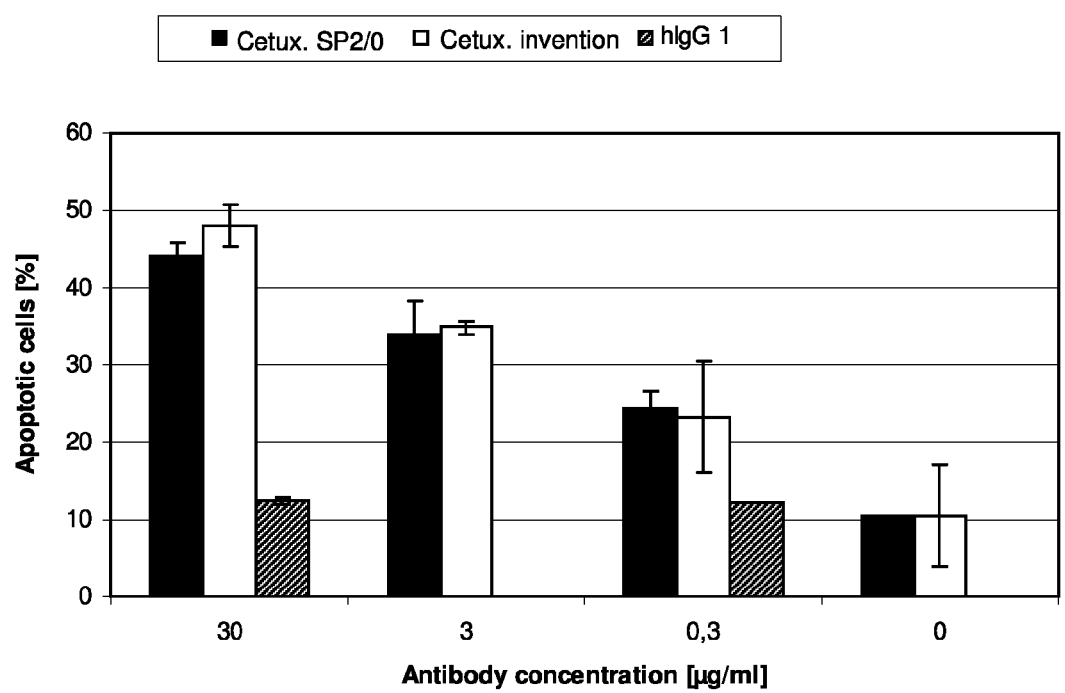

FIG. 6 shows an active caspase-3 apoptosis assay using A431 cells after 18 h incubation with Cetuximab glycosylated according to the invention (Cetux. invention) and Cetuximab expressed in mouse SP2/0 cells (Cetux. SP2/0) and protein G. Mean values of the percentage of caspase-3 positive cells (apoptotic cells)±SD of measurements in duplicates are shown.

Figure 7:
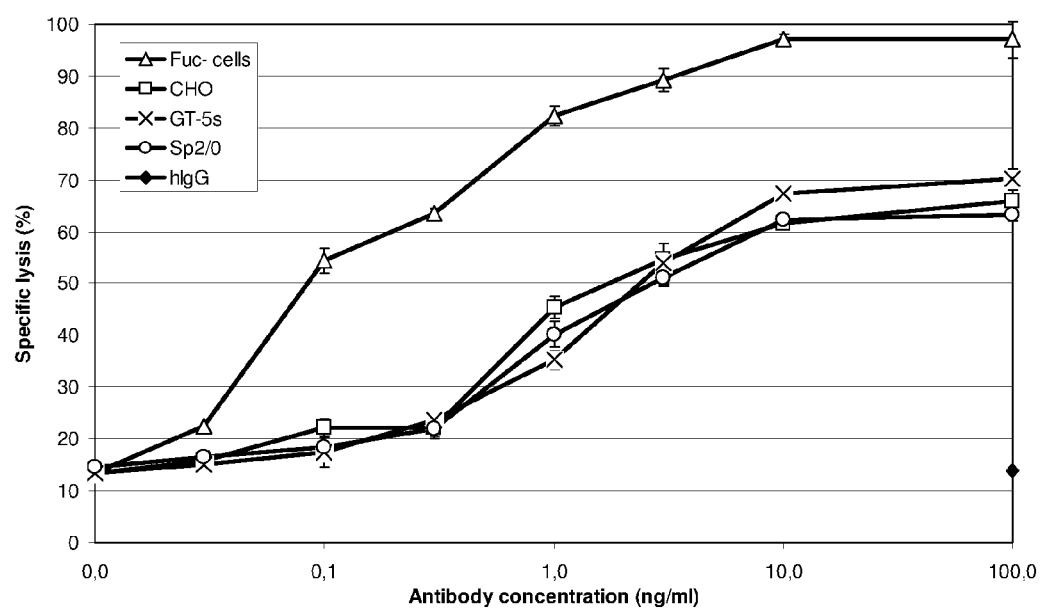

FIG. 7 shows the lysis of target cells by ADCC using Cetuximab expressed in different cell lines.

Figure 8:
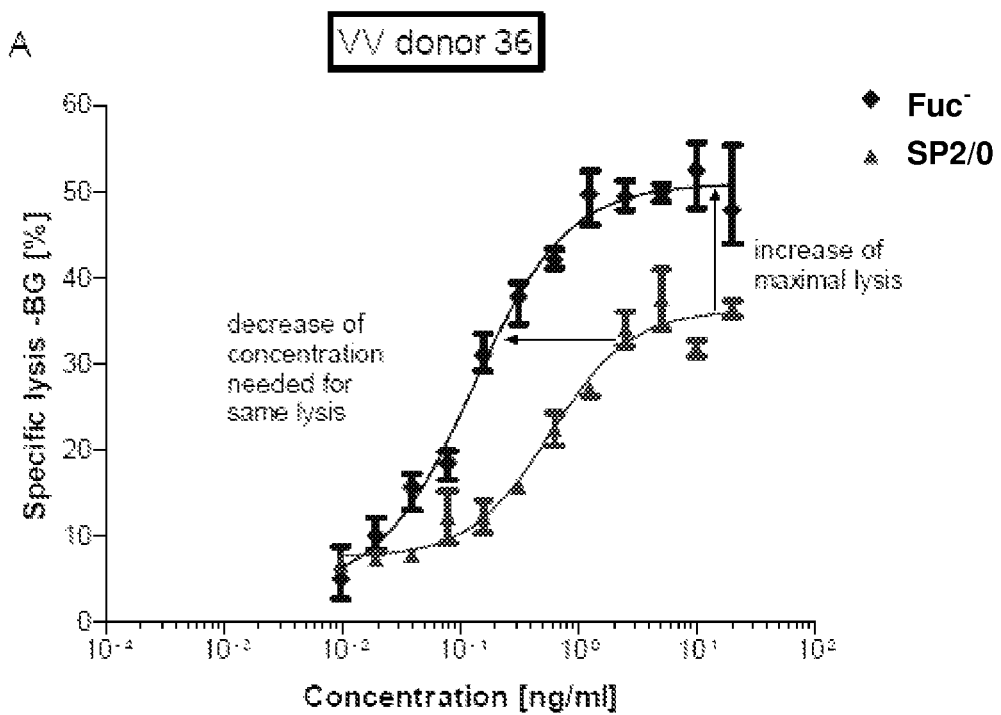

FIG. 8 shows the lysis of target cells by PBMCs obtained from a homozygous FcγRIIIa-158V donor using Cetuximab expressed in a GT-5s derived Fuc⁻ cell line or in SP2/0 cells.

Figure 9:
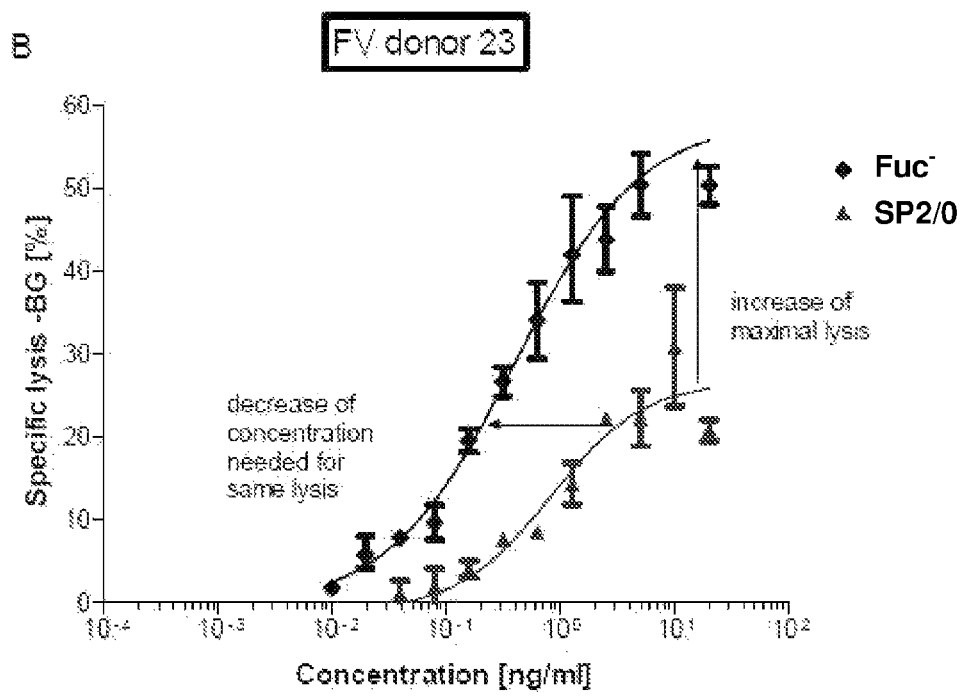

FIG. 9 shows the lysis of target cells by PBMCs obtained from a heterozygous FcγRIIIa-158F/V donor using Cetuximab expressed in a GT-5s derived Fuc⁻ cell line or in SP2/0 cells.

Figure 10:
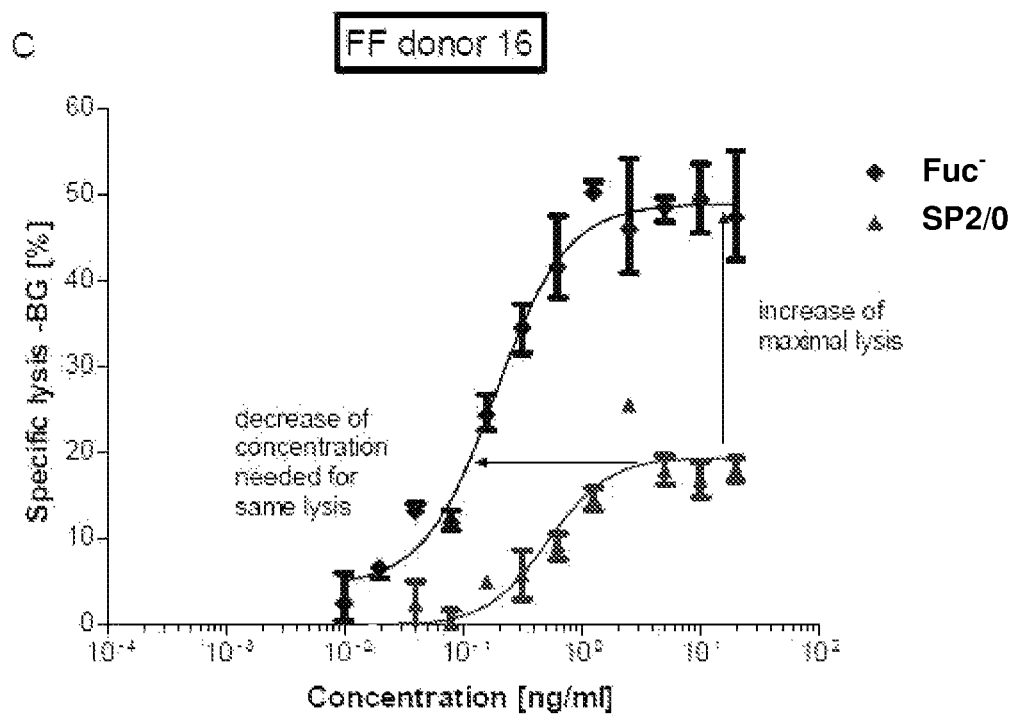

FIG. 10 shows the lysis of target cells by PBMCs obtained from a homozygous FcγRIIIa-158F donor using Cetuximab expressed in a GT-5s derived Fuc⁻ cell line or in SP2/0 cells.

Figure 11:
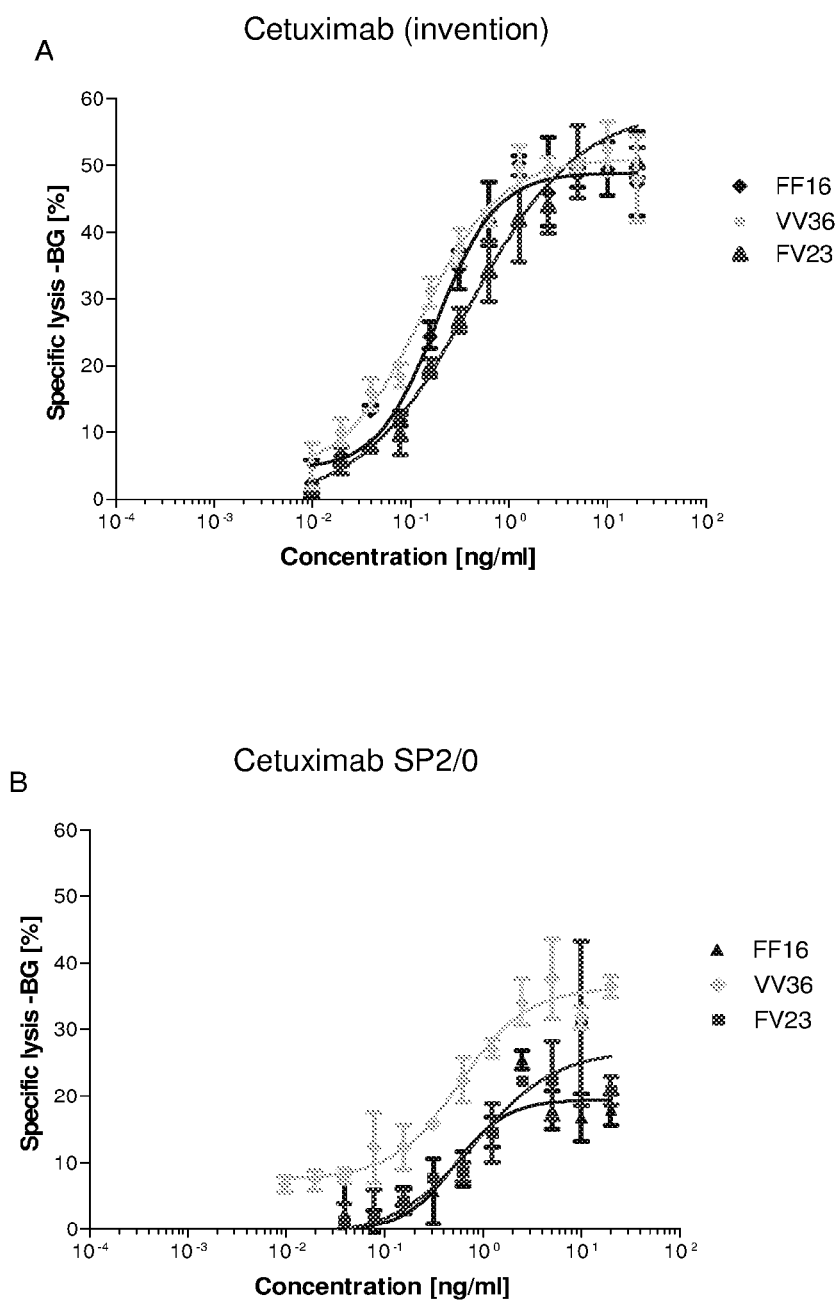

FIG. 11 shows an ADCC assay on LS174T cells with primary human PBMC of donors with different FcγRIIIa allotypes (incubation time 5 h, E:T ratio 80:1, all analyses performed on the same day in parallel). Mean values of specific lysis—specific lysis without antibody (BG) and standard deviation of triplicates are given. A: Cetuximab glycosylated according to the invention; B: Cetuximab expressed in SP2/0 cells.

Figure 12:
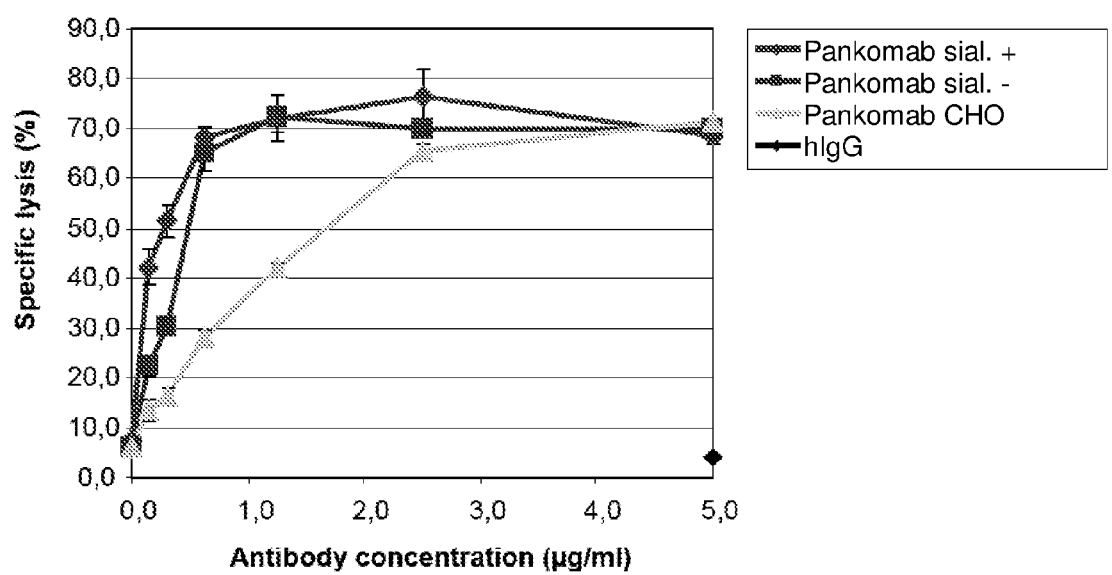

FIG. 12 shows a comparison of ADCC activities of Pankomab expressed in different cells. Europium release assay with ZR-75-1 and human PBMCs at an E:T ratio of 50:1 after incubation with Pankomab from CHO cells (Pankomab CHO), sialylation-deficient human myeloid cells (Pankomab sial.−; lowly sialylated) or GT-5s cells (Pankomab sial.+, highly sialylated) at different concentrations over night.

Figure 13:
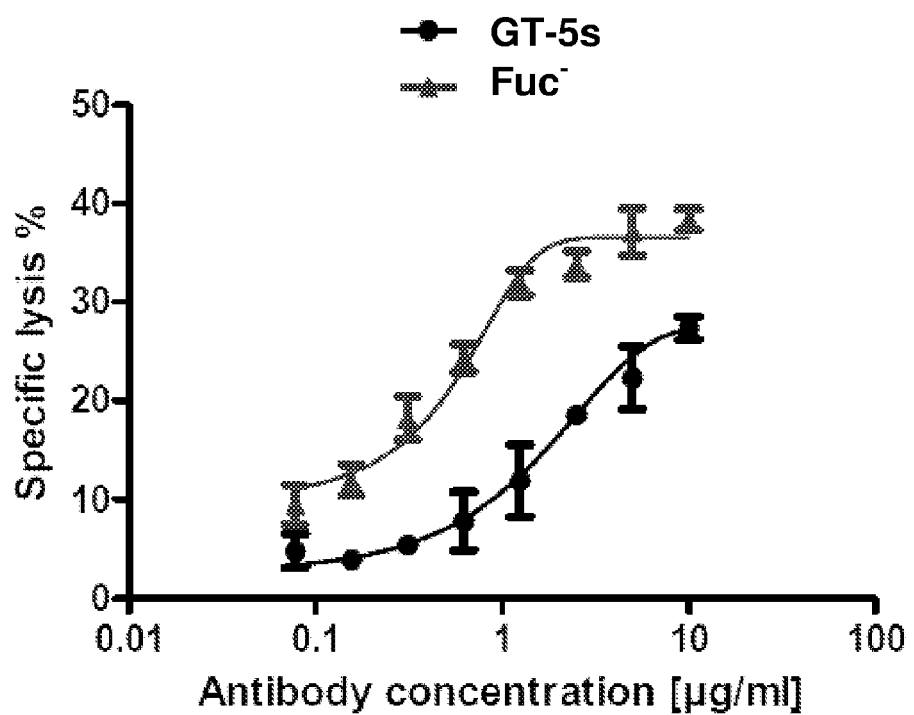

FIG. 13 shows the lysis of target cells by PBMCs obtained from a homozygous FcγRIIIa-158F donor using Pankomab expressed in GT-5s cells or in a GT-5s derived Fuc⁻ cell line.

Figure 14:
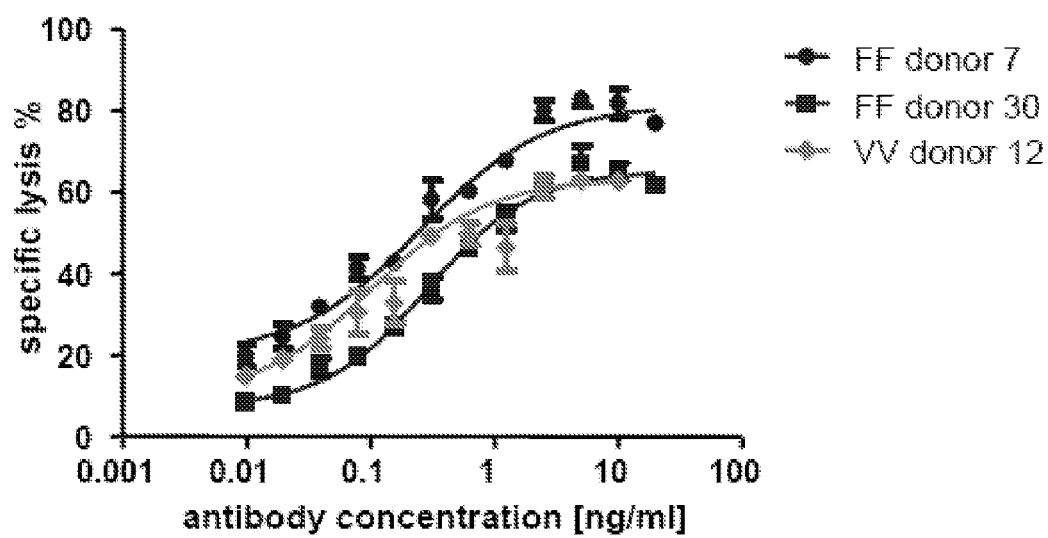

FIG. 14 shows the lysis of target cells comprising a constitutively active K-Ras mutation by PBMCs obtained from homozygous FcγRIIIa-158F or homozygous FcγRIIIa-158V donors using Cetuximab glycosylated according to the invention.

Figure 15:
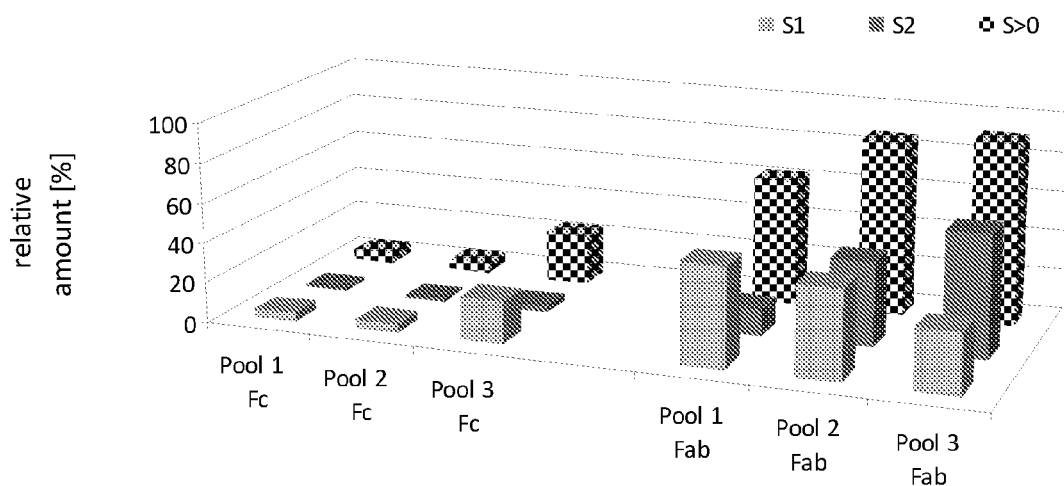
Figure 15:
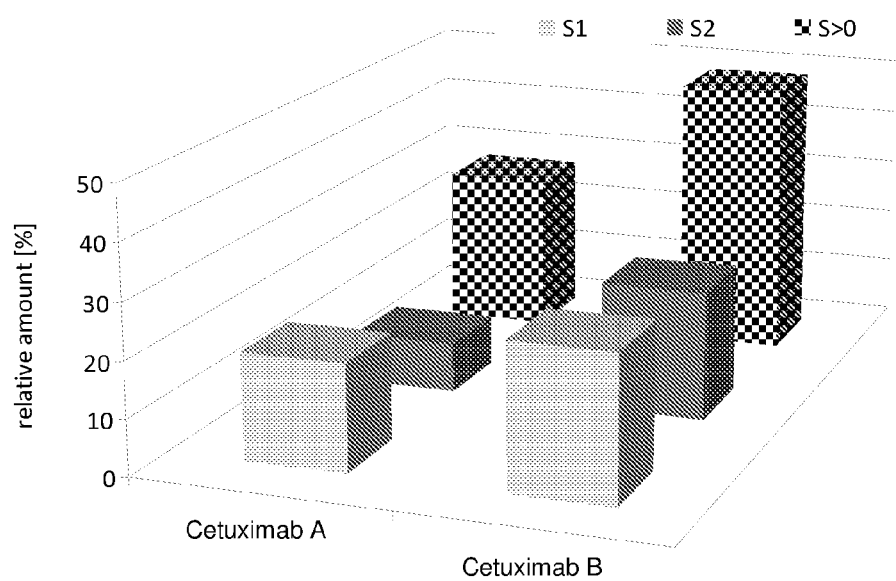

FIG. 15 shows the amount of sialylated glycans in pools of differently charged isotypes. (A) shows the sialylation of the Fc and Fab parts in the pools obtained from chromatofocussing (pool 1: high pH, pool 2: middle pH, pool 3: low pH). (B) shows the sialylation of the pools used for the pharmacokinetic studies (Cetuximab A: pools 1 and 2; Cetuximab B: pool 3). S1 means single sialic acid carrying glycan, S2 means disialylated glycan and S>0 means the sum of S1 and S2.

Figure 16:
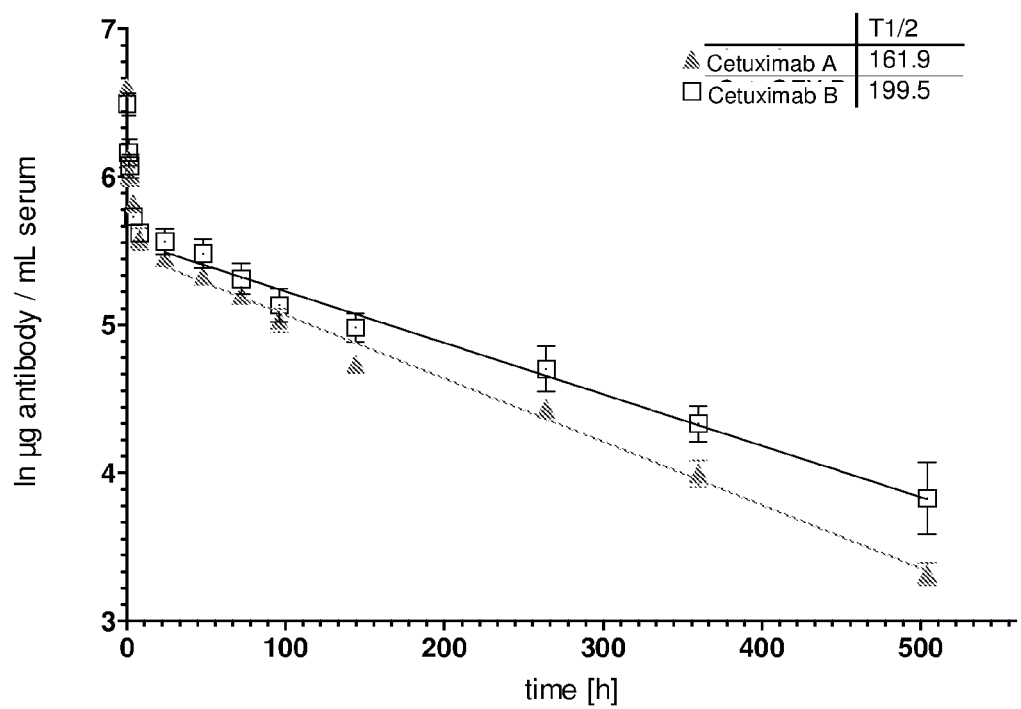

FIG. 16 shows the pharmacokinetic of circulation half-life of Cetuximab in mice. Cetuximab A: low sialylation; Cetuximab B: high sialylation. Antibody concentration is in logarithmic scale.

Figure 17:
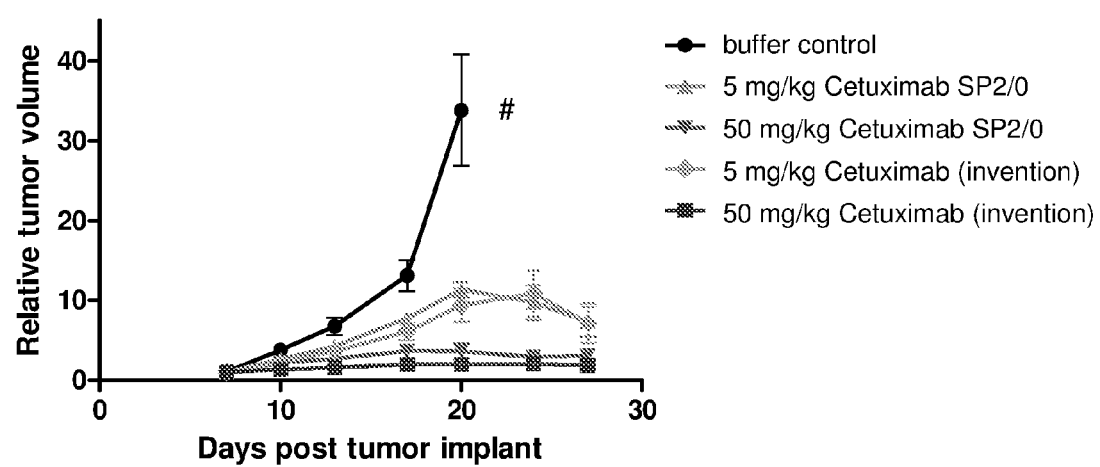

FIG. 17 shows the in vivo anti-tumor activity of Cetuximab glycosylated according to the invention (Cetuximab (invention)) and Cetuximab expressed in mouse SP2/0 cells (Cetuximab SP2/0) in nude mice bearing the A431 human epidermoidal vulva carcinoma xenograft. Xenografted mice were treated at the indicated dosage level when tumors reached palpable size. Each symbol represents the mean value and SEM of a group of 8 animals. #: Because of the critical tumor size the animals of the control group were sacrificed at day 20.

Figure 18:
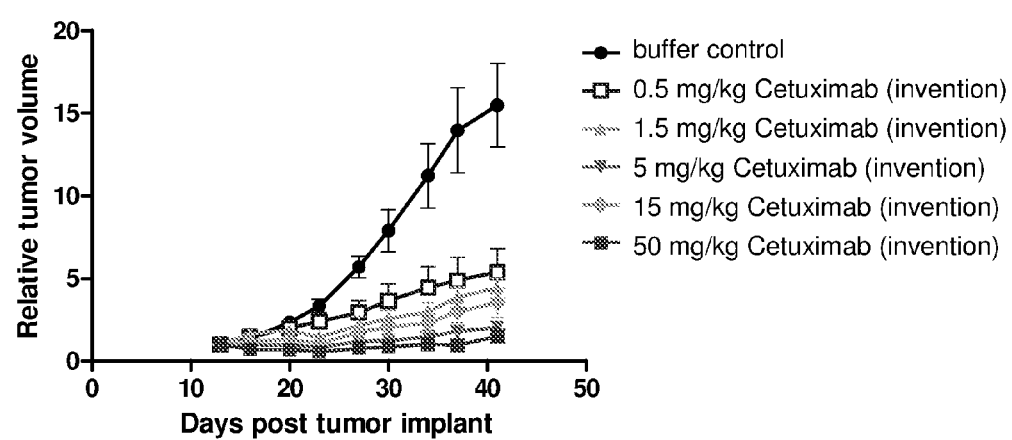

FIG. 18 shows in vivo antitumor activity of Cetuximab glycosylated according to the invention (Cetuximab (invention)) in nude mice bearing the DU145 colon carcinoma xenograft. Xenografted nude mice were treated with Cetuximab (invention) at the indicated dosage level after tumors reached palpable size. Each symbol represents the mean value and SEM of a group of 7-8 animals.

Figure 19:
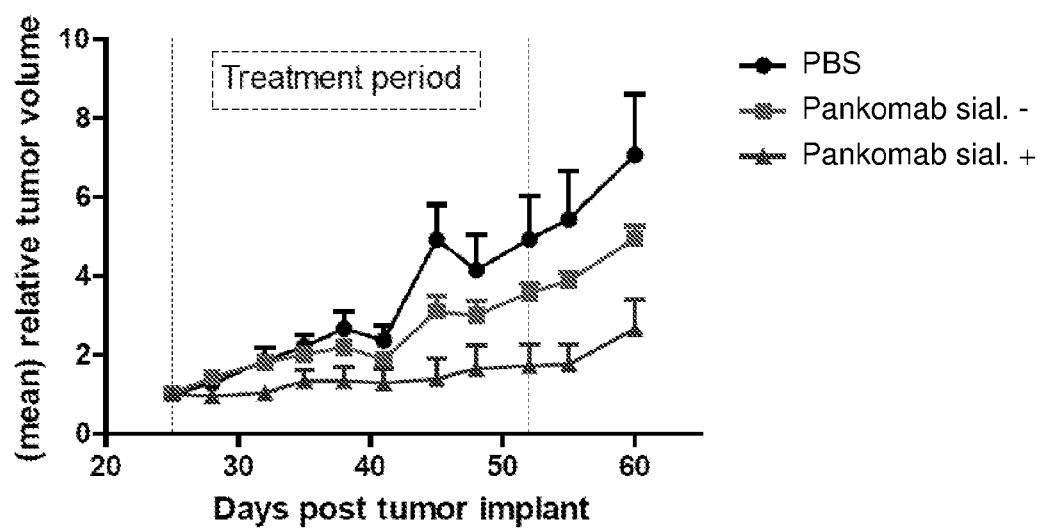

FIG. 19 shows the effect of sialylated Pankomab expressed in GT-5s cells on the tumor growth in ZR-75-1 xenografted nude mice. Groups of 8 mice, nude mice, dose: 0.5 mg/kg, i.v. administration. Pankomab sial.+: sialylated Pankomab; Pankomab sial.−: non-sialylated Pankomab; PBS: buffer control.

Figure 20:
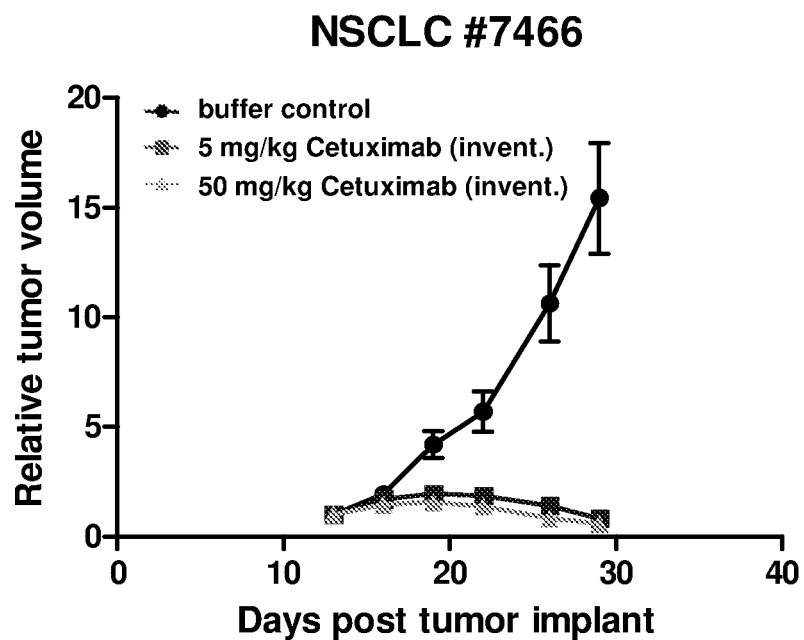
Figure 20:
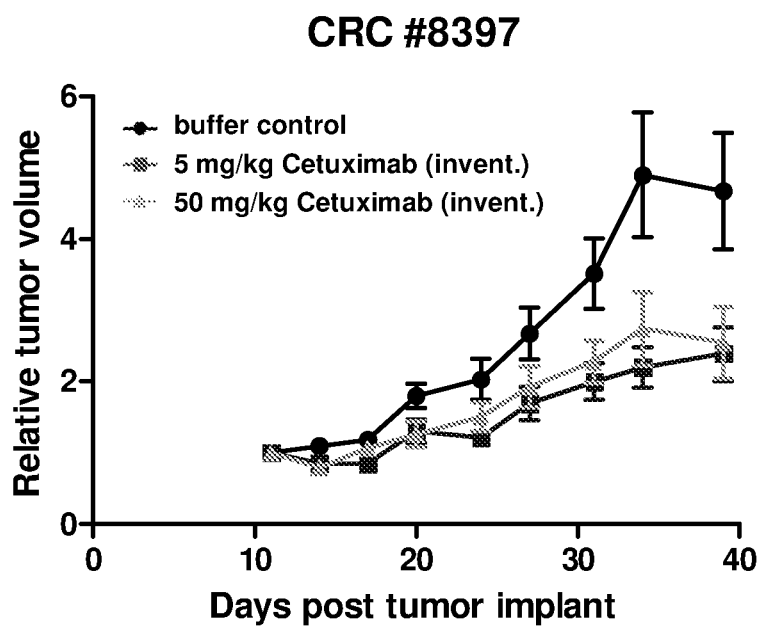

FIG. 20 shows the in vivo antitumor activity of Cetuximab glycosylated according to the invention (Cetuximab (invent.)) in nude mice bearing patient-derived xenografts of NSCLC and CRC origin. Xenografted nude mice were treated with buffer control or different concentrations of Cetuximab (invent.) when tumours reached palpable size. Each symbol represents the mean value and SEM of a group of 8 animals.

Figure 21:
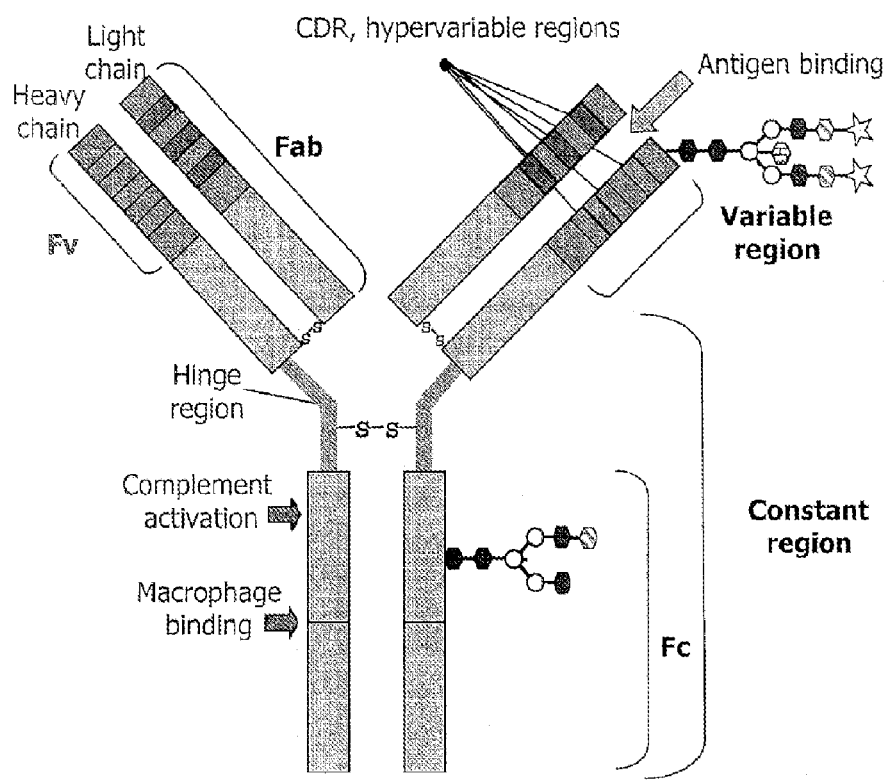
Figure 21:
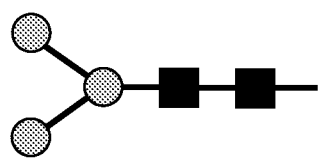
Figure 21:
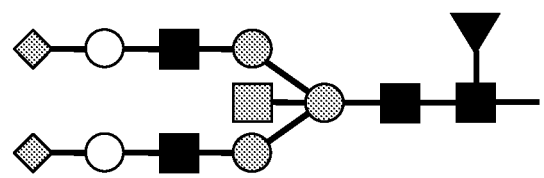

FIG. 21 shows schematic drawings of (A) an IgG antibody and (B) the core structure and (C) the biantennary complex-type structure of the carbohydrate chains which are attached to the Fab- and Fc-glycosylation sites of the antibody. In (A), the IgG antibody comprises exemplary carbohydrate structures at exemplary glycosylation sites. Only the glycosylation of one heavy chain of the antibody is shown. The other heavy chain comprises corresponding glycosylation sites carrying corresponding carbohydrate structures, which are not shown in the schematic drawing. In (B) and (C), a black square represents an N-acetylglucosamine residue (GlcNAc), a gray circle represents a mannose residue (Man), a white circle represents a galactose residue (Gal), a gray rhombus represents a sialic acid residue (SA), a black triangle represents a fucose residue (Fuc) and a gray square represents a bisecting N-acetylglucosamine residue (bisGlcNAc). In the biantennary complex-type structure, GlcNAc, Gal and SA in the branches of the carbohydrate, bisGlcNAc as well as Fuc are only optionally present in the carbohydrate structure and may also be absent.

The percentage values given herein for certain glycosylation properties in particular mean that of all carbohydrates in a composition the indicated percentage has the described property. If the percentage value refers to only a specific group of carbohydrates, for example the carbohydrates attached to the glycosylation site in the Fab part of the antibody in a composition, then it means that of all carbohydrates attached to the glycosylation site in the Fab part of the antibodies in the composition the indicated percentage has the described property. Such glycosylation properties can be determined, for example, by cleaving the antibodies in the composition into their Fab and Fc parts, separating the Fab parts from the Fc parts, cleaving the carbohydrates from the separated Fab and Fc parts, and determining the structures and/or properties of the carbohydrates (separately for the Fab part carbohydrates and the Fc part carbohydrates). Suitable measurement methods from determining the structures and properties are, for example, HPLC methods and mass spectroscopy.

EXAMPLES

Example 1

Glycoprofiling

Anti-EGFR Antibodies

To characterize the glycosylation pattern of the anti-EGFR antibody Cetuximab expressed in a Fuc⁻ cell line which was derived from the human immortalized blood cell line GT-5s (Fuc⁺) or in the mouse cell line SP2/0 (Erbitux) in more detail glycoprofiling studies were performed. The human/mouse chimeric IgG antibody Cetuximab comprises one N-glycosylation site in framework region 3 of the heavy chain variable region and one N-glycosylation site in the heavy chain constant region 2.

The antibodies were cleaved with papain resulting in the generation of one Fc fragment and two Fab fragments. Separation of the fragments was performed employing affinity chromatography on a protein A solid phase which binds Fc fragments, but not Fab fragments. After separation of the Fc from the Fab part, the N-glycans of each fragment were applied for glycoprofiling.

For glycoprofiling, the intact N-glycans were released from the protein core and the reducing ends of N-glycans were labeled with a fluorescence marker. The purified sample of the labeled N-glycans was separated by HPLC.

Peak areas based on fluorometric detection were employed for calculation of the relative molar abundances of the N-glycan structures. Estimated data for both antibodies are summarized in Table 1. The values represent the relative molar contents of N-glycans containing the interesting type of monosaccharide (e.g. fucose).

TABLE 1

| Sample | Rel. abundance [mol %]* | | | | | | | | | |
|---|---|---|---|---|---|---|---|---|---|---|
| Cetuximab | F | S0 | S > 0 | S1 | S2 | G0 | G1 | G2 | B | Galili |
| Fuc⁻ Fc | 8 | 95 | 4 | 4 | 0 | 20 | 48 | 31 | 23 | 0 |
| Fuc⁻ Fab | 40 | 15 | 78 | 65 | 13 | 1 | 8 | 85 | 71 | 0 |
| SP2/0 Fc | 98 | 100 | 0 | 0 | 0 | 55 | 38 | 6 | 3 | 0 |
| SP2/0 Fab | 78 | 43 | 37 | 30 | 7 | 2 | 2 | 75 | 6 | 56 |

*Relative abundances of glycan structures are related to the total amount of N-glycans. Since not all glycan structures could be assigned, the sum of the relative abundances of sialylated and non sialylated or galactosylated and non galactosylated glycan structures does not give 100% in every case.
F = fucosylated N-glycans; S0 = non-sialylated N-glycans; S > 0 = sialylated N-glycans; S1 = monosialylated N-glycans; S2 = disialylated N-glycans; G0 = non-galactosylated N-glycans, G1 = monogalactosylated N-glycans, and G2 = digalactosylated N-glycans, B = bisecting N-acetylglucosamine, Galili = Gal-1,3-Gal.

The glycoprofiling shows that Cetuximab antibodies expressed in Fuc⁻ cells derived from GT-5s have a much lower average fucose content in the Fc glycosylation, a higher average sialic acid content in the Fab glycosylation and a higher average bisGlcNAc content in the Fc as well as the Fab glycosylation compared to Cetuximab antibodies expressed in mouse SP2/0 cells. Furthermore, only the Cetuximab antibodies expressed in SP2/0 cells comprises the Galili epitope which is responsible for adverse side effects in humans.

Furthermore, the relative amounts of NeuGc and NeuAc in the two different Cetuximab preparations were determined. The immunogenic 5-N-glycolylneuraminic acid (NeuGc) can be distinguished from 5-N-acetylneuraminic acid (NeuAc) by reverse phase chromatography (RP-HPLC).

For the analysis, sialic acids were released from protein. Free sialic acids were labeled with a fluorophore and analyzed by means of RP-HPLC employing fluorometric detection. Labeled NeuAc and NeuGc differ in the retention times on RP-HPLC. Commercially available standards were used for the identification of these compounds. Table 2 summarizes the results. For SP2/0-expressed Cetuximab, both sialic acids were identified, with a high dominance of 5-N-glycolylneuraminic (96%) over 5-N-acetylneuraminic acid (4%). In contrast, only 5-N-acetylneuraminic acid was detectable for Cetuximab according to the present invention expressed in the human GT-5s-derived Fuc⁻ cell line.

TABLE 2

| | Rel. molar amount [mol %] | |
|---|---|---|
| Sample | NeuAc | NeuGc |
| Fuc⁻ | 100 | 0 |
| SP2/0 | 4 | 96 |

In the following experiments, Cetuximab expressed in GT-5s cells or in a Fuc⁻ cell line derived from GT-5s cells was used as an example of the antibodies according to the present invention having an improved glycosylation pattern, in particular a high sialylation degree at the Fab part, a high amount of bisecting GlcNAc and optionally a low amount of fucose at the Fc part. Cetuximab expressed in SP2/0 cells (Erbitux) was used as negative control as it shows a significantly lower sialylation at the Fab part.

Anti-MUC1 Antibodies

A similar glycoprofiling was performed with the TA-Muc-1 antibody Pankomab expressed in GT-5s and a Fuc⁻ cell line derived from GT-5s. A humanized version of the IgG antibody Pankomab (hPM) having an N-glycosylation site in the CDR2 of the heavy chain variable region and an N-glycosylation site in the heavy chain constant region 2 was used.

TABLE 3

| Sample | F | S | G | B |
|---|---|---|---|---|
| hPM (GT-5s) | 84 | 38 | 81 | n.d. |
| hPM Fab (GT-5s) | 78 | 71 | 93 | n.d. |
| hPM Fc (GT-5s) | 86 | 3 | 70 | n.d. |
| hPM (Fuc⁻) | 31 | 37 | 82 | 28 |

F = fucosylated N-glycans;
S = sialylated N-glycans;
G = galactosylated N-glycans;
B = bisecting N-acetylglucosamine;
n.d. = not determined The Fuc⁻ cell line derived from the GT-5s cell line produces Pankomab antibodies having a highly similar sialylation pattern and galactosylation pattern while the amount of fucose is markedly decreased. The low average amount of fucosylated carbohydrates in the entire Fuc⁻-expressed Pankomab antibodies indicates an even lower average amount of fucose-carrying Fc glycosylations. The amount of bisecting GlcNAc residues was not determined in the glycoanalysis performed with humanized Pankomab obtained from GT-5s cells.

A further glycoanalysis of the antibody Pankomab expressed in GT-5s was performed, using improved detection and analysis procedures. The following results were obtained:

TABLE 4

| Sample | Rel. abundance [mol %]* | | | | | | | | | |
|---|---|---|---|---|---|---|---|---|---|---|
| | F | S0 | S > 0 | S1 | S2 | G0 | G1 | G2 | B | Galili |
| Pankomab Fc | 83 | 84 | 6 | 5 | 1 | 27 | 44 | 20 | 26 | 0 |
| Pankomab Fab | 92 | 15 | 79 | 44 | 35 | 2 | 3 | 89 | 65 | 0 |

*Relative abundances of glycan structures are related to the total amount of N-glycans. Since not all glycan structures could be assigned, the sum of the relative abundances of sialylated and non sialylated or galactosylated and non galactosylated glycan structures does not give 100% in every case.
F = fucosylated N-glycans; S0 = non-sialylated N-glycans; S > 0 = sialylated N-glycans; S1 = monosialylated N-glycans; S2 = disialylated N-glycans; G0 = non-galactosylated; N-glycans; G1 = monogalactosylated N-glycans; and G2 = digalactosylated N-glycans, B = bisecting N-acetylglucosamine; Galili = Gal-1,3-Gal.

Example 2

Antigen Binding Studies

Antigen ELISA

A specific antigen ELISA (enzyme linked immunosorbent assay) was developed for the anti-EGFR antibody Cetuximab with the commercially available antigen EGFR immobilized on Maxisorp 96 well plates. Coated wells were blocked with 2% BSA in PBS to prevent unspecific binding of anti-bodies. Anti-EGFR antibodies, diluted in 1% BSA/PBS, were incubated to the immobilized antigen for binding and detected by an enzyme-labeled secondary anti-human IgG antibody. The enzyme POD converts the substrate TMB into a dye, which was quantified photometrically after acidification with diluted sulfuric acid at 450 nm.

Cetuximab expressed in mouse SP2/0 cells (Erbitux (Merck)) was used for calibration in the range of 1 to 10 ng/ml. Samples comprising Cetuximab glycosylated according to the invention were diluted to 4 and 8 ng/ml and compared to the calibration curve (quadratic equation fit). The results of different Cetuximab probes show that binding of both antibodies in the ELISA is comparable.

Kinetics and Affinity (Surface Plasmon Resonance)

Sensor chip CM5 was covalently coated by amine coupling with the extracellular domain of commercially available EGFR. Cetuximab expressed in mouse SP2/0 cells (Erbitux; having a low sialylation degree) and two preparations of Cetuximab glycosylated according to the invention ran simultaneously over two flow cells, coated with different ligand densities, resulting in Rmax of about 25 and 100 RU, respectively. The anti-EGFR antibodies were injected in a broad range of concentrations (2 nM to 1 μM) to calculate binding kinetics. Since an antibody has two binding sites, a bivalent evaluation model was used. Results are shown in Table 5. The association constant $k_{a1}$ and the dissociation constant $k_{d1}$ are the relevant constants as could be shown in Biacore's simulation software BIASimulation 2.1. Therefore these two constants were used to calculate an affinity constant $K_D$. Taking the results of all experiments with the very low and slightly higher coated flow cells together, the $K_D$ for both Cetuximab variants are comparable with the $K_D$ of the Cetuximab variant according to the invention being even slightly better (a lower $K_D$-value indicates a stronger antigen binding).

TABLE 5

|  | Cetuximab (invention) | Erbitux |
|---|---|---|
| $k_a1$ [1/Ms] | 3.73e5 | 3.29e5 |
| $k_d1$ [1/s] | 3.35e−3 | 4.21e−3 |
| $k_a2$ [1/RUs] | 0.527 | 1.28 |
| $k_d2$ [1/s] | 0.298 | 0.536 |
| $K_D = k_d1/k_a1$ [nM] | 9 | 13 |

Tumor Cell Binding in Flow Cytometry

Several EGF-receptor positive cell lines were analyzed by flow cytometry to investigate and to compare the binding properties of the anti-EGFR antibody Cetuximab glycosylated according to the invention and Cetuximab having a low sialylation degree (expressed in mouse SP2/0 cells). Briefly, target cells were harvested and incubated with the anti-EGFR antibody at different concentrations. Cells were washed and incubated with a secondary Cy3-conjugated anti-human IgG antibody at 4° C. in the dark. Cells were washed again and analyzed in a flow cytometer FACS Canto II (Becton Dickinson). Live cells were gated based on their scatter properties and the percentage of positive cells was calculated using the FACSDiva Software (Becton Dickinson).

Figure 1:
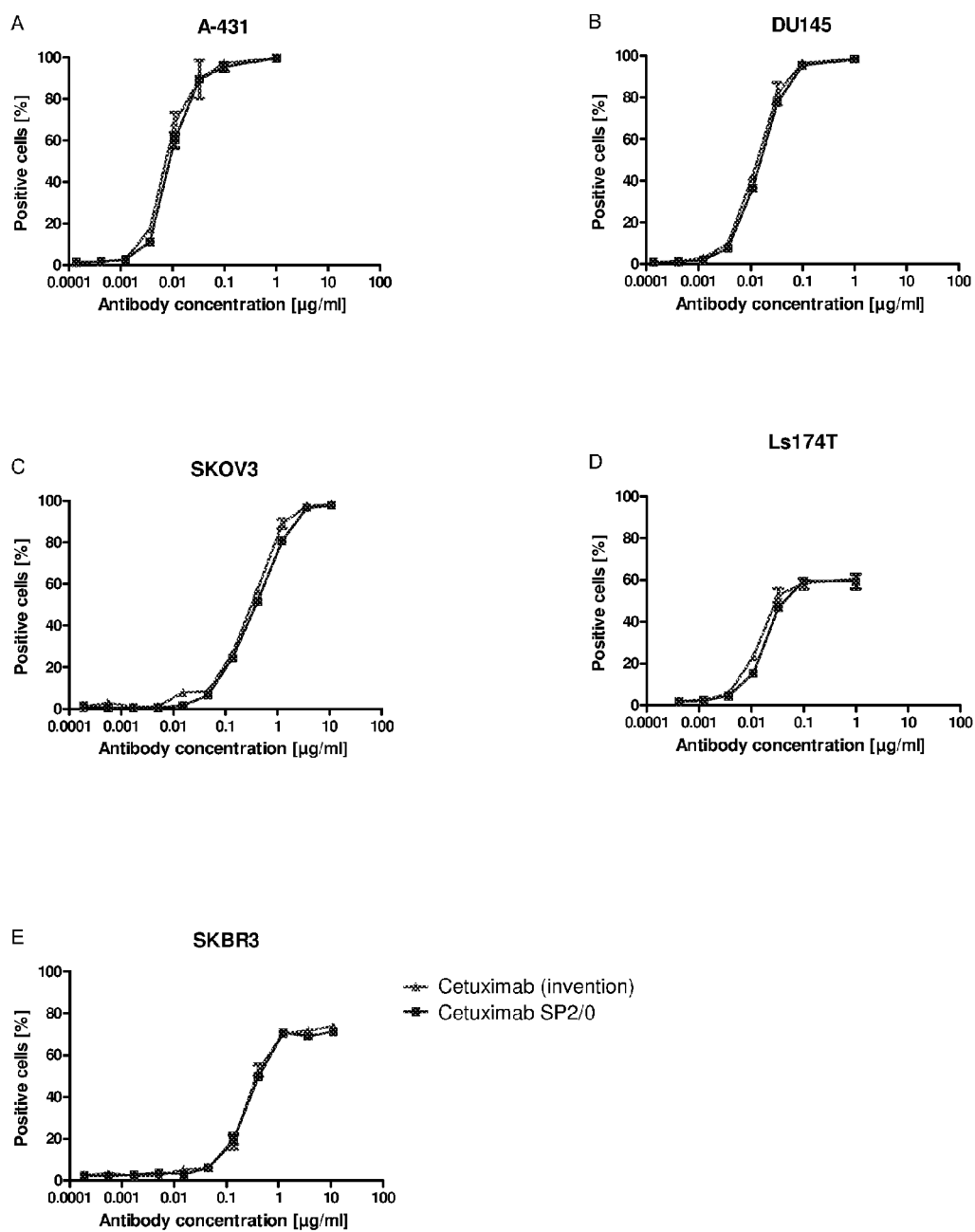
FIG. 1 shows the binding of the anti-EGFR antibody Cetuximab glycosylated according to the invention (Cetuximab (invention)) and Cetuximab expressed in mouse SP2/0 cells (Cetuximab SP2/0) on different cell lines analyzed by flow cytometry. Mean values of duplicates±SD are shown.

Cetuximab glycosylated according to the invention and Cetuximab expressed in mouse SP2/0 cells show comparable binding characteristics on all tumor cell lines tested as shown in FIG. 1.

Scatchard Analysis

Two factors are particularly important for the therapeutic suitability of an antibody: the affinity and number of binding sites for an antibody on tumor cells.

The affinity of a receptor-ligand binding describes the strength of their interaction. In the case of antigen-antibody interactions it is defined by the chemical equilibrium of free antibodies/antigens and the formed antibody-antigen complex. This equilibrium is also the ratio of the on-rate and off-rate and is influenced by different parameters like e.g. hydrogen bonds, electrostatic interactions, hydrophobic and Van der Waals forces. The Scatchard analysis is commonly used for calculating the affinity constant of ligand-receptor binding. The Scatchard equation is given by $$\frac{r}{c} = nK_a - rK_a$$

where r is the ratio of the concentration of bound ligand to total available binding sites, c is the concentration of free ligand, and n is the number of binding sites per protein molecule.

Assuming a monovalent interaction and plotting this data, r/c vs r, yields a linear Scatchard plot with a slope $-K_a$ and a Y-intercept of $nK_a$. In case of cell-binding studies (were cells refer to the antigen), the number of antibodies bound per cell can be calculated from the X-intercept.

Binding of the anti-EGFR antibody Cetuximab glycosylated according to the invention and expressed in mouse SP2/0 cells to tumor cell lines was evaluated using radiolabeled antibodies in cell binding studies. The antibodies were chelated with p-SCN-Benzyl-DTPA and radiolabeled with carrier-free $^{111}$In. Dissociation constant and antibody binding sites were estimated by Scatchard plot analysis.

Binding experiments were performed with both antibodies under comparable conditions. The human tumor cell lines A431, LS174T and DU145 were used to investigate and to compare the binding properties of both antibodies. Experimentally, aliquots of cells (equal number per vial) were incubated with increasing amounts of the different $^{111}$In-radiolabeled antibody preparations, allowed to equilibrate, and afterwards separated from the unbound antibody. The quantity of cell-bound antibody was determined by radioactivity measurement and the data were evaluated as described above.

As a result, comparable affinities and number of binding sites were estimated by Scatchard plot analysis. Table 6 summarizes the results of cell binding experiments.

TABLE 6

| | Dissociation constant $K_D$ [M] | | Number of binding sites per cell | |
|---|---|---|---|---|
| Tumor cell line | Cetuximab (inv.) | Cetuximab SP2/0 | Cetuximab (inv.) | Cetuximab SP2/0 |
| A431 | $1.3 \times 10^{-9}$ | $0.8 \times 10^{-9}$ | $6.9 \times 10^5$ * | $5.1 \times 10^5$ |
| LS174T | $2.3 \times 10^{-10}$ | $2.3 \times 10^{-10}$ | $1.1 \times 10^4$ | $5.2 \times 10^4$ |
| DU145 | $0.9 \times 10^{-9}$ | $0.4 \times 10^{-9}$ | $1.7 \times 10^5$ | $1.2 \times 10^5$. |

The values (for LS174T, DU145) represent a mean of at least two individual sets of experiments. The number of binding sites per cell refers to the number of antibody molecules bound per cell and not to the number of receptor binding places on the cell surfaces.

The results show that the affinity and number of binding sites of Cetuximab glycosylated according to the invention (Cetuximab (inv.)) and Cetuximab expressed in mouse SP2/0 cells (Cetuximab SP2/0) towards tumor cells are comparable.

A similar scatchard analysis was performed for the anti-MUC1 antibody Pankomab. Analogous experiments were performed with Pankomab expressed in CHO-cells and Pankomab expressed in GT-5s cells, each purified by chromatography on protein A. The human tumor cell line ZR-75-1 was used to investigate and to compare the binding properties of the Pankomab antibodies (all IgG1 antibodies of same specificity) expressed in different cells.

Experimentally, aliquots of cells (equal number per vial) were incubated with increasing amounts of the different antibody preparations ($^{111}$In-radiolabelled Pankomab was used for quantification), allowed to equilibrate, and afterwards separated from the unbound antibody. Quantity of cell-bound antibody was determined by radioactivity measurement and the data are evaluated as described above. Table 7 summarizes the data. As a result comparable binding was measured for the differently glycosylated Pankomab variants.

TABLE 7

| Antibody | Dissociation constant $K_D$ [M] | Number of binding sites per cell |
|---|---|---|
| PankoMab expressed in CHO | $7.8 \times 10^{-9}$ | $8.2 \times 10^5$ |
| PankoMab expressed in GT-5s | $3.33 \times 10^{-9}$ | $6.7 \times 10^5$ |

Summary

In conclusion, the above experiments demonstrate that the improved glycosylation pattern of the antibodies according to the present invention, in particular the increased sialylation degree at the Fab part of the antibody, does not negatively influence its antigen binding properties.

Example 3

Circulation Half-Life of Differently Glycosylated Antibodies

To test the circulation half-life of differently glycosylated antibodies, a pharmacokinetic assay was performed.

Figure 2:
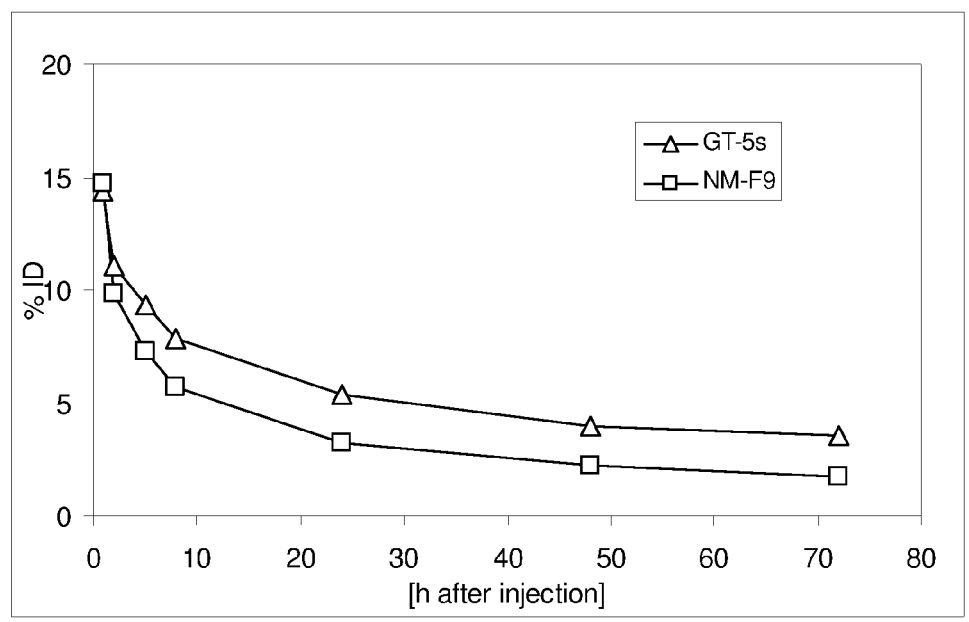
FIG. 2 shows the pharmacokinetics of Pankomab expressed in GT-5s cells or NM-F9 cells in rats.

For this assay, 15 μg of protein A-purified anti-TA-Muc1 antibody Pankomab were injected into rats and the amount of antibody in the rat's serum was determined at specific time points. Pankomab expressed in GT-5s cells was compared to Pankomab expressed in the human immortalized blood cell line NM-F9 (DSM ACC2606 disclosed e.g. in WO 2005/017130 A; Fuc$^+$, sialic acid). The results are shown in FIG. 2.

As can be seen, antibodies having a high degree of sialylation at the Fab part (GT-5s) have a much higher circulation half-life than antibodies having a low sialylation degree (NM-F9).

Figure 3:
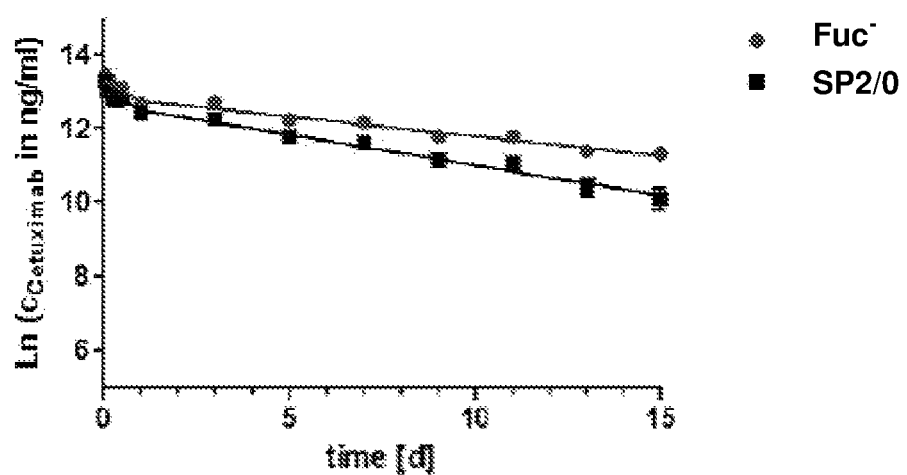
FIG. 3 shows the pharmacokinetics of Cetuximab expressed in Fuc⁻ cells derived from GT-5s or SP2/0 cells in cynomolgus monkeys.

In a further pharmacokinetic assay, the circulation half-life of the anti-EGFR antibody Cetuximab expressed in a Fuc$^-$ cell line derived from GT-5s cells and expressed in mouse SP2/0 cells was tested in an in vivo cynomolgus monkey assay. The results are shown in FIG. 3. Therein, it is again demonstrated that antibodies having a high degree of sialylation at the Fab part (GT-5s-derived Fuc$^-$ cell line) have a much higher circulation half-life than antibodies having a low sialylation degree (SP2/0):

TABLE 8

| | $C_{max}$ [μg/mL] | $t_{1/2}$ [h] | $AUC_{0-\infty}$ [μg*h/mL] |
|---|---|---|---|
| Cetuximab (invention) | 664 ± 53 | 110 ± 28 | 74600 ± 18400 |
| Cetuximab (SP2/0) | 589 ± 58 | 68 ± 7 | 46400 ± 2800 |

Thus, by increasing the amount of sialic acid in the Fab glycosylation, the circulation half life was considerably increased.

In a third pharmacokinetic assay, the circulation half-life of the chimeric human/mouse IgG antibody Cetuximab having a glycosylation site in the Fab part and a glycosylation site in the Fc part is compared to the circulation half-life of the humanized version of this antibody wherein the glycosylation site in the Fab part was removed and which only comprises the glycosylation site in the Fc part. Both antibodies have been expressed in a Fuc$^-$ cell line derived from GT-5s cells.

Figure 4:
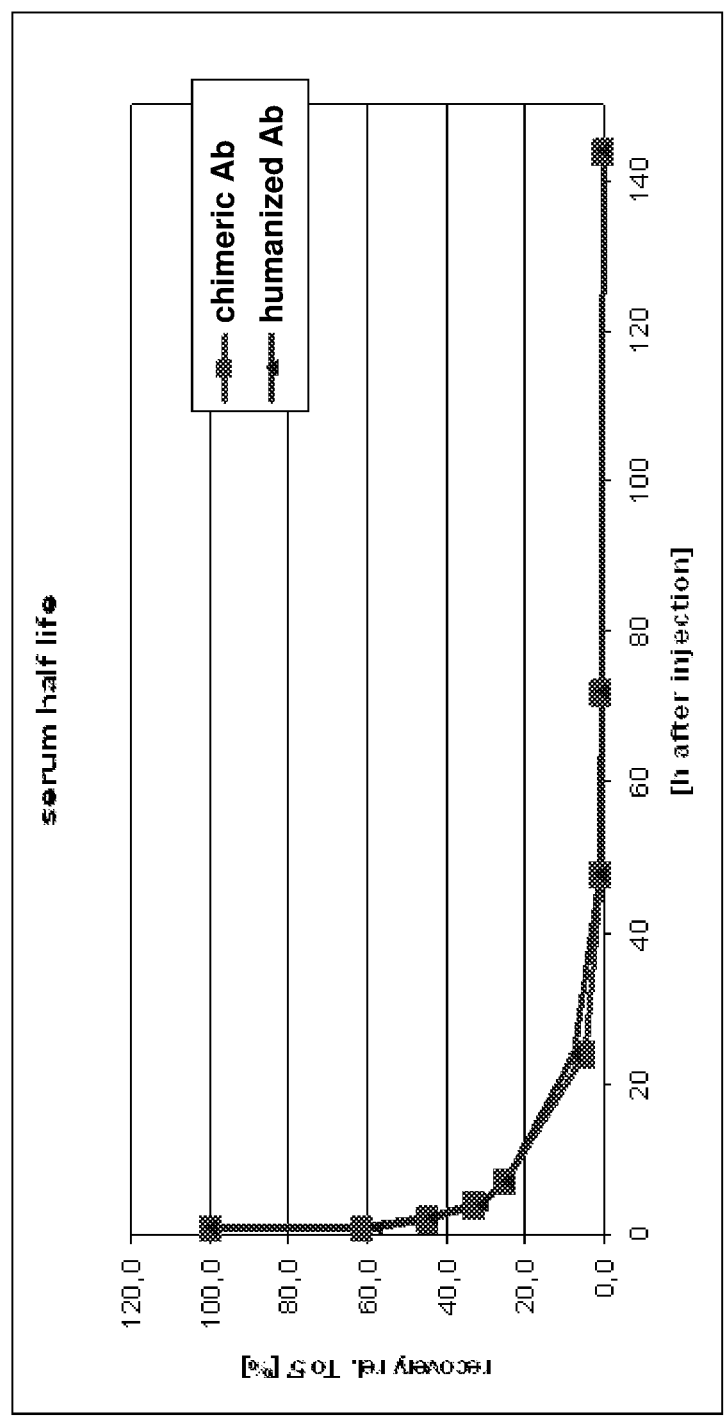
FIG. 4 shows the pharmacokinetics of chimeric Cetuximab having a Fab and a Fc glycosylation site and humanized Cetuximab only having a Fc glycosylation site, expressed in Fuc⁻ cells derived from GT-5s.

10 μg antibody/mouse were injected into mice and the relative amount of antibody recovered after the indicated time was detected. Tests were done in triplicate. The results are shown in FIG. 4. It is demonstrated that the humanized antibody which does not have a Fab glycosylation site has an identical circulation half-life compared to the chimeric antibody comprising highly sialylated carbohydrates attached to its Fab glycosylation site. This demonstrates that also the removal of the Fab glycosylation site results in an increase of the half-life as is taught herein.

In conclusion, the above experiments show that the circulation half-life of an antibody having a Fab glycosylation with a low sialic acid content can be increased by either increasing the amount of sialic acid in the carbohydrates attached to the Fab part or by removing the glycosylation site present in the Fab part.

Example 4

EGF Receptor Inhibition by Differently Glycosylated Anti-EGFR Antibodies

Activation of the EGFR by native ligands (e.g. EGF or TNF alpha) leads to receptor dimerization, stimulation and phosphorylation of the intracellular kinase domain. The signaling cascade which is induced in the nucleus induced thereby activates cell proliferation. One mechanism of action of the anti-EGFR antibody Cetuximab is the prevention of the EGF-induced phosphorylation of the intracellular kinase domain of the EGFR thereby abolishing the signal transduction in the nucleus. These result in an inhibition of EGF induced proliferation of EGFR positive cell lines.

Inhibition of EGFR Phosphorylation

In order to analyze the effects of differently glycosylated Cetuximab antibodies on EGFR phosphorylation, an EGFR phosphorylation assay was performed. Briefly, A431 (human epidermoid carcinoma cell line of the vulva) cells or LS174T (human epithelial colon adenocarcinoma) cells were starved from EGF by serum depletion for 24 hours. Cells were incubated with different concentrations of different Cetuximab versions (0.1-10 μg/ml) for 4 hours and stimulated with 0.1 μg/ml EGF for 15 min. Lysates of the cells were prepared and the content of whole EGFR and phosphorylated EGFR (p-EGFR) was determined using a commercially available p-EGFR/whole EGFR-Kit (Mesoscale discoveries) according to manufacturers protocols, which enables the simultaneous detection of EGFR and phosphorylated EGFR within the same well. In the p-EGFR/whole EGFR-kit, the plates are precoated with an antibody specific for phosphorylated EGFR (Tyr1173) on one spot of the well and an antibody recognizing phosphorylated and unphosphorylated (whole) EGFR in another spot of the same well. After blocking and washing, the plates were incubated with the lysates, plates were washed and bound EGFR was detected with a Sulfo-tag labeled secondary antibody. Electrochemiluminecence for each spot was measured separately at a SectorImager S16000 (Mesoscale discoveries). The percentage of the signal in the pEGFR spot was calculated in comparison to the signal in the spot for whole EGFR (same well).

FIG. 5A shows the results of an assay measuring EGFR phosorylation after EGF stimulation of the EGFR-positive cell line A431 in the absence and presence of Cetuximab glycosylated according to the invention (Cetuximab (invention)) and Cetuximab expressed in mouse SP2/0 cells (Cetuximab SP2/0). A concentration-dependent reduction of the percentage of phosphorylated EGFR was determined. At 1 and 10 μg/ml Cetuximab, there is only one third of the amount of phosphorylated EGFR found compared to that without antibody incubation. The reduction of EGFR phosphorylation was comparable for both Cetuximab variants. Similar results were obtained using the EGFR-positive cell line LS174T. As a result Cetuximab having the improved glycosylation pattern according to the present invention inhibits the EGFR phosphorylation of the intracellular kinase domain on the same level as the commercially available Cetuximab (Erbitux) under the conditions used.

Inhibition of Proliferation

Binding of Cetuximab on the extracellular domain of the EGF receptor results in the inhibition of ligand binding, thereby reducing the EGF-dependent proliferation of tumor cells. In order to analyze this mechanism of action for differently glycosylated Cetuximab variants, proliferation of A431 cells (human epidermoid carcinoma cell line of the vulva) was measured in an MTT assay with different concentrations (0, 1-100 µg/ml) of Cetuximab glycosylated according to the invention and Cetuximab expressed in mouse SP2/0 cells (Erbitux (Merck)). The MTT assay is a non-radioactive assay based on the cleavage of the soluble yellow tetrazolium salt MTT (3-[4,5-Dimethylthiazol-2-yl]-2,5-diphenyltetrazolium bromide; thiazolyl blue) by mitochondrial dehydrogenases of viable cells. This results in the formation of a purple formazan, which can be measured in an ELISA reader at 570 nm. The absorption signal is a direct measure of viable cells in the culture.

As a positive control, proliferation was completely inhibited by addition of taxol, and hIgG or medium alone served as negative controls. Briefly, A431 cells were grown for 4 days in 96-well flat bottom plates. Cetuximab variants and control substances were added and the plates were incubated for another 3-5 days at 37° C. in a humidified $CO_2$ incubator. Supernatant was completely removed and MTT was added. Cells were incubated for 2 h with MTT at 37° C. in a humidified $CO_2$ incubator. The supernatant was removed and cells were lysed using a HCl and 2-propanol containing lysis buffer for 1 h at room temperature in the dark. Absorption at 570 nm/630 nm was measured in a plate reader Infinite F200 (Tecan Austria GmbH).

FIG. 5B shows the results of an experiment performed with Cetuximab glycosylated according to the invention (Cetuximab (invention)) and Cetuximab expressed in mouse SP2/0 cells (Cetuximab SP2/0) on different plates within the same experiment. Controls were added at each plate and are shown in darker color for Cetuximab (invention) and in lighter color for Cetuximab SP2/0. After incubation with Cetuximab, less viable cells were observed compared to the medium (shown in green) and the hIgG1 control (shown in grey). Medium and hIgG1 control showed the same proliferation. The positive control taxol resulted in maximal proliferation inhibition. Cetuximab glycosylated according to the invention and Cetuximab expressed in mouse SP2/0 cells induced a concentration-dependent inhibition of proliferation in A431 cells. The proliferation inhibition was comparable between both Cetuximab variants.

In conclusion, the improved glycosylation pattern of the antibodies according to the present invention does not negatively influence the receptor inhibition activity of the anti-EGFR antibody Cetuximab.

Example 5

Induction of Apoptosis and Target Cell Lysis with Differently Glycosylated Antibodies Induction of Apoptosis Induction of apoptosis is a further mechanism by which antibodies can mediate anti-tumor activity. While direct induction of apoptosis by monomeric antibodies is often ineffective, cross-linking of the antibody by anti-human immunoglobulin or protein G evokes this mechanism of action. In vivo, cross-linking of the antibody can be induced by Fc-receptor-bearing cells.

In order to study this potential mode of action, we analyzed the induction of apoptosis by differently glycosylated Cetuximab variants after cross-linking with protein G on the tumor cell lines LS174T and A431. As a marker for induction of apoptosis, we analyzed the activation of caspase-3 using the BD PE Active Caspase-3 Apoptosis Kit. Caspase-3, a cystein protease, is a key protease that is activated during the early stages of apoptosis. It is synthesized as an inactive pro-enzyme of 32 kDa that is processed in cells undergoing apoptosis. The processed form consists of two subunits (17 kDa and 12 kDa) which associate to form the active caspase. Active caspase-3 proteolytically cleaves and activates other caspases as well as target in the cytoplasm and in the nucleus, thereby promoting apoptosis. Using the BD PE Active Caspase-3 Apoptosis Kit, apoptotic cells are stained using an antibody specific for the active form of caspase-3 that does not recognize the inactive pro-enzyme form of caspase-3.

Briefly, tumor cell lines were cultured in serum free (A431) or serum reduced (1%, LS174T) medium for 24 h prior to the assay. Cells were seeded into 48 well plates incubated at 37° C. in a $CO_2$ incubator for 24 h. Cetuximab variants or hIgG1 as a negative control at different concentrations and protein G at a final concentration of 2 µg/ml were added. The plates were incubated for 4 to 48 h at 37° C. in a $CO_2$ incubator. Cells were harvested, permeabilized, fixed and stained for active caspase-3 according to manufacturer's protocol. Active caspase-3-positive (apoptotic) cells were analyzed by flow cytometry at a BD FACS Canto II flow cytometer using BD FACSDiva™ Software.

After cross-linking by protein G, the Cetuximab variants induced strong concentration-dependent apoptosis in A431 and LS174T cells. As an example, FIG. 6 shows the results of an active caspase-3 apoptosis assay using A431 cells. Apoptosis induction was comparable between Cetuximab glycosylated according to the invention (Cetuximab (invention)) and Cetuximab expressed in mouse SP2/0 cells (Cetuximab SP2/0).

ADCC Assay

To determine the influence of different glycosylation patterns of antibodies on ADCC, europium release assays were performed.

In a first assay, the different lysis of target cells using the anti-EGFR antibody Cetuximab expressed by different cell lines were tested. In particular, the lysis of LS174T cells by human PBMCs using Cetuximab expressed in mouse SP2/0 cells (low Fab sialylation, high Fc fucosylation), rodent CHO cells (low Fab sialylation, high Fc fucosylation), GT-5s (high Fab sialylation, high Fc fucosylation) and Fuc⁻ cells derived from GT-5s (high Fab sialylation, low Fc fucosylation) was tested. The effector to target cell ratio (E:T ratio) was 50:1 and the incubation time was 4 h. The results are shown in FIG. 7.

As demonstrated by this assay, the amount of sialic acid at the Fab part of the antibody does not influence its ADCC activity. However, a lower degree of fucosylation at the Fc part leads to a high ADCC activity.

In a second assay, the lysis of LS174T cells by primary human PBMC obtained from different donors being either homozygous for FcγRIIIa-158F (F/F) or FcγRIIIa-158V (V/V), or being heterozygous for FcγRIIIa (F/V) using Cetuximab expressed in mouse SP2/0 cells (low Fab sialylation, high Fc fucosylation) or Fuc⁻ cells derived from GT-5s (high Fab sialylation, low Fc fucosylation) was determined.

The effector to target cell ratio (E:T ratio) was 80:1 and the incubation time was 5 h. The results are shown in FIGS. 8 to 10.

In a further experiment performed with PBMCs of different donors on the same day (FIG. 11), it is demonstrated that Cetuximab glycosylated according to the invention (Cetuximab (invention)) have a similar ADCC activity for all different donor types. In contrast thereto, specific lysis mediated by Cetuximab expressed in mouse SP2/0 cells (Cetuximab SP2/0) showed a remarkable increase in cytotoxicity on the VV donor compared to the FF donor.

As can be seen, the antibodies having a low degree of fucosylation at the Fc part and a high degree of sialylation at the Fab part (Fuc) have a much higher ADCC activity for all donors than the antibodies having a high degree of fucosylation at the Fc part and a low degree of sialylation at the Fab part (SP2/0). Furthermore, the ADCC activity of the low fucose/high sialic acid antibodies is also comparable for each of the different donors while the high fucose/low sialic acid antibodies show an increased ADCC activity for V/V donors.

In a third assay, the influence of a high sialylation degree on the ADCC activity of the anti-MUC-1 antibody Pankomab was analyzed. In comparative antibody-dependent cell cytotoxicity assays, the effect of the glycosylation of Pankomab produced in a human myeloid cell line essentially lacking sialylation and GT-5s (with high sialylation) and Pankomab produced in CHO was analyzed. All materials were purified by chromatography on a protein A column.

Pankomab expressed in non-sialylating cells and high sialylating cells show comparable specific lysis against ZR-75-1 tumor cells while Pankomab expressed in CHO show a considerably lower lysis. ADCC activity of lowly sialylated and highly sialylated Pankomab is comparable. (see FIG. 12).

Therefore, the fully human glycosylation of Pankomab expressed in GT-5s results in the production of an antibody with a ~5-times higher ADCC activity than Pankomab expressed in CHO-cells.

Furthermore, the lysis of ZR-75-1 cells by primary human PBMC obtained from donors being homozygous for FcγRIIIa-158F (F/F) using the anti-TA-Muc1 antibody Pankomab expressed in GT-5s cells (high Fab sialylation, high Fc fucosylation) or Fuc⁻ cells derived from GT-5s (high Fab sialylation, low Fc fucosylation) was determined. The effector to target cell ratio (E:T ratio) was 100:1 and the incubation time was 6 h. The results are shown in FIG. 13.

As can be seen, the antibodies having a high degree of fucosylation at the Fc part and a high degree of sialylation at the Fab part (GT-5s) have a reasonable high ADCC activity. However, the ADCC activity is even increased for the antibodies with a low fucose content at the Fc part (Fuc).

This increased ADCC activity combined with the improved half-life due to the teachings of the present invention provides antibodies with improved clinical profile.

Example 6

Lysis of Target Cells Having a Constitutively Active K-Ras Mutation with Anti-EGFR Antibodies According to the Invention To demonstrate the ability of anti-EGFR antibodies having an optimized glycosylation pattern according to the present invention to induce lysis of target cells having a constitutively active K-Ras mutation via ADCC, europium release assays were performed.

In the assay, cells of the human lung adenocarcinoma epithelial cell line A549 were used as target cells. The K-Ras gene in these cells comprises a mutation in codon 12 leading to a constitutively active K-Ras protein having a Gly-12-Ser mutation. As effector cells, primary human PBMCs obtained from different donors being homozygous for either FcγRIIIa-158F (F/F) or FcγRIIIa-158V (V/V) were used. Lysis of the target cells via ADCC was induced by the anti-EGFR-antibody Cetuximab glycosylated according to the invention (high Fab sialylation, low Fc fucosylation). The effector to target cell ratio (E:T ratio) was 80:1 and the incubation time was 5 h. The results are shown in FIG. 14.

As demonstrated by this assay, the anti-EGFR antibodies according to the present invention having an improved glycosylation pattern, in particular a high Fab sialylation and a low Fc fucosylation, are capable of inducing target cell lysis via ADCC even for target cancer cells which comprise a constitutively active EGFR signal transduction pathway, i.e. which cannot be treated by blocking EGFR ligand binding.

Example 7

Circulation Half-Life of Differently Glycosylated Antibody Variants

To test the dependency of half-life on the sialylation of an IgG antibody, Cetuximab was expressed in Fuc⁻ cells derived from GT-5s (Cetuximab (invention)) and preparations from differently charged isotypes were produced. A pharmacokinetic study in mice was performed.

Protein A purified IgG antibody was chromatofocused (CF) on an anionic exchanger and separated according to differences in their pI, fractionated and pooled. Glycoprofiling of those preparations eluting at different pH values showed different glycosylation patterns. Additionally, a Fab/Fc specific glycoprofiling as described in Example 1 was recorded and indicates that principally only the Fab glycosylation is relevant for the enrichment of highly sialylated glycans since there are basically no disialylated glycans in the Fc part of the antibody (see FIG. 15A). However, an increase in SA was also achieved in Fc glycans of the more negatively charged pool.

In the pharmacokinetic assay 2 different samples were compared: (A) a mix of pool 1 and pool 2 (high-mid pH range CF), and (B) pool 3 (low pH range CF). Antibody doses of 50 mg/kg were injected into mice and serum samples were taken at specific time points. Samples were analyzed and evaluated with respect to their antibody content by a hIgG titer ELISA. In this study, preparations with a total sialylation degree of 28% (A) and 49% (B) have been compared (see FIG. 15B).

As FIG. 16 shows, preparation A has a significantly shorter circulation half-life ($T_{1/2}$=161.9 h) than the highly sialylated preparation B ($T_{1/2}$=199.5 h). The preparation with lower sialylation, especially with lower S2 in the Fab part, was faster cleared from the serum.

Example 8

Anti-Tumor Activity of Differently Glycosylated Antibodies

Anti-EGFR Antibodies in A431 Xenografts

For comparison of differently glycosylated antibodies A431 epidermal vulva carcinoma cells were used to set up a mouse xenograft model. This cell line is expressing the EGFR protein highly.

Cetuximab glycosylated according to the invention (Cetuximab (invention)) and Cetuximab expressed in SP2/0 cells (Cetuximab SP2/0) were administered intravenously twice weekly for 3 weeks at dose levels of 5 mg/kg and 50 mg/kg (N=8f/group). The application volume was 10 µl/g body weight for both antibody formulations. Adjustment of the concentration in the injection solution was done by dilution with PBS.

The mean relative tumor volumes of the treated animals are shown in FIG. 17. Both antibodies inhibit tumor growth dose-dependently compared to PBS treated animals (p<0.001). The results of the Cetuximab SP2/0 treated groups are in agreement with published data (Fichtner et al. 2008, Steiner et al. 2007, Goldstein et al. 1995). No significant difference between the relative tumor volume in the Cetuximab (invention) treated group and the Cetuximab SP2/0 treated group was found in any of the dose groups. Comparable efficacies of Cetuximab (invention) and Cetuximab SP2/0 were expected since the advantage of the increased ADCC activity of Cetuximab (invention) is not relevant in mice.

All animals survived until the scheduled study end. No significant changes in the body weight of the animals were observed indicating that no major toxicity occurred in the treated animals.

Anti-EGFR Antibodies in DU145 Xenografts

Additionally, the in vivo efficacy of Cetuximab (invention) was studied in athymic nude mice bearing DU145 human prostatic carcinoma xenografts. The DU145 cell line is EGFR positive and DU145 xenografts have been reported to be sensitive to Erbitux® treatment.

A preliminary study has shown that the administration of 50 mg/kg Cetuximab (invention) twice weekly for 3 weeks resulted in a strong antitumor effect compared to the control group. Subsequently, a dose range finding study including five different dose levels ranging from 0.5 mg/kg to 50 mg/kg was performed. Cetuximab (invention) (N=7-8 m/group) was intravenously administered twice weekly for 4 weeks. Adjustment of the concentration in the injection solution was done by dilution with formulation buffer. The application volume was kept constant at 10 µl/g body weight. None of the treated animals died during the course of the study. No significant changes in the body weight of the animals were observed indicating that no major toxicity occurred.

The mean relative tumor volume of the animals is shown in FIG. 18. Cetuximab (invention) inhibited strongly and dose-dependently the DU145 tumor growth compared to vehicle treated animals (p<0.001). Dose levels from 0.5 to 50 mg/kg were shown to be efficacious in inhibition of tumor growth. Higher doses resulted in a faster and more pronounced effect compared to lower doses.

Anti-MUC1 Antibodies in ZR-75-1 Xenografts

The antitumor efficacy of Pankomab with different sialylation degrees obtained by expression in different cell lines was investigated in a further study. The therapeutic potential of both antibodies was investigated in ZR-75-1 xenografted nude mice. ZR-75-1 tumor cells were injected s.c. and allowed to grow up to an average size of ~0.1 cm³. Sialylated Pankomab expressed in GT-5s cells (Pankomab sial.+) or the non-sialylated Pankomab expressed in a sialylation-deficient, human myeloid tumor cell line (Pankomab sial.−) were i.v. administered into groups of 8 mice two times per week over a period of 4 weeks. Doses of 0.5 mg/kg was applied each and PBS served as a control. Body weight and tumor growth were monitored. As a result the low dose of 0.5 mg/kg of the sialylated Pankomab was highly effective to inhibit the tumor growth whereas the non-sialylated Pankomab was less effective. FIG. 19 shows the results based on relative tumor volumes. All results were expressed as the mean±standard error of mean. A two way ANOVA of relative tumor volumes was performed for testing the influence of treatment duration and antibody concentration (GraphPad Prism software v5.02, GraphPad Software, USA). Bonferroni posttests with a p value of 0.05 were used to assess statistical significance of difference between pairs of groups.

In summary, a low dose of the sialylated Pankomab expressed in GT-5s cells (0.5 mg/kg) caused an effective tumor growth inhibition in ZR-75-1 xenografted nude mice (p<0.001). The higher efficacy of the sialylated Pankomab compared to the non-sialylated Pankomab is considered to be caused by a slower clearance of the sialylated antibody from the circulation and therefore a longer bioavailability.

Example 9

Anti-Tumor Activity Against Different Patient-Derived Tumors

In this study, the in vivo efficacy of Cetuximab glycosylated according to the invention (Cetuximab (invention)) was assessed in immune deficient mice bearing human patient derived carcinoma xenografts of NSCLC (non-small cell lung cancer) and CRC (colorectal cancer) origin. Xenografts of patient derived tumor cells are supposed to be even more similar to the original tissue than tumor cell lines and therefore considered to be of higher clinical relevance. Tumor models were selected according to their positive EGFR expression status which has been evaluated immunohistochemically, as well as to their K-Ras mutational status. NSCLC #7466 and CRC #8397 both show a high EGFR expression, whereas NSCLC #7466 comprises wild-type K-Ras while CRC #8397 carries the oncogenic, constantly active G12D mutant of K-Ras.

Cetuximab (invention) (N=8 m/group) was administered i.v. twice weekly for 3 weeks at dose levels of 5 mg/kg and 50 mg/kg. Adjustment of the concentration in the injection solution was done by dilution with formulation buffer. The application volume was kept constant at 10 µl/g body weight. The mean relative tumor volume of the animals is shown in FIG. 20. As demonstrated, Cetuximab (invention) effectively inhibits growth of the human patient-derived tumors, independent of their K-Ras mutational status.

None of the animals of the Cetuximab (invention) treated groups died prematurely prior to the end of the study. No significant changes in the body weight of the animals were observed indicating that no toxicity occurred.

Example 10

Toxicological Studies

A 4 week repeat-dose toxicity study in cynomolgus monkeys and a 2-week dose-range-finding study in cynomolgus monkeys were conducted. Based upon these toxicity studies, the safety profile of Cetuximab glycosylated according to the invention (Cetuximab (invention)) provides sufficient weight of evidence that the monoclonal antibody drug candidate is well-tolerated and thus, the treatment of the selected patient population will be safe. No unusual or alarming indices of toxicity were observed that would preclude the use of the anti-EGFR antibody in humans.

In contrast to mice it was shown that cynomolgus monkeys show in vitro and in vivo an increased ADCC activity with de-core fucosylated human IgG1 which is comparable to that of the respective ADCC increase in human test systems. Therefore it can be concluded that any theoretically potential increase in an ADCC mediated toxicity of the glycol-optimized Cetuximab compared to the commercially available Cetuximab (Erbitux) should have been shown in the cynomolgus monkey model.

A further toxicity study was performed with the anti-MUC1 antibody Pankomab in Wistar rats at Aurigon Life Science GmbH under GLP conditions according to national and international guidelines (German Chemicals Law 2002, OECD 1997, Directive of the European Parliament and of the Council 2004). This study included a dose range finding study for Pankomab expressed in GT-5s cells administered intravenously to female rats, and a 4-week intravenous repeated dose toxicity study in male and female rats followed by a 14-days recovery period. Results of the dose range finding study and in-life observations of the 28 day repeating dose toxicity study do not indicate any compound related effects.

The results provide sufficient evidence that the toxicological profiles of the antibodies according to the present invention, i.e. having the improved glycosylation pattern described herein, do not show any increased toxicology and are comparable to the state of the art antibodies not having the improved glycosylation pattern.

The invention claimed is:

1. A method for treatment of cancer in a patient in need thereof, comprising administering to the patient a therapeutically effective amount of antibody composition comprising a chimeric or humanized anti-EGFR antibody or fragment or derivative thereof, comprising a heavy chain variable region comprising a CDRH1 comprising the amino acid sequence of SEQ ID NO: 1, a CDRH2 comprising the amino acid sequence of SEQ ID NO: 2 and a CDRH3 comprising the amino acid sequence of SEQ ID NO: 3; and a light chain variable region comprising a CDRL1 comprising the amino acid sequence of SEQ ID NO: 4, a CDRL2 comprising the amino acid sequence of SEQ ID NO: 5and a CDRL3 comprising the amino acid sequence of SEQ ID NO: 6; wherein the antibody comprises the following characteristics:

(i) the antibody comprises a glycosylation site present in the Fc part;
(ii) in the composition at least 70% of the carbohydrates attached to the Fc part do not carry a fucose residue;
(iii) in the composition at least 70% of the carbohydrates attached to the Fc part do not carry a sialic acid residue;
(iv) in the composition at least 5% of the carbohydrates attached to the Fc part carry a bisecting acetylglucosamine residue;
(v) in the composition at least 60% of the carbohydrates attached to the antibody carry at least one galactose residue;
(vi) the carbohydrates attached to the antibody do not comprise a Galili epitope having the structure Galα(1→3)Galβ(1→4)GlcNAc; and
(vii) the carbohydrates attached to the antibody do not comprise N-glycolylneuraminic acid (NeuGc) residues;
(viii) optionally, in the composition at least 50% of the carbohydrates attached to the Fab part of the antibody or fragment or derivative thereof carry bisGlcNAc, wherein the patient is treated after failure of cetuximab treatment.

2. The method according to claim 1, wherein the antibody
(i) comprises a glycosylation site present in the Fab part at amino acid position 85 of the heavy chain variable region according to the Kabat numbering, wherein at least 65% of the carbohydrates attached to said glycosylation site present in the Fab part carry at least one terminal sialic acid residue; and/or less than 35% of the carbohydrates attached to said glycosylation site present in the Fab part carry at least two free galactose units; or
ii) does not comprise a glycosylation site in the Fab part.

3. The method according to claim 1, wherein the patient has at least one allele coding for FcγRIIIa-158F.

4. The method according to claim 1, wherein the treatment is independent of the FcγRIIIa genotype of the patient.

5. A method for treatment of cancer in a patient in need thereof, comprising administering to the patient a therapeutically effective amount of antibody composition comprising a chimeric or humanized anti-EGFR antibody or fragment or derivative thereof, comprising a heavy chain variable region comprising a CDRH1 comprising the amino acid sequence of SEQ ID NO: 1, a CDRH2 comprising the amino acid sequence of SEQ ID NO: 2 and a CDRH3comprising the amino acid sequence of SEQ ID NO: 3; and a light chain variable region comprising a CDRL1 comprising the amino acid sequence of SEQ ID NO: 4, a CDRL2 comprising the amino acid sequence of SEQ ID NO:5 and a CDRL3 comprising the amino acid sequence of SEQ ID NO: 6; wherein the antibody comprises the following characteristics:
  (i) the antibody comprises a glycosylation site present in the Fc part;
  (ii) in the composition at least 70% of the carbohydrates attached to the Fc part do not carry a fucose residue;
  (iii) in the composition at least 70% of the carbohydrates attached to the Fc part do not carry a sialic acid residue;
  (iv) in the composition at least 5% of the carbohydrates attached to the Fc part carry a bisecting N-acetylglucosamine residue;
  (v) in the composition at least 60% of the carbohydrates attached to the antibody carry at least one galactose residue;
  (vi) the carbohydrates attached to the antibody do not comprise a Galili epitope having the structure Galα(1→3)Galβ(1→4)GlcNAc; and
  (vii) the carbohydrates attached to the antibody do not comprise N-glycolylneuraminic acid (NeuGc) residues;
  (viii) optionally, in the composition at least 50% of the carbohydrates attached to the Fab part of the antibody or fragment or derivative thereof carry bisGlcNAc;
wherein the tumor cells comprise at least one activating mutation in an EGFR signal transduction pathway.

6. The method according to claim 5, wherein the antibody
  i) comprises a glycosylation site present in the Fab part at amino acid position 85 of the heavy chain variable region according to the Kabat numbering, wherein at least 65% of the carbohydrates attached to said glycosylation site present in the Fab part carry at least one terminal sialic acid residue; and/or less than 35% of the carbohydrates attached to said glycosylation site present in the Fab part carry at least two free galactose units; or
  ii) does not comprise a glycosylation site in the Fab part.

7. The method according to claim 5, wherein the activating mutation results in a constitutively active K-Ras mutant, a constitutively active PI 3 kinase mutant, or an overexpression of Raf kinase.

8. The method according to claim 5, wherein the patient has at least one allele coding for FcγRIIIa-158F.

9. The method according to claim 5, wherein the treatment is independent of the FcγRIIIa genotype of the patient.

10. A method for treatment of cancer in a patient in need thereof, comprising administering to the patient a therapeutically effective amount of antibody composition comprising a chimeric or humanized anti-EGFR antibody or fragment or derivative thereof, comprising a heavy chain variable region comprising a CDRH1 comprising the amino acid sequence of SEQ ID NO: 1, a CDRH2 comprising the amino acid sequence of SEQ ID NO: 2 and a CDRH3comprising the amino acid sequence of SEQ ID NO: 3; and a light chain variable region comprising a CDRL1 comprising the amino acid sequence of SEQ ID NO: 4, a CDRL2 comprising the amino acid sequence of SEQ ID NO:5 and a CDRL3 comprising the amino acid sequence of SEQ ID NO: 6; wherein the antibody comprises the following characteristics:
  (i) the antibody comprises a glycosylation site present in the Fc part;
  (ii) in the composition at least 70% of the carbohydrates attached to the Fc part do not carry a fucose residue;
  (iii) in the composition at least 70% of the carbohydrates attached to the Fc part do not carry a sialic acid residue;
  (iv) in the composition at least 5% of the carbohydrates attached to the Fc part carry a bisecting N-acetylglucosamine residue;
  (v) in the composition at least 60% of the carbohydrates attached to the antibody carry at least one galactose residue;
  (vi) the carbohydrates attached to the antibody do not comprise a Galili epitope having the structure Galα(1→3)Galβ(1→4)GlcNAc; and
  (vii) the carbohydrates attached to the antibody do not comprise N-glycolylneuraminic acid (NeuGc) residues;
  (viii) optionally, in the composition at least 50% of the carbohydrates attached to the Fab part of the antibody or fragment or derivative thereof carry bisGlcNAc;
wherein the patient is treated after failure of a treatment with an agent which blocks ligand binding to EGFR.

11. The method according to claim 10, wherein the antibody
  i) comprises a glycosylation site present in the Fab part at amino acid position 85 of the heavy chain variable region according to the Kabat numbering, wherein at least 65% of the carbohydrates attached to said glycosylation site present in the Fab part carry at least one terminal sialic acid residue; and/or less than 35% of the carbohydrates attached to said glycosylation site present in the Fab part carry at least two free galactose units; or
  ii) does not comprise a glycosylation site in the Fab part.

* * * * *